(12) United States Patent
Donner et al.

(10) Patent No.: US 11,213,325 B2
(45) Date of Patent: *Jan. 4, 2022

(54) SPINAL STABILIZATION SYSTEM WITH ADJUSTABLE INTERLAMINAR DEVICES

(71) Applicant: JCBD, LLC, Fort Collins, CO (US)

(72) Inventors: Edward Jeffrey Donner, Fort Collins, CO (US); Christopher Thomas Donner, Fort Collins, CO (US); Hai Trieu, Cordova, TN (US); James Duncan, Hernando, MS (US)

(73) Assignee: JCBD, LLC, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/164,785

(22) Filed: Oct. 18, 2018

(65) Prior Publication Data

US 2019/0175229 A1   Jun. 13, 2019

Related U.S. Application Data

(63) Continuation-in-part of application No. 14/498,333, filed on Sep. 26, 2014, now Pat. No. 10,154,861, which is a continuation-in-part of application No. 14/209,138, filed on Mar. 13, 2014, now Pat. No. 9,510,872.

(60) Provisional application No. 61/794,543, filed on Mar. 15, 2013, provisional application No. 62/670,800, filed on May 13, 2018, provisional application No. 62/631,631, filed on Feb. 17, 2018, provisional application No. 62/574,101, filed on Oct. 18, 2017,
(Continued)

(51) Int. Cl.
*A61B 17/70* (2006.01)

(52) U.S. Cl.
CPC ...... *A61B 17/7067* (2013.01); *A61B 17/7043* (2013.01); *A61B 17/7052* (2013.01); *A61B 17/7071* (2013.01); *A61B 17/7079* (2013.01); *A61B 17/7086* (2013.01); *A61B 17/7091* (2013.01); *A61B 17/7026* (2013.01); *A61B 17/7077* (2013.01)

(58) Field of Classification Search
CPC ..... A61B 17/7049–7059; A61B 17/7062–707; A61B 17/70
See application file for complete search history.

(56) References Cited

U.S. PATENT DOCUMENTS 5,306,275 A * 4/1994 Bryan ................ A61B 17/1757
                                                        606/250
5,645,599 A * 7/1997 Samani ............... A61B 17/7062
                                                        606/248

(Continued)

*Primary Examiner* — Eduardo C Robert
*Assistant Examiner* — Michelle C Eckman
(74) *Attorney, Agent, or Firm* — Glenn H. Lenzen; Elevated IP, LLC

(57) ABSTRACT

An adjustable spinal stabilization system for maintaining preselected spacing and movement between adjacent vertebrae in a spinal column and for providing overall stability thereto. The system includes at least one interlaminar member positioned in the spaces intermediate a first vertebra and the vertebrae positioned immediately above or immediately below and adjacent to the first vertebra. The interlaminar member is operatively connected to an adjustable support structure and cooperates therewith to maintain the preselected spacing between adjacent vertebrae and to provide overall stability to the spinal column.

5 Claims, 59 Drawing Sheets

Related U.S. Application Data provisional application No. 61/949,254, filed on Mar. 7, 2014, provisional application No. 61/939,484, filed on Feb. 13, 2014, provisional application No. 61/962,011, filed on Oct. 29, 2013, provisional application No. 61/883,398, filed on Sep. 27, 2013, provisional application No. 61/883,018, filed on Sep. 26, 2013.

(56) References Cited

U.S. PATENT DOCUMENTS

| | | | | |
|---|---|---|---|---|
| 5,702,452 A * | 12/1997 | Argenson | | A61B 17/7049 606/250 |
| 5,947,965 A * | 9/1999 | Bryan | | A61B 17/1757 606/250 |
| 6,440,169 B1 * | 8/2002 | Elberg | | A61B 17/7062 623/17.11 |
| 7,491,238 B2 * | 2/2009 | Arnin | | A61B 17/7043 623/17.14 |
| 7,658,752 B2 * | 2/2010 | Labrom | | A61B 17/7043 606/249 |
| 8,202,299 B2 * | 6/2012 | Wang | | A61B 17/7062 606/246 |
| 8,562,653 B2 * | 10/2013 | Alamin | | A61B 17/7062 606/263 |
| 8,663,283 B2 * | 3/2014 | Belliard | | A61B 17/7053 606/248 |
| 8,721,687 B2 * | 5/2014 | Butler | | A61B 17/7068 606/248 |
| 8,840,646 B2 * | 9/2014 | Vittur | | A61F 2/44 606/247 |
| 9,381,047 B2 * | 7/2016 | Sheffer | | A61B 17/7062 |
| 9,456,854 B1 * | 10/2016 | Powell | | A61B 17/7068 |
| 9,681,897 B2 * | 6/2017 | Faulhaber | | A61B 17/7064 |
| 10,278,745 B2 * | 5/2019 | Woodworth | | A61B 17/7067 |
| 10,363,071 B2 * | 7/2019 | Lowery | | |
| 10,390,864 B2 * | 8/2019 | Sheffer | | |
| 10,398,478 B2 * | 9/2019 | Ganter | | |
| 2002/0040223 A1 * | 4/2002 | Sato | | A61B 17/7067 606/261 |
| 2002/0143327 A1 * | 10/2002 | Shluzas | | A61B 17/7049 606/252 |
| 2003/0060823 A1 * | 3/2003 | Bryan | | A61B 17/7011 606/86 A |
| 2003/0153915 A1 * | 8/2003 | Nekozuka | | A61B 17/7062 606/248 |
| 2003/0187435 A1 * | 10/2003 | Lin | | A61B 17/7001 606/250 |
| 2006/0015181 A1 * | 1/2006 | Elberg | | A61B 17/7062 623/16.11 |
| 2006/0241601 A1 * | 10/2006 | Trautwein | | A61B 17/7067 606/248 |
| 2007/0123861 A1 * | 5/2007 | Dewey | | A61B 17/7067 606/86 A |
| 2007/0161993 A1 * | 7/2007 | Lowery | | A61B 17/7055 606/279 |
| 2007/0191834 A1 * | 8/2007 | Bruneau | | A61B 17/7055 606/279 |
| 2007/0233068 A1 * | 10/2007 | Bruneau | | A61B 17/7067 623/17.11 |
| 2007/0233077 A1 * | 10/2007 | Khalili | | A61B 17/7067 606/86 A |
| 2007/0233089 A1 * | 10/2007 | DiPoto | | A61B 17/7011 606/279 |
| 2007/0233256 A1 * | 10/2007 | Ohrt | | A61F 2/4405 623/17.11 |
| 2007/0299445 A1 * | 12/2007 | Shadduck | | A61B 17/7011 606/86 A |
| 2008/0015585 A1 * | 1/2008 | Berg | | A61B 17/7064 606/279 |
| 2008/0208256 A1 * | 8/2008 | Thramann | | A61B 17/70 606/246 |
| 2008/0243186 A1 * | 10/2008 | Abdou | | A61B 17/7032 606/246 |
| 2008/0281361 A1 * | 11/2008 | Vittur | | A61B 17/7052 606/249 |
| 2008/0281423 A1 * | 11/2008 | Sheffer | | A61B 17/7062 623/17.11 |
| 2009/0018662 A1 * | 1/2009 | Pasquet | | A61B 17/7008 623/17.16 |
| 2009/0036925 A1 * | 2/2009 | Sala | | A61B 17/7023 606/246 |
| 2009/0062915 A1 * | 3/2009 | Kohm | | A61B 17/7038 606/280 |
| 2009/0149885 A1 * | 6/2009 | Durward | | A61B 17/7055 606/246 |
| 2009/0187217 A1 * | 7/2009 | Weiman | | A61B 17/7052 606/257 |
| 2009/0204150 A1 | 8/2009 | Hochschuler | | |
| 2009/0204151 A1 * | 8/2009 | Bracken | | A61B 17/7049 606/246 |
| 2009/0248078 A1 * | 10/2009 | Dant | | A61B 17/7007 606/246 |
| 2009/0270920 A1 * | 10/2009 | Douget | | A61B 17/7055 606/254 |
| 2010/0023058 A1 * | 1/2010 | Tornier | | A61B 17/7043 606/246 |
| 2010/0030266 A1 * | 2/2010 | Martin | | A61B 17/7067 606/246 |
| 2010/0049252 A1 * | 2/2010 | Smisson, III | | A61B 17/7043 606/250 |
| 2010/0069965 A1 * | 3/2010 | Abdou | | A61B 17/7062 606/279 |
| 2010/0121381 A1 * | 5/2010 | Berta | | A61B 17/7055 606/264 |
| 2010/0318133 A1 * | 12/2010 | Tornier | | A61B 17/7067 606/270 |
| 2011/0106163 A1 * | 5/2011 | Hochschuler | | A61B 17/7062 606/264 |
| 2011/0137345 A1 * | 6/2011 | Stoll | | A61B 17/7049 606/251 |
| 2012/0078303 A1 * | 3/2012 | Malek | | A61B 17/7067 606/250 |
| 2012/0109201 A1 * | 5/2012 | Kretzer | | A61B 17/7049 606/248 |
| 2012/0109202 A1 * | 5/2012 | Kretzer | | A61B 17/7049 606/248 |
| 2012/0184997 A1 * | 7/2012 | Simonson | | A61B 17/7007 606/265 |
| 2013/0030467 A1 * | 1/2013 | Karas | | A61B 17/686 606/248 |
| 2013/0090692 A1 * | 4/2013 | Nuckley | | A61B 17/7047 606/277 |
| 2013/0103088 A1 * | 4/2013 | Karahalios | | A61B 17/7068 606/248 |
| 2013/0238033 A1 * | 9/2013 | Black | | A61B 17/7055 606/286 |
| 2013/0296939 A1 * | 11/2013 | Perkins | | A61B 17/7068 606/249 |
| 2014/0074166 A1 * | 3/2014 | Scarrow | | A61B 17/7067 606/247 |
| 2014/0155940 A1 * | 6/2014 | Dubois | | A61B 17/7067 606/249 |
| 2014/0277148 A1 * | 9/2014 | Blain | | A61B 17/7035 606/263 |
| 2014/0277163 A1 * | 9/2014 | Kretzer | | A61B 17/7049 606/278 |
| 2014/0296917 A1 * | 10/2014 | Donner | | A61B 17/7026 606/248 |
| 2015/0012040 A1 * | 1/2015 | Agarwal | | A61B 17/7068 606/248 |
| 2015/0182263 A1 * | 7/2015 | Donner | | A61B 17/7067 606/248 |
| 2015/0196328 A1 * | 7/2015 | Hirschl | | A61B 17/7056 606/276 |
| 2016/0220285 A1 * | 8/2016 | Fortin | | A61B 17/7071 |
| 2016/0235447 A1 * | 8/2016 | Mundis, Jr. | | A61B 17/7001 |
| 2017/0007299 A1 * | 1/2017 | Mundis, Jr. | | A61B 17/7083 |
| 2018/0008321 A1 * | 1/2018 | Stern | | A61B 17/7002 |
| 2018/0078286 A1 * | 3/2018 | Le Couedic | | A61B 17/7043 |

(56) References Cited

U.S. PATENT DOCUMENTS

2019/0008656 A1\* 1/2019 Salvermoser ......... A61F 2/4611
2019/0029733 A1\* 1/2019 Mickiewicz ....... A61B 17/7043
2019/0175229 A1\* 6/2019 Donner .............. A61B 17/7067

\* cited by examiner

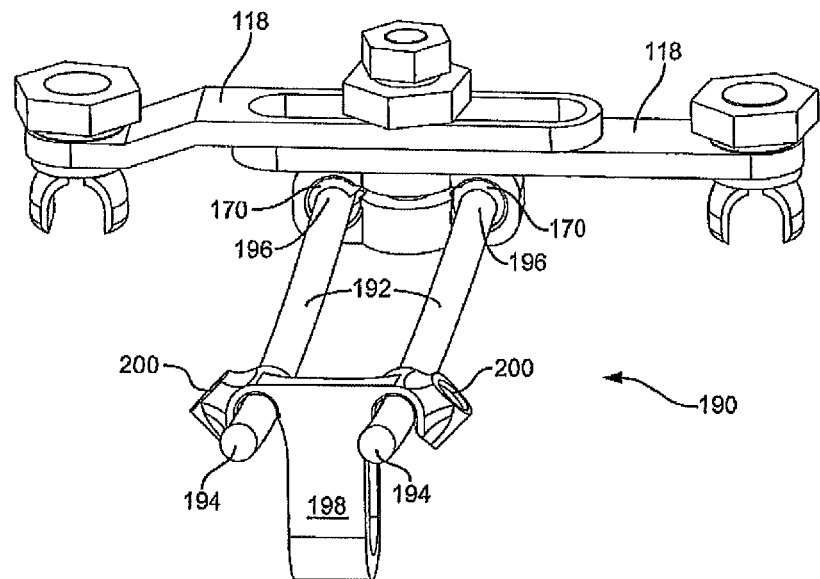
FIG. 19A
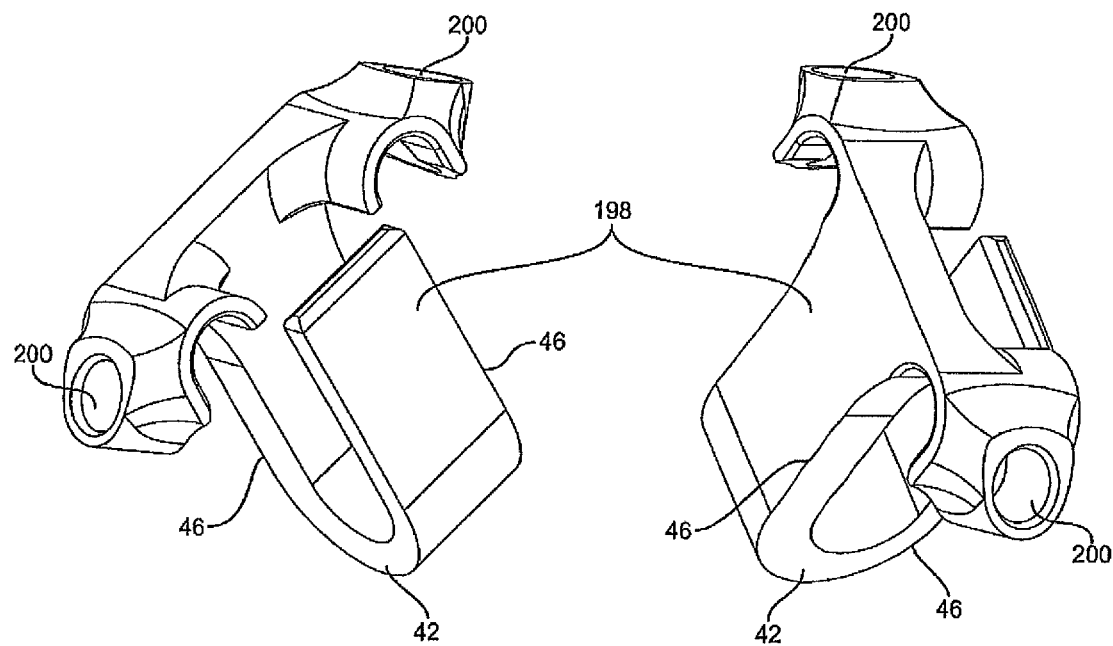
FIG. 19B
FIG. 19C

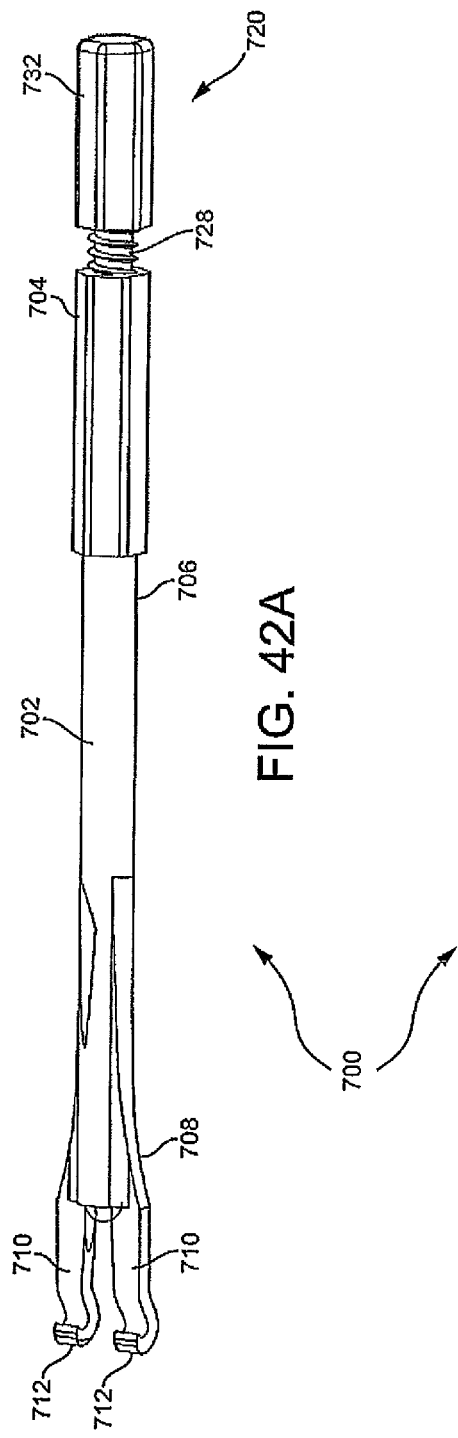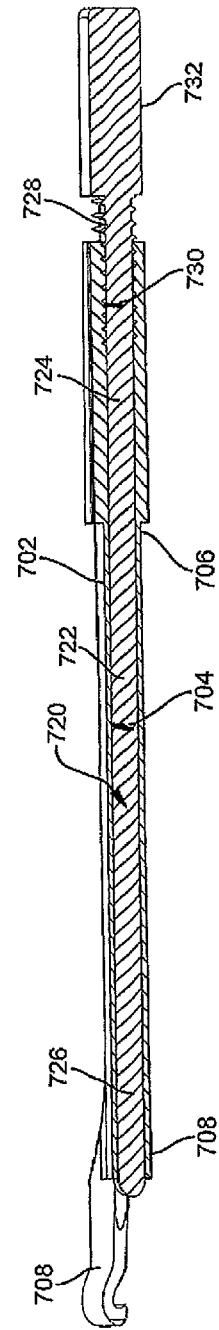
FIG. 42A
FIG. 42B

SPINAL STABILIZATION SYSTEM WITH ADJUSTABLE INTERLAMINAR DEVICES

CROSS-REFERENCE TO RELATED APPLICATIONS

The present application is a continuation-in-part application of U.S. patent application Ser. No. 14/498,333, now U.S. Pat. No. 10,154,861, filed on Sep. 26, 2014, which application is a continuation-in-part application of U.S. patent application Ser. No. 14/209,138, now U.S. Pat. No. 9,510,872, filed on Mar. 13.2014, which application claims priority to U.S. Provisional Patent Application No. 61/794,543 filed on Mar. 15, 2013. Application Ser. No. 14/498,333 also claims the benefit of and priority to U.S. Provisional Patent Application Nos. 61/949,254 filed on Mar. 7.2014, 61/939,484 filed on Feb. 13, 2014, 61/962,011 filed on Oct. 29, 2013, 61/883,398 filed on Sep. 27, 2013, and 61/883,018 filed on Sep. 26, 2013. The present application also claims the benefit of and priority under 35 U.S.C. 6119 to U.S. Provisional Patent Application Nos. 62/670,800 filed on Mar. 13, 2018, 62/631,631 filed on Feb. 17, 2018 and 62/574,101 filed on Oct. 18, 2017. All of the aforementioned patents and patent applications are hereby incorporated by reference in their entireties into the present application for all purposes.

FIELD OF THE INVENTION

The present invention relates generally to the field of medical apparatus and methods for using the same. More specifically, the present invention relates to systems and methods for treating spinal conditions, and specifically for systems for stabilizing vertebrae in the spinal column. More specifically, the present invention relates to adjustable and fixed interlaminar vertebral stabilization devices for placement between adjacent vertebra and including supporting devices for stabilization of the vertebral segments above and below the vertebra being treated.

BACKGROUND OF THE INVENTION

Injury to and/or diseases of the spine frequently result in damage to or abnormalities in the vertebrae, the intervertebral discs, the facet joints and to the connective tissue and ligaments around the spine. Such damage or abnormalities may result in spinal instability causing misalignment of the vertebral column and wear of the intervertebral discs and vertebral bony surfaces, a chronic and progressive deterioration which typically results in severe pain, loss or restriction of motion, and eventually, loss of mobility of the individual suffering from the condition.

One treatment option for addressing spinal disorders is via surgical intervention and the placement of fusion, stabilization and/or repair devices on or adjacent to the spine or between adjacent vertebrae. Certain surgical procedures are irreversible, for example, fusion techniques using bone grafts or synthetic implants to fuse vertebra, and may also significantly alter vertebral range of motion. Other procedures, for example procedures for installing spinal implants or pedicle screw systems for fixating two or more vertebrae, are intricate, time consuming and highly invasive. Alternative solutions include the insertion of interspinous or intralaminar spacers in the space between adjacent vertebrae to control relative motion between and to stabilize the two vertebrae. However, the stabilization does not extend above or below the insertion point, leaving the remaining portions of the spinal column subject to unstable motion and the potential damage resulting therefrom.

Various prior art systems have attempted to address the problems described above. U.S. Pat. No. 5,645,599 issued to Samani on Jul. 8, 1997 (the '599 patent), discloses an interspinal implant device having a generally U-shaped, spring-like configuration for insertion between the spinal processes of adjacent vertebrae. Samani's device includes opposing pairs of upwardly and downwardly extending brackets adapted to be secured to the spinal process, thereby providing for flexible positioning of the adjacent vertebrae. However, the apparatus of the '599 patent does not attribute to the overall stability of the spinal column; its effect being limited to the two specific vertebrae to which it is attached. It is also difficult to attach multiple devices configured in accordance with Samani's disclosure at adjacent segments due to interference of the bracket portions.

Hochschuler et al. disclose various intra-laminar stabilization systems in U. S. Patent Application Publication No. US 2009/0204150 published on Aug. 13, 2009 (the '150 publication), and in U.S. Patent Application Publication No. US 2011/0106163 published on May 5, 2011 (the '163 publication). The '150 publication discloses a pair of oppositely disposed hook members that are translationally positioned on a rod and adapted to engage the laminar regions of adjacent vertebra and maintain a preselected spacing there between. However, the apparatus of the '150 publication does not stabilize other vertebrae in the spinal column, its effect being limited to the two adjacent vertebrae which it engages.

The Hochschuler et al. '163 publication discloses an interlaminar stabilizing system which includes a structure adapted to be disposed between two adjacent vertebrae as described above with respect to the apparatus of the '150 publication. The '163 structure further includes a support structure which is secured to the second vertebra to further restrict the interval spacing between the adjacent vertebrae. However, the system of the '163 disclosure also does not stabilize the vertebrae in the remaining portions of the spinal column for the reasons set forth above.

Moreover, none of the known prior art systems address the problem of "transition syndrome" or "adjacent segment disease" associated with fusion of adjacent vertebrae. In fusion, if a motion segment is eliminated via fusion, the unfused adjacent segments above and below the fused vertebrae take up and bear the additional forces induced by bending and rotational movement of the spine, which may result in so-called "transition syndrome" over the long term. In addition, none of the prior art systems provide for augmenting previously installed spinal hardware to enhance stability, adjust intervertebral distraction, and so forth.

Accordingly, a need exists for an improved spinal stabilization system which provides both flexibility and stability to the spinal column and which addresses the combination of problems not solved by the prior art.

SUMMARY OF THE INVENTION

In order to achieve the above-mentioned objectives, the present invention provides an improved spinal stabilization system for maintaining preselected spacing and movement between adjacent vertebrae and also which provides overall stability to the spinal column.

In one embodiment, a spinal stabilization system is provided which includes at least one interlaminar member adapted to be inserted between two adjacent vertebrae and a stabilizing structure for stabilizing the vertebrae at least one layer above and below the two adjacent vertebrae.

In another embodiment, a spinal stabilization system is provided which includes a blocking member to limit movement of adjacent vertebrae to prevent narrowing of the spinal canal and nerve compression.

In yet another embodiment, a spinal stabilization system is provided which includes at least one adjustable cross-linking member to enhance stability of the spine.

In still another embodiment, a spinal stabilization system is provided which includes at least one adjustable interlaminar member adapted to be adjusted in response to the anatomy of a patient.

In an embodiment, a spinal stabilization system is provided which includes an interlaminar member adapted to be adjustable in response to the interlaminar spacing intermediate an adjacent pair of vertebrae.

In yet another embodiment, a spinal stabilization system is provided which includes an interlaminar member adapted to be angularly adjustable with respect to a cross-linking member.

In another embodiment, a spinal stabilization system is provided which includes an interlaminar member having a portion of variable shape adapted to be placed intermediate an adjacent pair of vertebrae, the variable shaped portion being shaped to conform to an interspinous anatomy unique to a patient being treated.

These and other features, aspects and advantages of the present invention will be apparent from the accompanying detailed description of the invention, which, taken with the appended drawings, discloses a preferred and alternate embodiments thereof.

BRIEF DESCRIPTION OF THE DRAWINGS

FIG. 19(A) is a top front perspective view of the spinal stabilization system shown in FIG. 18;

FIG. 19(B) is a front side perspective view of portions of the spinal stabilization system shown in FIGS. 18 and 19(A);

FIG. 19(C) is a rear side perspective view of portions of the spinal stabilization system shown in FIGS. 18, 19(A) and 19(8);

FIG. 42(A) is a side plan view of a spinal stabilization insertion tool in accordance with an embodiment of the present invention;

FIG. 42(B) is a side sectional view of the insertion tool shown in FIG. 42(A);

DESCRIPTION OF THE INVENTION

It should be noted that the present description is by way of illustration only, and that the concepts and examples presented herein are not limited to use or application with any single system or methodology. Hence, while the details of the system and methods described herein are for the convenience of illustration and explanation with respect to the exemplary embodiments, the principles disclosed may be applied to other types of spinal stabilization systems without departing from the scope of the present invention.

Figure 1:
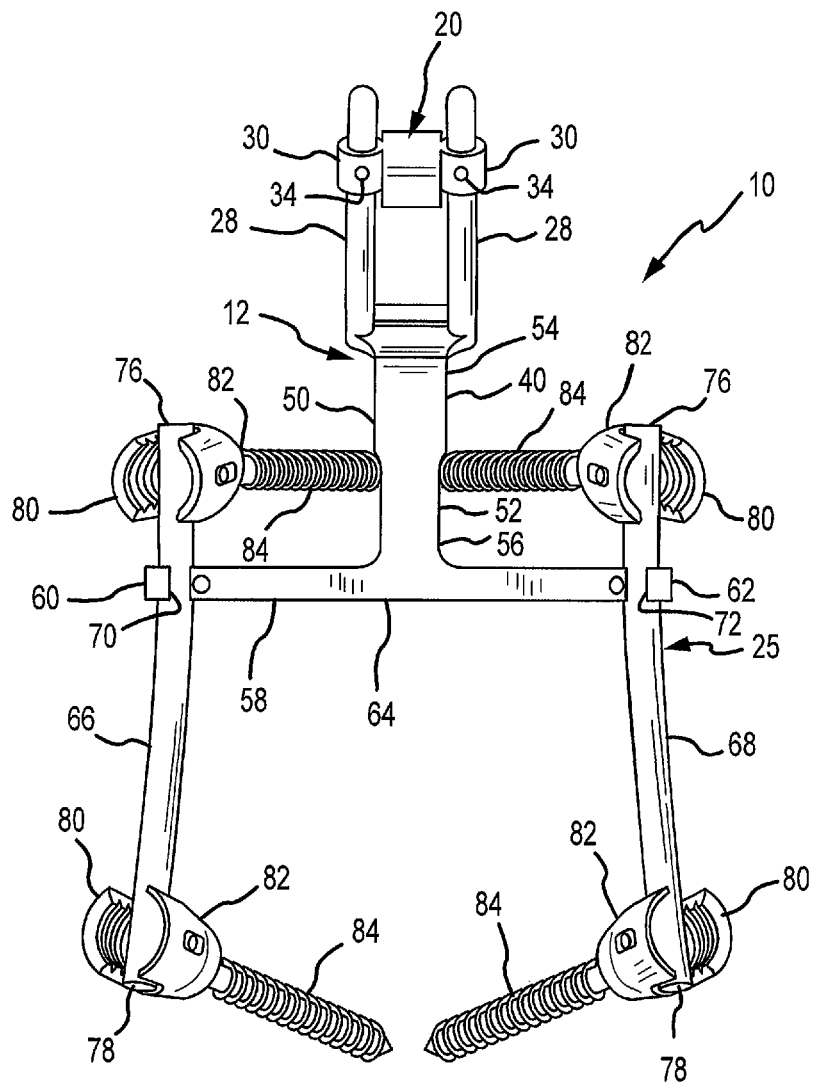
FIG. 1 is a front plan view of a spinal stabilization system in accordance with an embodiment of the present invention.
Figure 2:
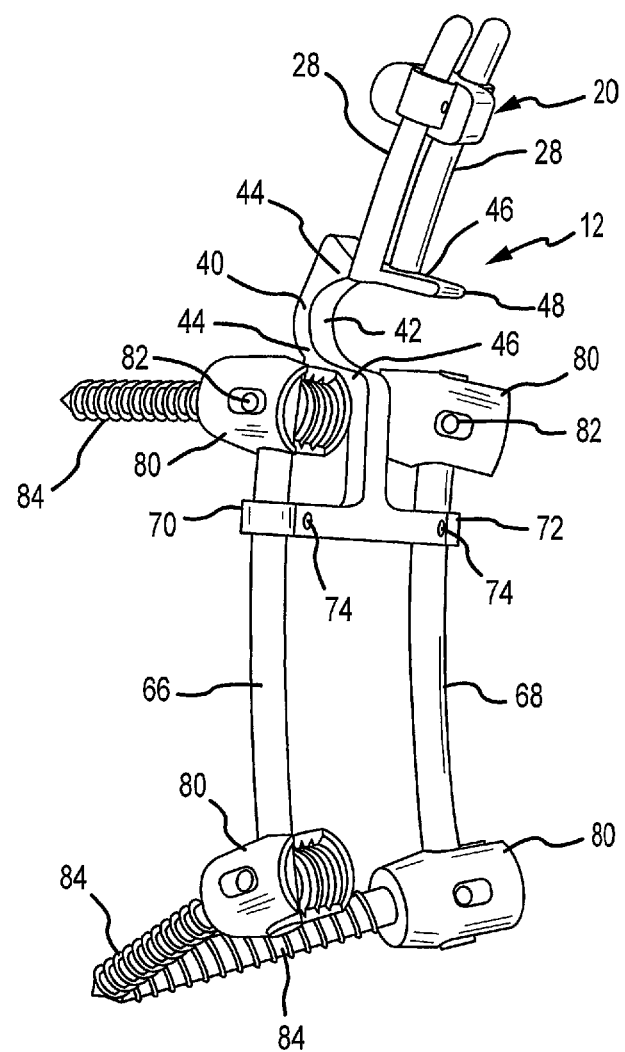
FIG. 2 is a side perspective view of a spinal stabilization system in accordance with an embodiment of the present invention.

Referring now to FIG. 1, a spinal stabilization system according to an embodiment of the present invention is shown generally at 10 (which for purposes of brevity will be referred to herein as "the system"). The system includes a first interlaminar member 12 adapted to be positioned between adjacent vertebra in a spinal column. As shown in greater detail in FIGS. 6 and 7, the interlaminar member 12 is shown positioned between a first vertebra 14 and a second adjacent vertebra 16 in a spinal column 18.

The system further includes a second interlaminar member 20 adapted to be positioned between the second vertebra 16 and a third vertebra 22 in the spinal column 18. While the system 10 of the embodiment of FIG. 1 is described with reference to two interlaminar support members, it is to be understood that a third, fourth or more interlaminar support members or components may be coupled to the system to permit stabilization or fixation of additional spinal segments in either or both directions along a patent's spinal column.

Both the first and second interlaminar members are operatively connected to a support structure shown generally at numeral 25 in FIG. 1. By way of example, in the embodiment shown, the support structure and the first interlaminar member are integrally formed from a single piece of material such as titanium or stainless steel suitable for use as a medical implant device. However, it is to be understood that other means for connecting the interlaminar device to the support structure such as hinges, pins, threaded fasteners and the like may also be used without departing from the scope of the invention.

The support structure 25 comprises a pair of support members or guide rods 28 secured to the first interlaminar support member 12 and extending in a direction upwardly therefrom substantially parallel to one another. In the embodiment shown, guide rods 28 are of an exemplary generally circular cross-sectional configuration. However, it is to be understood that other structured shapes such as oval square, hexagonal, and I-beam cross sections may also be used with equal efficiency.

Figure 3:
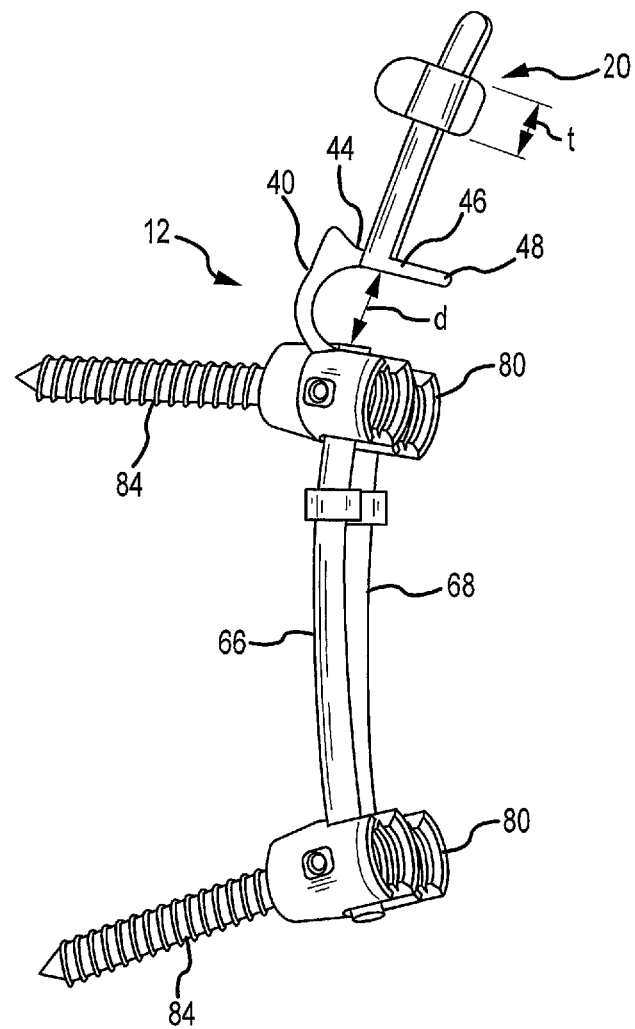
FIG. 3 is a side plan view of a spinal stabilization system in accordance with an embodiment of the present invention.
Figure 9:
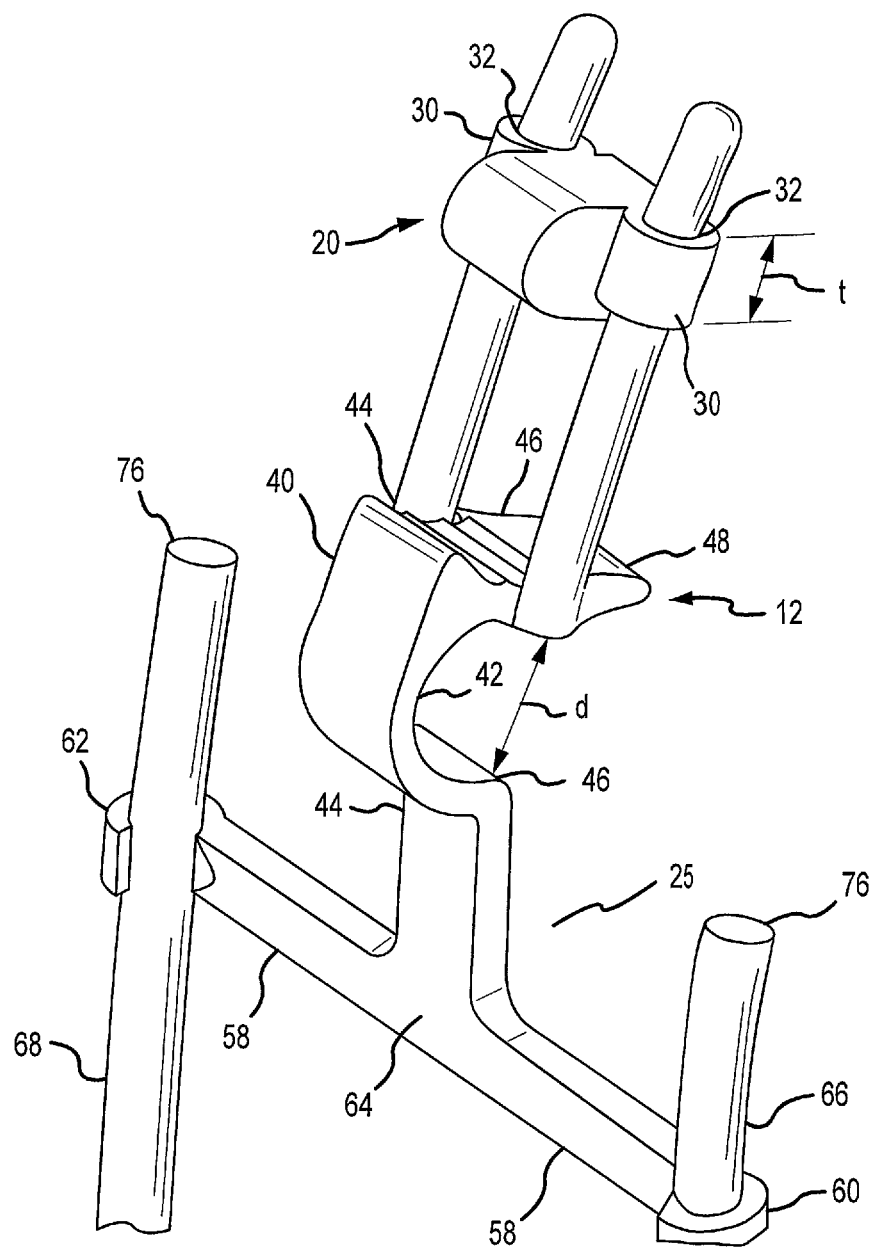
FIG. 9 is a rear perspective view of a portion of the spinal stabilization system shown in FIGS. 6, 7 and 8.
Figure 10:
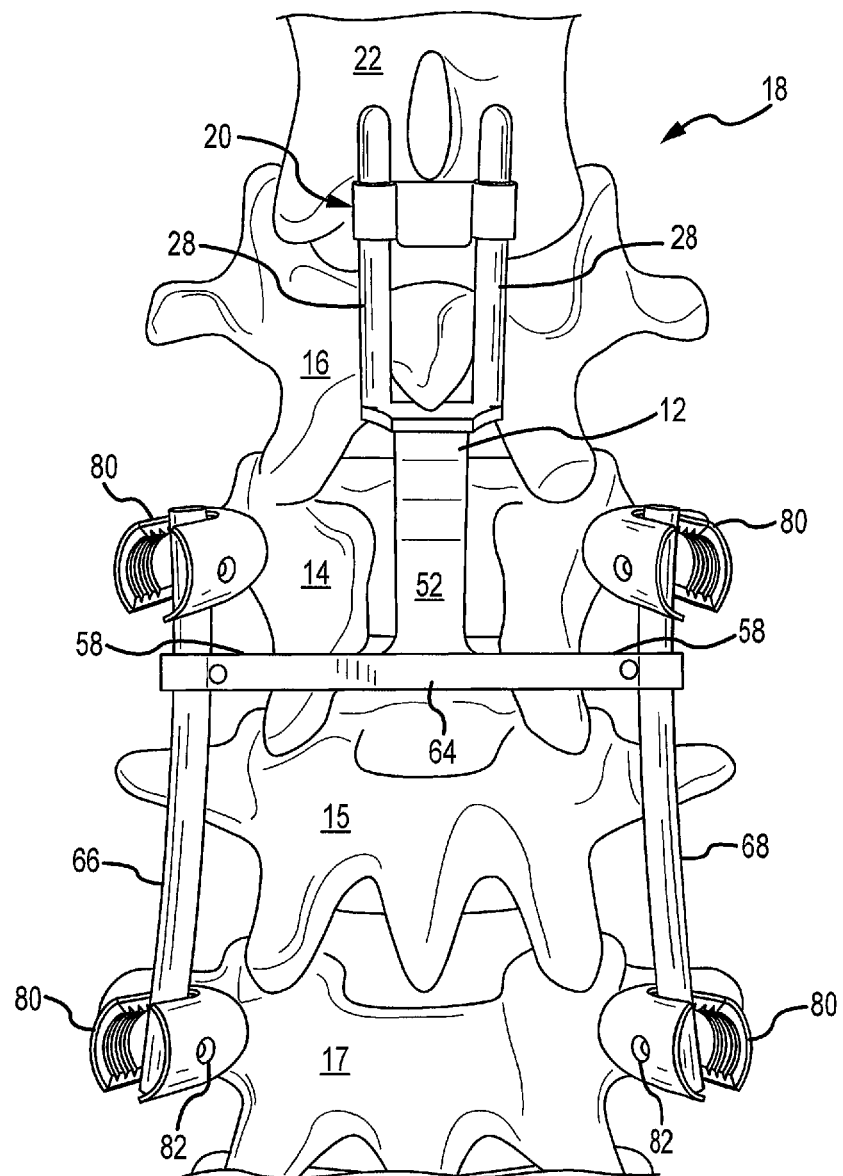
FIG. 10 is a front plan view of a spinal stabilization system in accordance with an embodiment of the present invention affixed to a spinal column.
Figure 11:
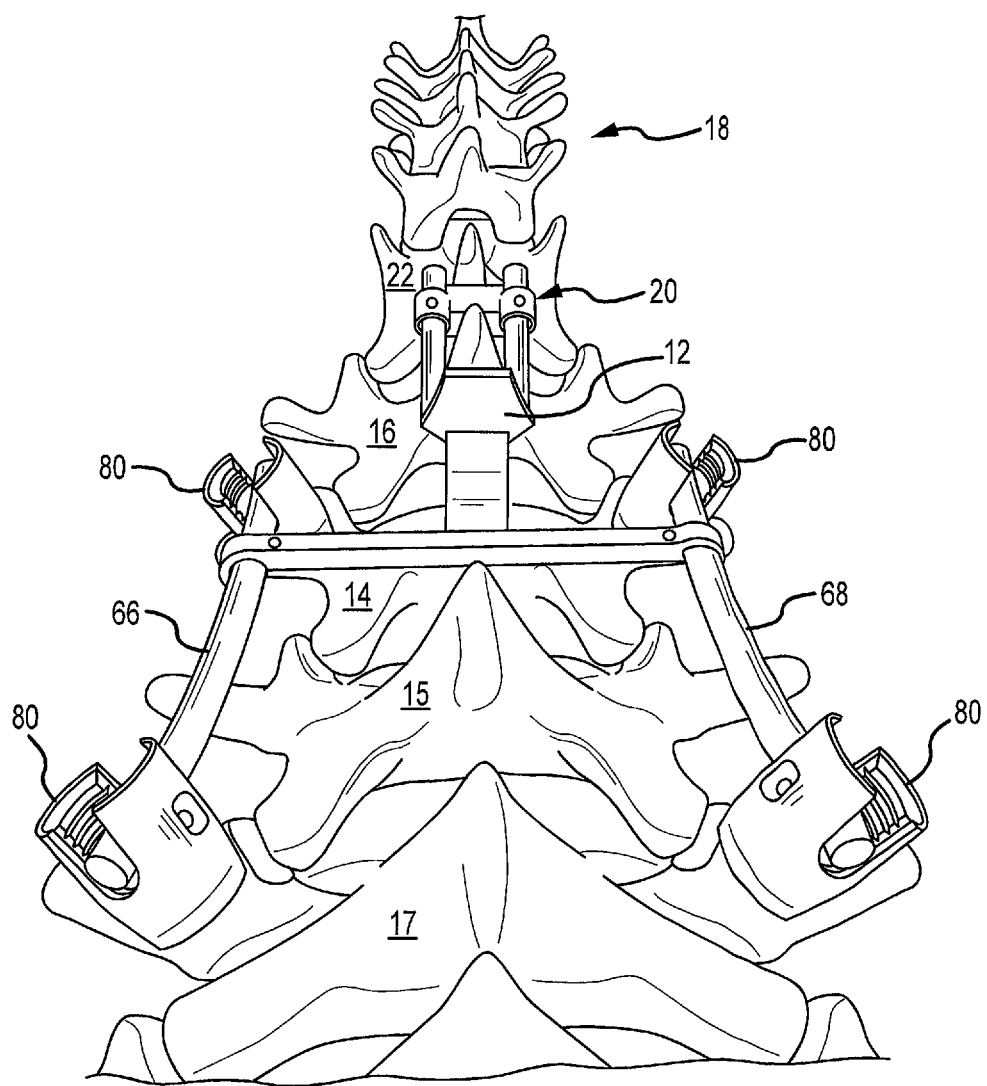
FIG. 11 is a bottom front perspective view of a spinal stabilization system in accordance with an embodiment of the present invention affixed to a spinal column.
Figure 12:
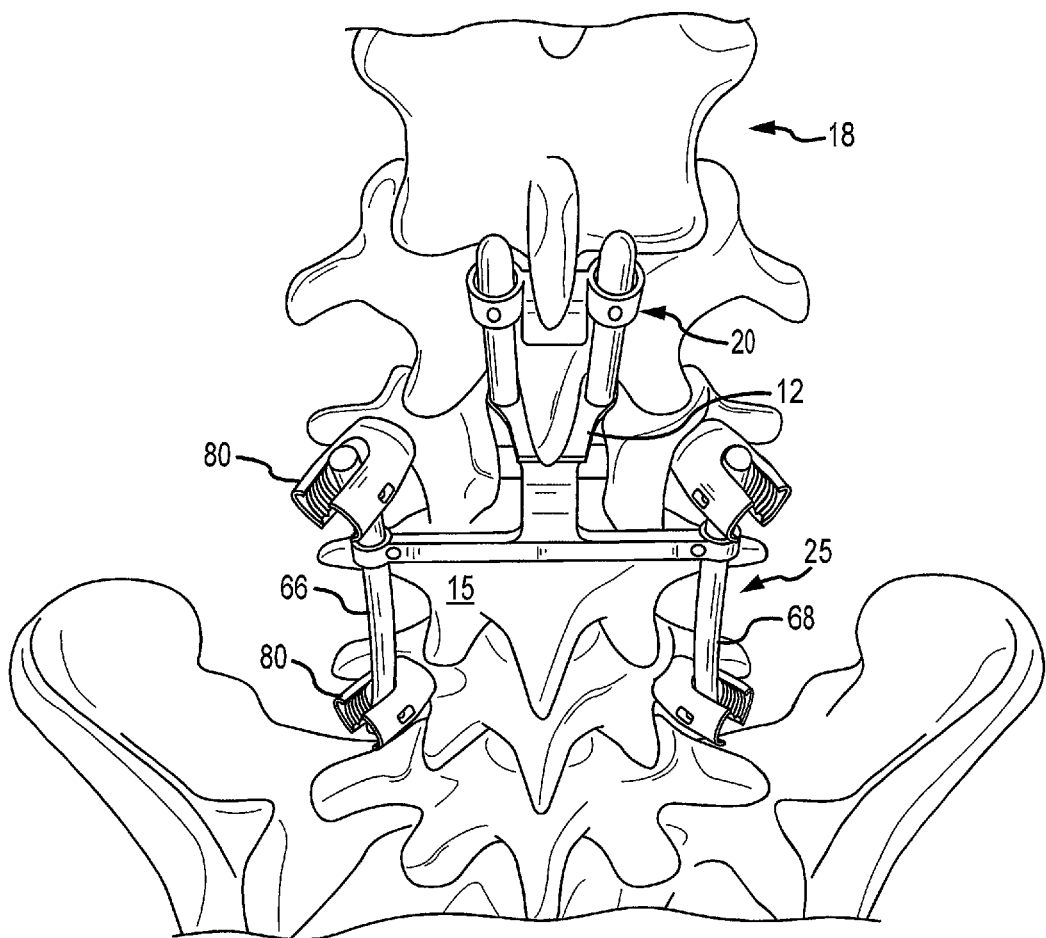
FIG. 12 is a top front perspective view of a spinal stabilization system in accordance with and embodiment of the present invention affixed to a spinal column.
Figure 13:
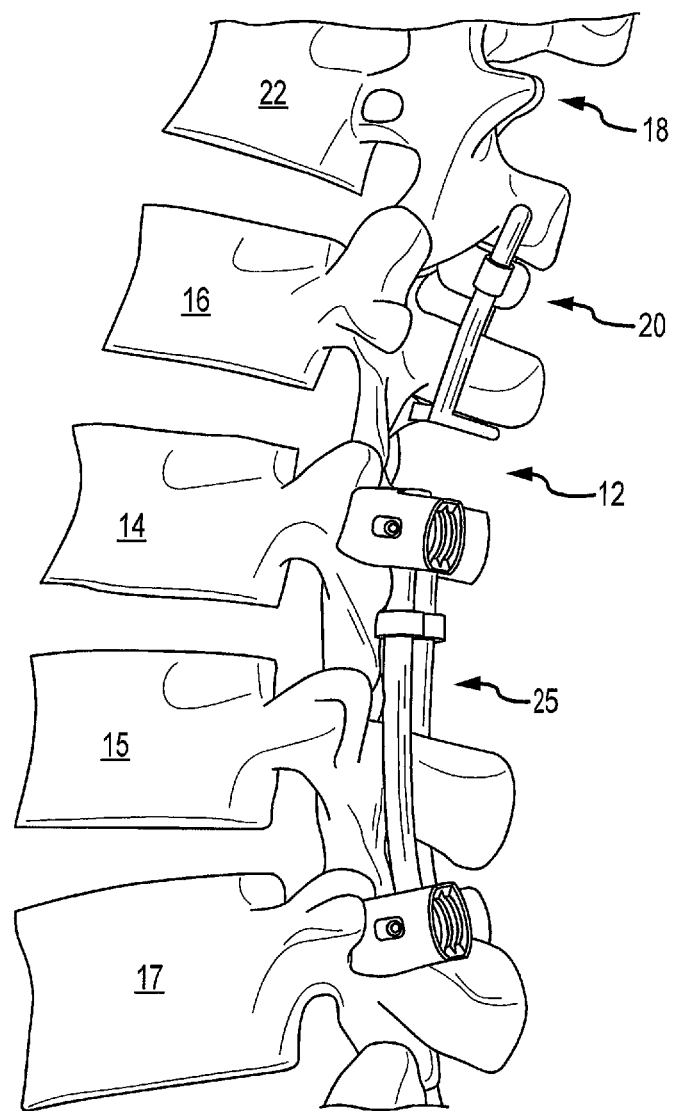
FIG. 13 is a side perspective view of a spinal stabilization system in accordance with an embodiment of the present invention affixed to a spinal column.

The second interlaminar member 20 includes a body portion 21 of a preselected thickness t, which is most clearly illustrated in FIGS. 3 and 9. Thickness t is selected based upon the spacing between the second and third vertebrae and may be smaller in size than the spacing to allow for flexion or extension of the spinal column 18. Alternatively, it may be sized for interference fit between the laminae/spinous processes. The body portion 20 may take many variations in size, scope, and physical properties such as hardness, flexibility, and so forth, depending upon the patient's anatomical structure and the problems being addressed.

Figure 4:
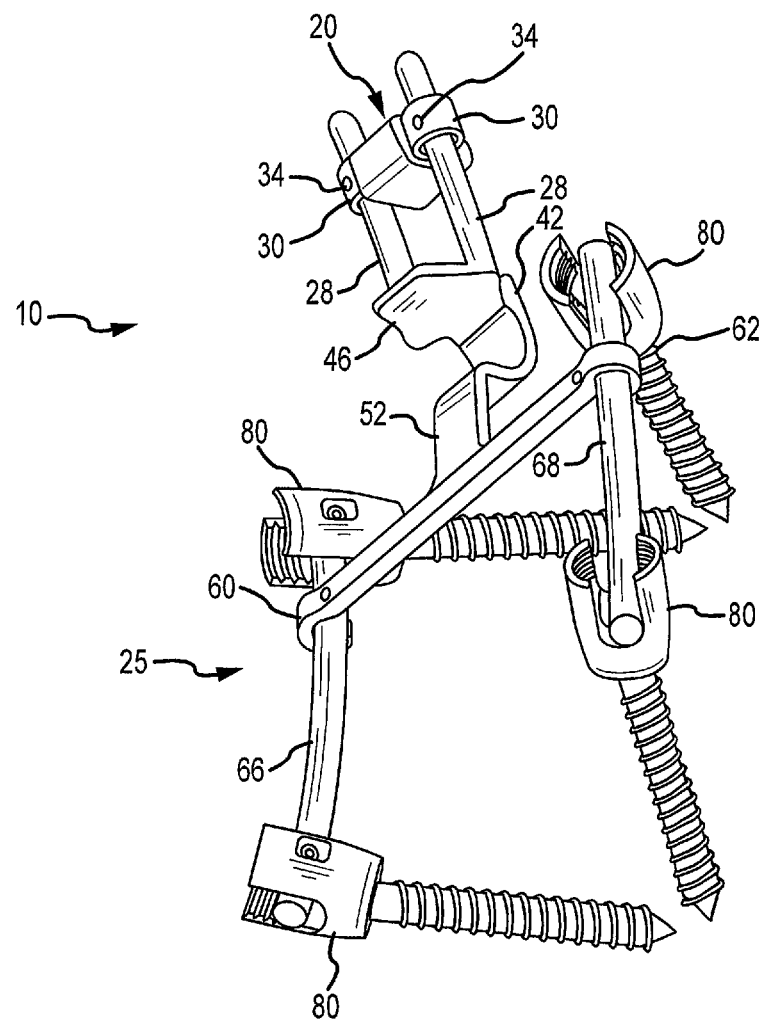
FIG. 4 is a bottom perspective view of a spinal stabilization system in accordance with an embodiment of the present invention.
Figure 5:
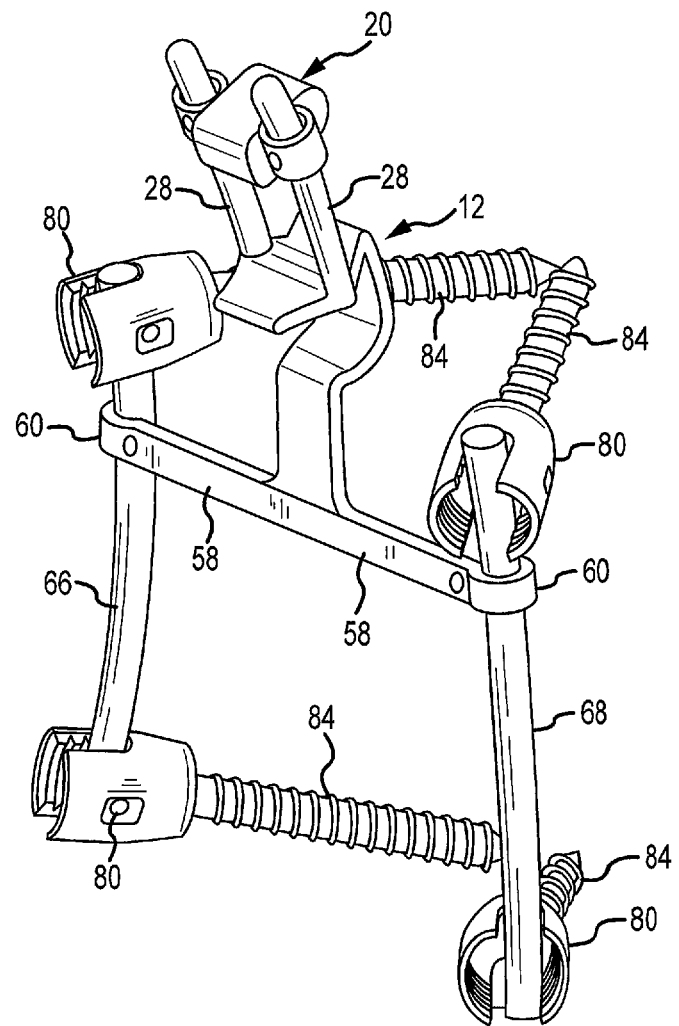
FIG. 5 is a top perspective view of a spinal stabilization system in accordance with an embodiment of the present invention.

The body portion 21 further includes a pair of oppositely positioned ears 30 extending laterally outwardly from the body portion in opposing directions, each of the ears containing an aperture 32 structured and arranged to slideably receive one of the support members or guide rods 28. As will be discussed in greater detail below, the second interlaminar member is movably supported by upwardly extending support members or guide rods, and the position of the second interlaminar member 20 relative to the first interlaminar member 12 may be adjusted depending upon the dimensions of the specific spinal column on which the system is installed and the range of motion desired. Once the position of the second interlaminar member 20 has been selected, it is locked in place by a pair of set screws or other suitable fastening means 34 extending through each of the ears 30 and adapted to releasably engage the respective guide rod extending therethrough, as shown in FIG. 1 and in greater detail in FIG. 4.

Referring now to FIGS. 2, 3, 7 and 8, the first interlaminar member 12 is depicted in greater detail. The first interlaminar member comprises a body 40 defined by an elastic midsection 42, two spaced apart end portions 44, and a pair of juxtaposed legs 46, each leg extending substantially parallel to one another from one of the respective ends in a direction generally outwardly away from the spinal column 18 (FIG. 7) and spaced apart a preselected distance d. Distance d is determined by the size of the first interlaminar member 12, which is, in turn, may be selected based upon the spacing between the first and second vertebrae 14 and 16, respectively. Depending upon the situation, the first interlaminar member may be intended to fuse the first and second vertebrae, or it may be intended to permit limited motion therebetween while at the same time maintaining the stability of vertebra 16 relative to vertebra 14. Accordingly, it may be sized to be a tight fit, and the elastic properties of the body 40 act as a spring or shock absorber in the interface between the two vertebrae. In the embodiment shown in the above-referenced figures, the elastic midsection 42 of the body 40 is U-shaped. However, other shapes or configurations, by way of example, a V-shape, a W-shape or other function configurations may also be used effectively. Further, the uppermost one of the legs 46 is longer that the lower one of the legs, thereby forming a handle 48 which may be used to insert and position the system during surgery and also to increase the contact surface area with the adjacent spinous process. As noted above, depending upon the problem being addressed, the U-shaped body may be rigid—or flexible.

Referring again to FIG. 1, the support structure 25 further includes a T-shaped frame member 50 operatively connected to the first and second interlaminar members 12 and 20 and which extends generally downwardly therefrom in a direction substantially parallel to the spinal column 18. The T-shaped frame member comprises an elongate body 52 having first and second end portions 54, 56, the first end portion being operatively connected to the first interlaminar member 12, and the second end portion to an elongate cross member 58. The cross member has first and second end portions 60, 62 and a midpoint 64 and is structured and arranged to be connected to the second end portion 56 of the body 52 at approximately the midpoint 64. Each of the ends 60, 62 of the cross member 58 are adapted to receive and adjustably secure first and second support members 66 and 68, respectively. In the embodiment shown, each of the end portions 60, 62 have an aperture 70, 72 formed therein respectively for receiving one of the support members 66, 68, each of which may be held in a preselected position by a set screw 74 or other interconnection coupling means as is known in the art.

In the embodiment shown, by way of example only and not of limitation, the support members are in the form of spinal or guide rods 66, 68, each guide rod having an upper end 76 and a lower end 78. Each of the upper and lower ends of the support members 66, 68 has a securing device 80 slideably positioned thereon and adapted to be secured thereto by means of set screws 82. By way of example, each of the securing devices 80 is adapted to receive a pedicle screw 84, each pedicle screw being structured and arranged to be secured to one of the vertebra of the spinal column 18.

Figure 6:
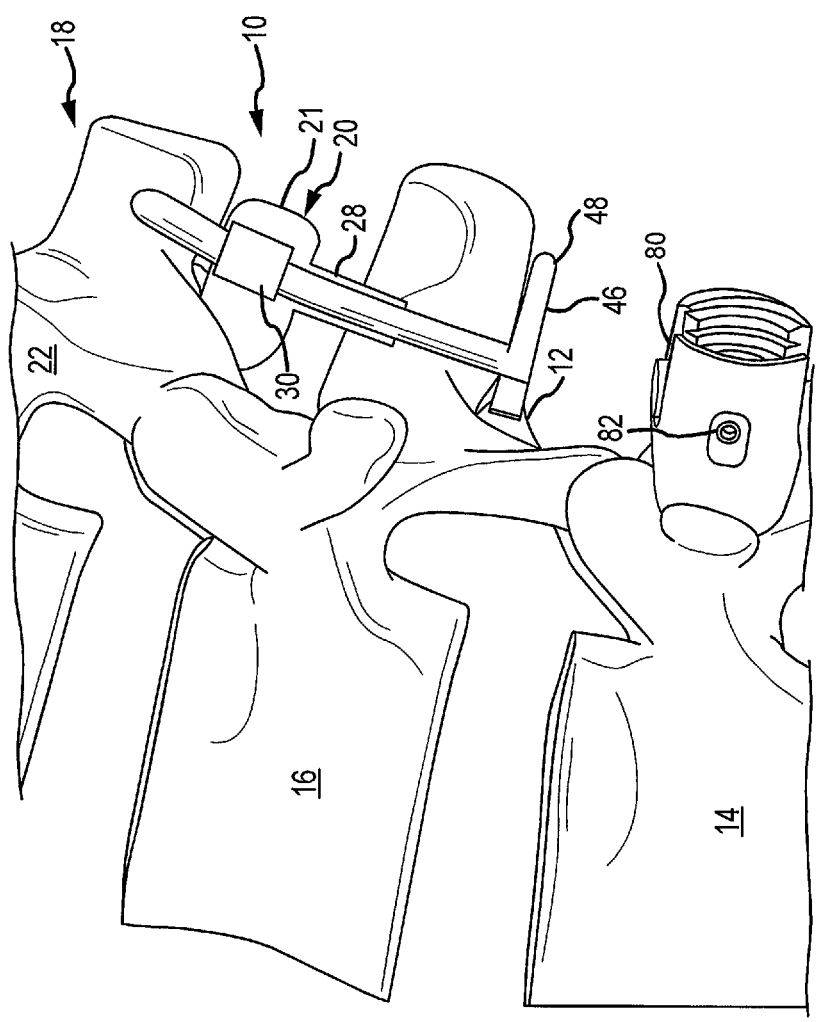
FIG. 6 is an enlarged side plan view of a portion of the spinal stabilization system of the present invention shown in FIG. 3 showing an upper portion of the stabilization system affixed to a spinal column.
Figure 7:
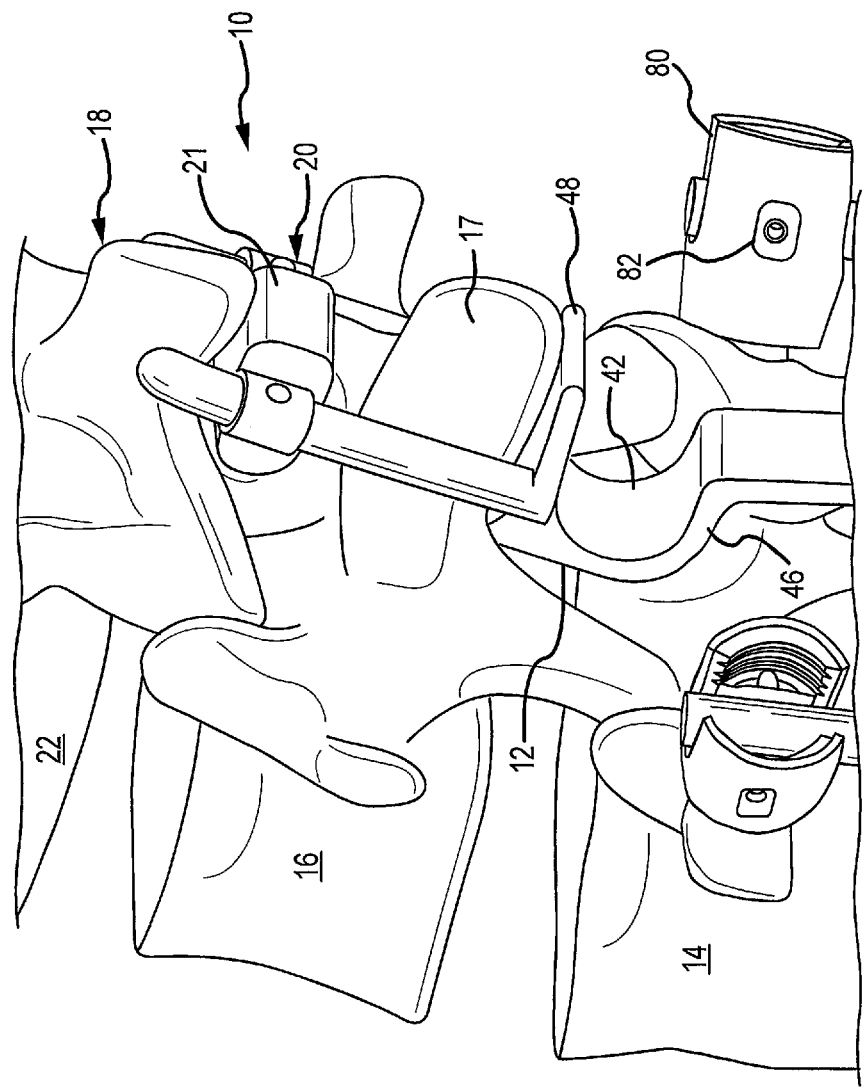
FIG. 7 is a side perspective view of a portion of the spinal stabilization system shown in FIG. 6.
Figure 8:
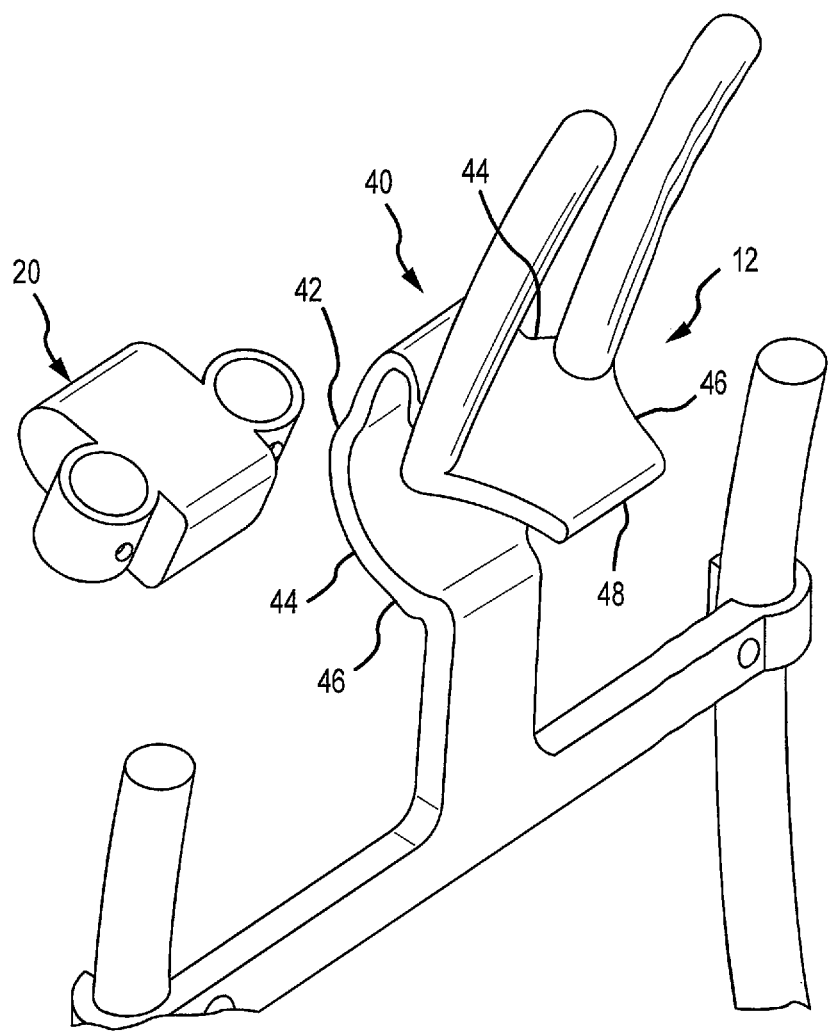
FIG. 8 is an exploded front perspective view of a portion of the spinal stabilization system shown in FIGS. 6 and 7.

The installation and operation of the spinal support system 10 of the present invention are illustrated in greater detail in FIGS. 6, 7 and 10-13. The system advantageously may be installed where other spinal fixation or fusion devices or similar medical apparatus are already in place to add stability to the spinal column above and below the installation point, to control flexion, extension, axial compression, and/or rotational movement of the spine or selected vertebrae with respect to one another, and to prevent impingement of adjacent vertebrae, spinal processes, pedicle screws and medical hardware on one another. By way of example, as best shown in FIGS. 6 and 7, a surgeon may insert the system 25 into the space between adjacent vertebrae 14 and 16 by gripping handle 48 and making the insertion. The tight fitting U-shaped body 40 not only serves to control any motion between the adjacent vertebrae or even eliminate it entirely, thereby effectively stabilizing or fixating the vertebrae, but also serves as a dampening cushion or spring device by virtue of the spring-like elasticity of the body 40 translated to the vertebrae via legs 46. Thereafter, the second interlaminar member 20 may be selectively positioned intermediate vertebra 16 and vertebra 22 to permit flexion on a forward direction but to limit extension in the rearward direction and to limit compression of the spinal segment, thereby imparting enhanced stability to the spinal column above the fused vertebrae.

In the embodiment of FIG. 7, the body 40 of interlaminar member 12 is formed integrally with those portions of the system 10 above and below it, it is to be understood that it could comprise a separate element of the system and be adjustably moveable inwardly by rack and pinion gearing or ratcheting devices to provide a precise fit in the interlaminar space between vertebrae 14 and 16 positioned as closely to the spinal canal as safety considerations permit. The upper leg and handle 48 extending therefrom may be longer than the lower leg 46, whereby the contact surface area engaging the spinal process 17 positioned there above, is enlarged. This structure effectively distributes the associated forces over a larger surface contact area, thereby reducing the risk of fracture of the spinal process.

In a similar manner, support structure 25, via the T-shaped frame member 50 and support members or guide rods 66 and 68, provides support to the portion of the spinal column located below the fused vertebrae 14 and 16. As shown in FIGS. 10-13, the securing devices 80, which are coupled to heads (shown shown) of pedicle screws 84, may be positioned in first vertebra 14 and in either vertebra 15 immediately adjacent to vertebra 14, and/or at a lower level as shown by vertebra 17, thus extending the stabilizing effect of the novel support system of the present invention to multiple levels in the spinal column 18. More than one level may be addressed simply by lengthening the rods 66 and 68 and slideably positioning multiple securing devices 80 thereon for selective positioning along the spinal column.

In one aspect of the present invention, elongate body 52 may be comprised of multiple pieces. For example, one or more linear racks may be configured in operable relation with gear mechanisms, thereby forming a ratchet device (not shown), in order to extend the distance between first and second end portions 54 and 56 thereby permitting a surgeon during the course of the surgical procedure to adjust and align components of the implant in relation to the patient's bony anatomy and subsequently securing them in place. For example, a ratchet mechanism configuration may permit the surgeon to progressively extend elements of the implant to better oppose a lamina, e.g., after 60/62 are secured to 66/68.

Figure 14C:
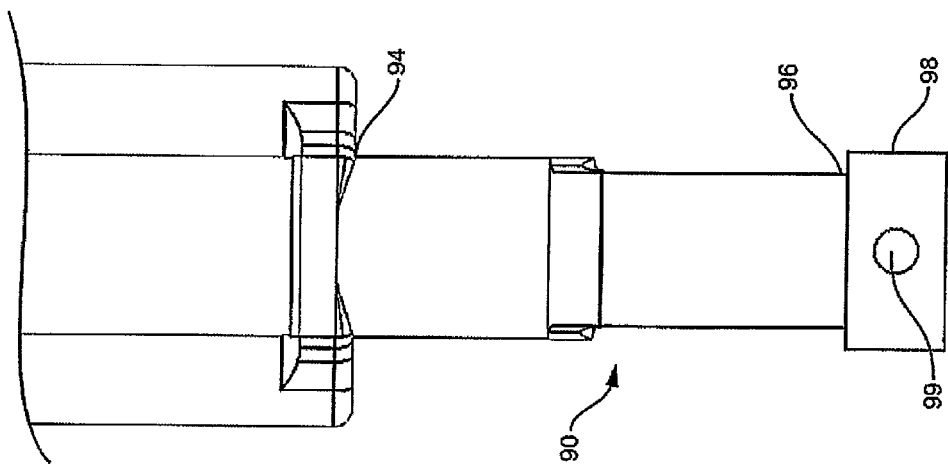
FIG. 14(C) is a front plan view of the interlaminar portion of a spinal stabilization system shown in FIGS. 14(A) and 14(B)
Figure 14B:
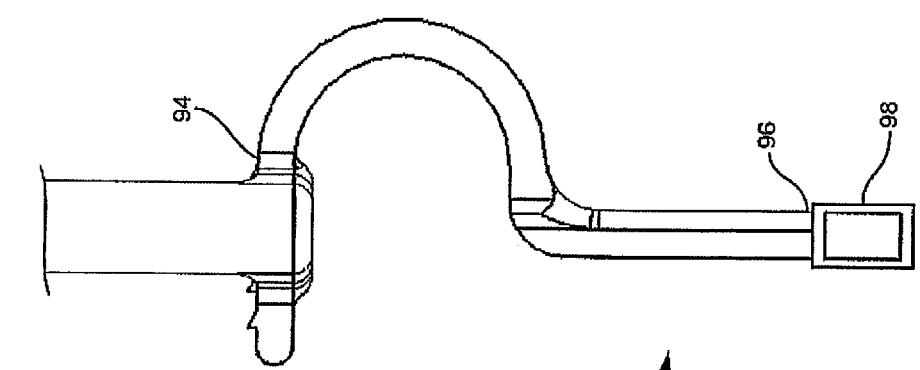
FIG. 14(B) is a side plan view of the interlaminar portion of a spinal stabilization system shown in FIG. 14(A)
Figure 14A:
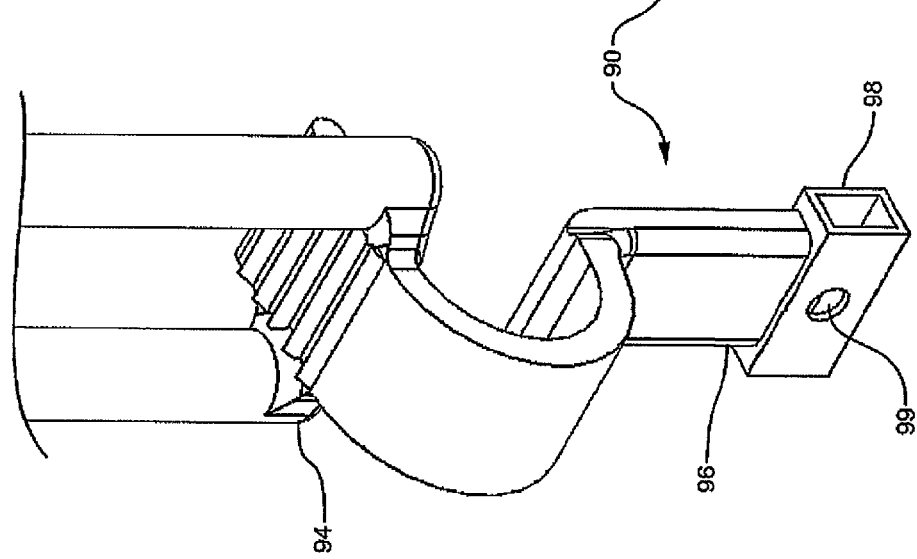
FIG. 14(A) is a rear side perspective view of an interlaminar portion of a spinal stabilization system in accordance with an embodiment.

In another aspect, the cross member midpoint 64 may be configured to be adjustably (e.g., pivotably or translatably) connected or secured to the second end portion 56 of the body 52 at approximately the midpoint 64 in order to allow a surgeon during the course of the surgical procedure to adjust and align components of the implant in relation to the patient's bony anatomy and in relation to support members 66 and 68. By way of example and not of limitation, FIGS. 14(A)-(C) illustrate an interlaminar member 90 adapted to be positioned between adjacent vertebra in a spinal column. The interlaminar member includes a body portion 92 having a first end portion 94 and a second end portion 96, the second end portion being structured and arranged to adjustably receive the elongate cross member 58 (FIG. 1) in order to allow a surgeon to further adjust and align components of the implant in relation to the patient's bony anatomy. By way of example and not of limitation, the second end portion 96 may include an open-ended aperture or channel 98 for receiving and selectively positioning the elongate member 58 and a means for securing the elongate member in a desired position along a patient's spinal process. The elongate cross member 58 may have a cross-sectional configuration which is complementary to the cross section of the channel or aperture, be it rectangular, hexagonal, circular, or another shape.

In the embodiment shown, the securing means includes an aperture 99 formed transversely in the channel 98 and adapted to receive a locking mechanism, e.g., one or more set screws, clamps, pins, pegs and the like such that when the locking mechanism is engaged, the second end portion 96 is in a fixed relation to the elongate cross member 58. This configuration may permit translational and/or rotational movement(s) between the second end portion and the elongate cross member to permit alignment of the various elements of the spinal stabilization system 10 (FIG. 1) with a patient's unique anatomical structure, and, following alignment, the locking mechanism may be engaged to fix the relative position of the system components with respect to one another and with respect to the spinal process.

According to particular embodiments, interlaminar member 20 may be configured to permit connection to guide rods 28 via an approach that is substantially perpendicular to the longitudinal axis of guide rods 28. In other words, after the other components of the system have been implanted via a posterior approach to the posterior aspect of the spine the interlaminar member 20 may follow a generally similar approach trajectory and then secured to the guide rods 28 with, e.g., set screws in a similar manner to the engagement between the ends 60, 62 of the cross member 58 and first and second support members 66 and 68. Furthermore, in another aspect, an interlaminar member 20 may be used alone (and may alternatively be configured to be similar to the U-shaped body 40) and may be directly engaged with a first and second support members 66 and 68 and positioned between the lamina and spinous processes of the spine.

Figure 15:
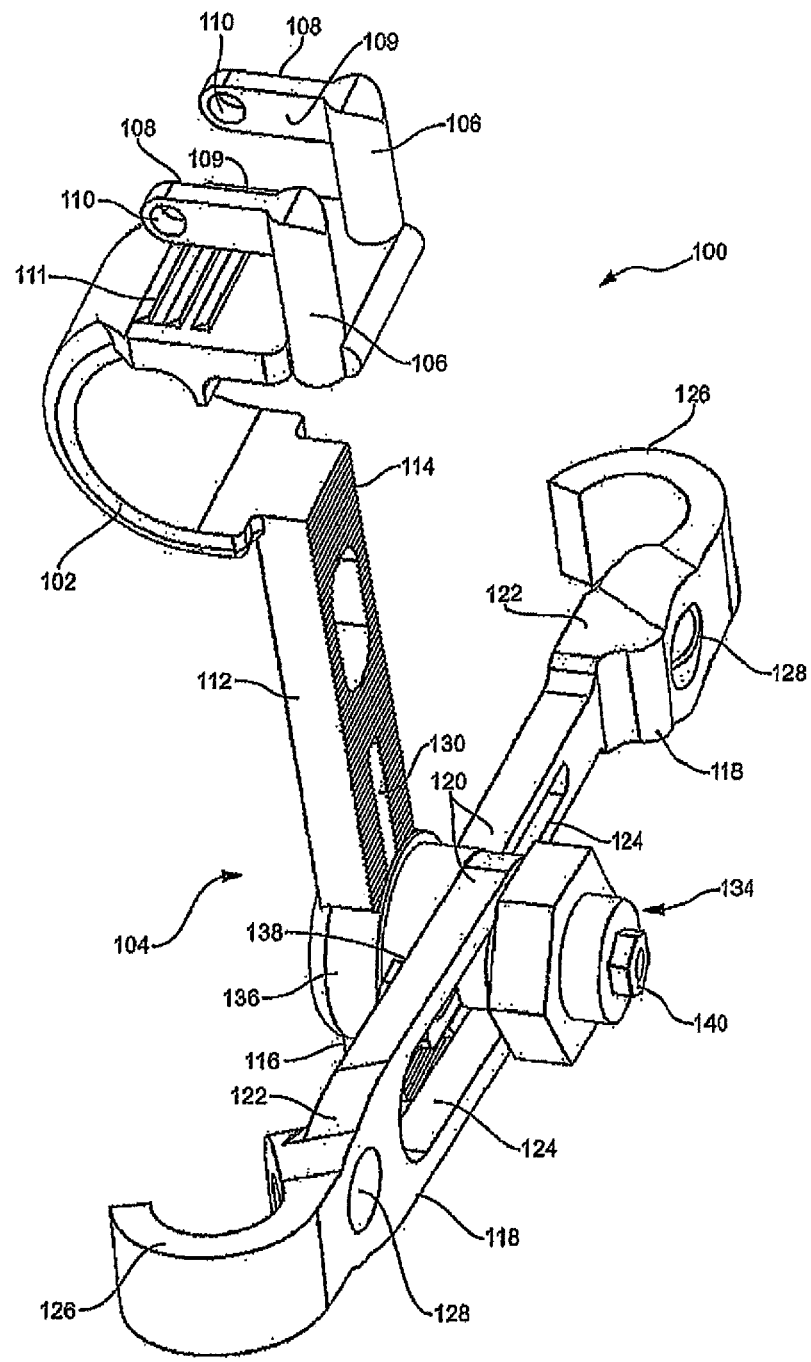
FIG. 15 is a top front perspective view of a spinal stabilization system in accordance with an embodiment of the present invention.

In yet another aspect, each of the ends 60, 62 of the cross member 58 may be configured to permit a degree of adjustability (e.g., pivotably or translatably) to receive and adjustably secure first and second support members 66 and 68 respectively. For example any transverse connector or cross-link variable adjustment mechanism or fastener known in the art may be employed to accomplish the desired fixation between the ends 60, 62 of the cross member 58 and first and second support members 66 and 68. A spinal stabilization system 100 incorporating these features is illustrated generally at 100 in FIGS. 15 and 16.

System 100 includes an interlaminar member 102 of substantially the same configuration as the interlaminar member 12 described above in the embodiment of FIG. 1. Interlaminar member 102 is adapted to be positioned between adjacent vertebra in a spinal column and is operatively connected to a support structure shown generally at numeral 104. As described hereinabove with respect to the embodiment of FIG. 1, in the embodiment shown in FIGS. 15 and 16, the support structure and the interlaminar member are integrally formed from a single piece of material such as titanium or stainless steel suitable for use as a medical implant device. However, it is to be understood that other means for connecting the interlaminar device to the support structure such as hinges, pins, threaded fasteners and the like may also be used without departing from the scope of the invention.

The support structure 104 comprises a pair of spaced-apart support members or guide rods 106 secured to the interlaminar member 102 and extending in a direction upwardly therefrom substantially parallel to one another. Each of the guide rods 106 includes an ear or bracket element 108 extending generally outwardly therefrom in a direction either toward or away from the spinal column (not shown) and includes an aperture 110 formed therein adapted to receive a securing device such as a pin or a threaded fastener for attaching the system to a vertebra.

While not shown in the drawings, it is to be understood that the guide rods 106 and ear or bracelet elements 108 connected thereto may be adjustably moveable by a ratcheting or other suitable mechanism in a direction towards each other, thereby applying a clamping force to a spinal process positioned therebetween. Each of an inner surfaced or face 109 may also include a rough textured finish or have sharp extensions, or "spikes" (not shown) formed thereon and extending outwardly therefrom which may imbed themselves in the surface of a spinal process, thereby preventing slippage.

In a similar manner, ridges 111 formed on an upper surface 113 of number 102 also engage the bony structure of a vertebra, thereby enhancing the engagement of the system 100 with the spinal column.

The support structure 104 further includes an elongate body 112 having first and second end portions 114, 116, the first end portion being operatively connected to interlaminar member 102; the second end portion being operatively connected to a pair of elongate cross members 118 adjustably positioned in overlapping juxtaposition with respect to one another and the second end portion 116 of the support structure, as will be described hereinbelow in greater detail. Each of the cross members has first and second end portions 120, 122, each of the first end portions 120 having a longitudinally extending aperture or slot 124 formed therein, and each of the second end portions includes a connector 126 adapted to receive and adjustably secure a support member of the system, such as a guide rod 66, 68 as illustrated in FIG. 1, by a locking member 128. Locking member 128 may be in the form of a set screw, a pin, a clamp or other such suitable locking means as is known generally in the art.

Figure 16:
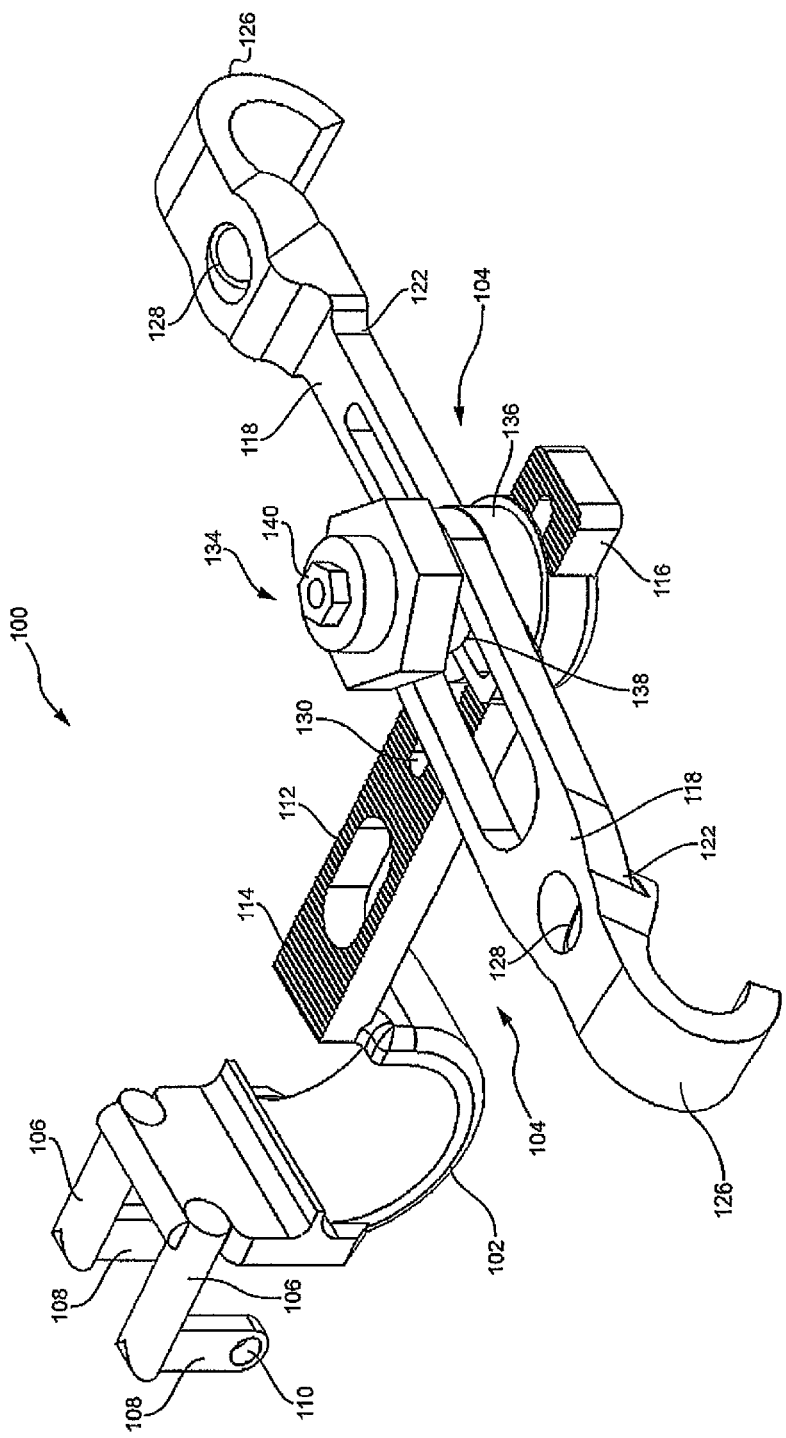
FIG. 16 is a bottom front perspective view of the spinal stabilization system shown in FIG. 15.

As shown in greater detail in FIG. 16, the second end portion 116 has an elongate longitudinally extending aperture or slot 130 formed therein structured and arranged to receive securing means shown generally at 134 for adjustably securing elongate cross members 118 thereto. By way of example and not of limitation, securing means 134 includes a collar 136 slideably positioned on end 116 and having a generally transversely extending aperture 138 formed therein for receiving a first end portion 120 of an elongate cross member 118. A fastener, by way of example a bolt 140, extends through each of the slots 124 in the elongate cross members 118 placed in overlapping slideable juxtaposition with respect to one another, the slot 130 in the second end 116 of the support structure 104 and into an aperture, by way of example a threaded aperture (not shown) which is formed in the collar 136. This configuration permits translational and/or rotational movement and adjustment in the generally caudal or cephalad directions of both the first and second ends 120, 122 of the cross members 118 with respect to the elongate body 112, thereby permitting precise alignment of the interlaminar member 102 with a lamina and spinal process. Thereafter, the locking mechanism is engaged to fix the elements of the system in position with respect to one another and the patient's spine. While not shown in the figures, a second locking mechanism or stop such as a pin, strap, a band, a fastener, a clamp, and the like, as is known in the art, may also be connected to the elongate cross members 118 after they and the other elements of the system are aligned and fastener 140 is tightened to prevent movement of the elongate cross members relative to one another in response to loading transmitted thereto via the elongate body 112. This would be of particular concern in the event that the securing means 134 would loosen after installation.

Figure 17A:
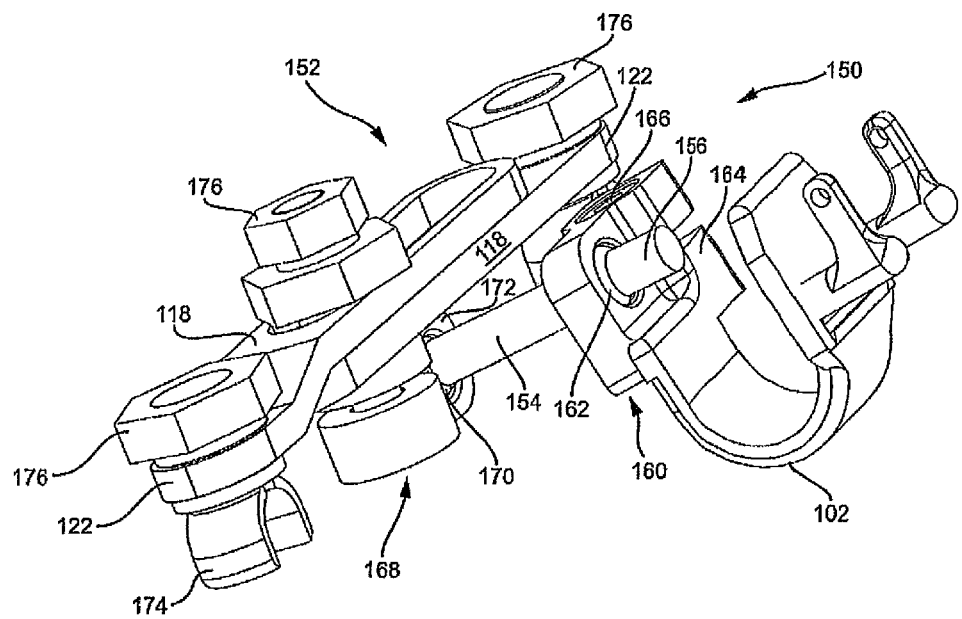
FIG. 17(A) is a top front view of a spinal stabilization system in accordance with an embodiment of the present invention.
Figure 17B:
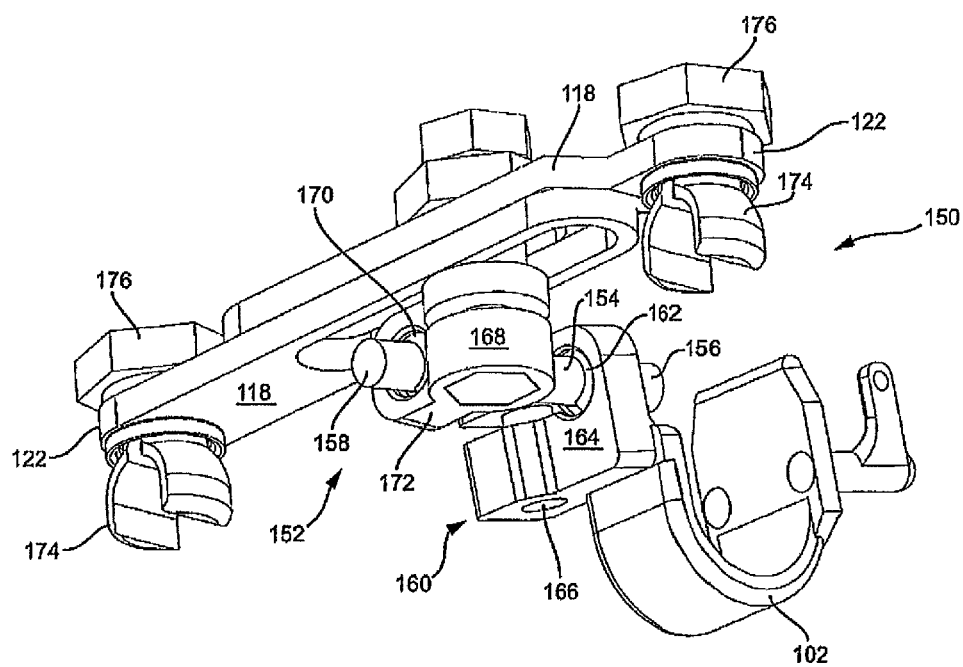
FIG. 17(B) is a bottom rear perspective view of the spinal stabilization system shown in FIG. 17(A)
Figure 18:
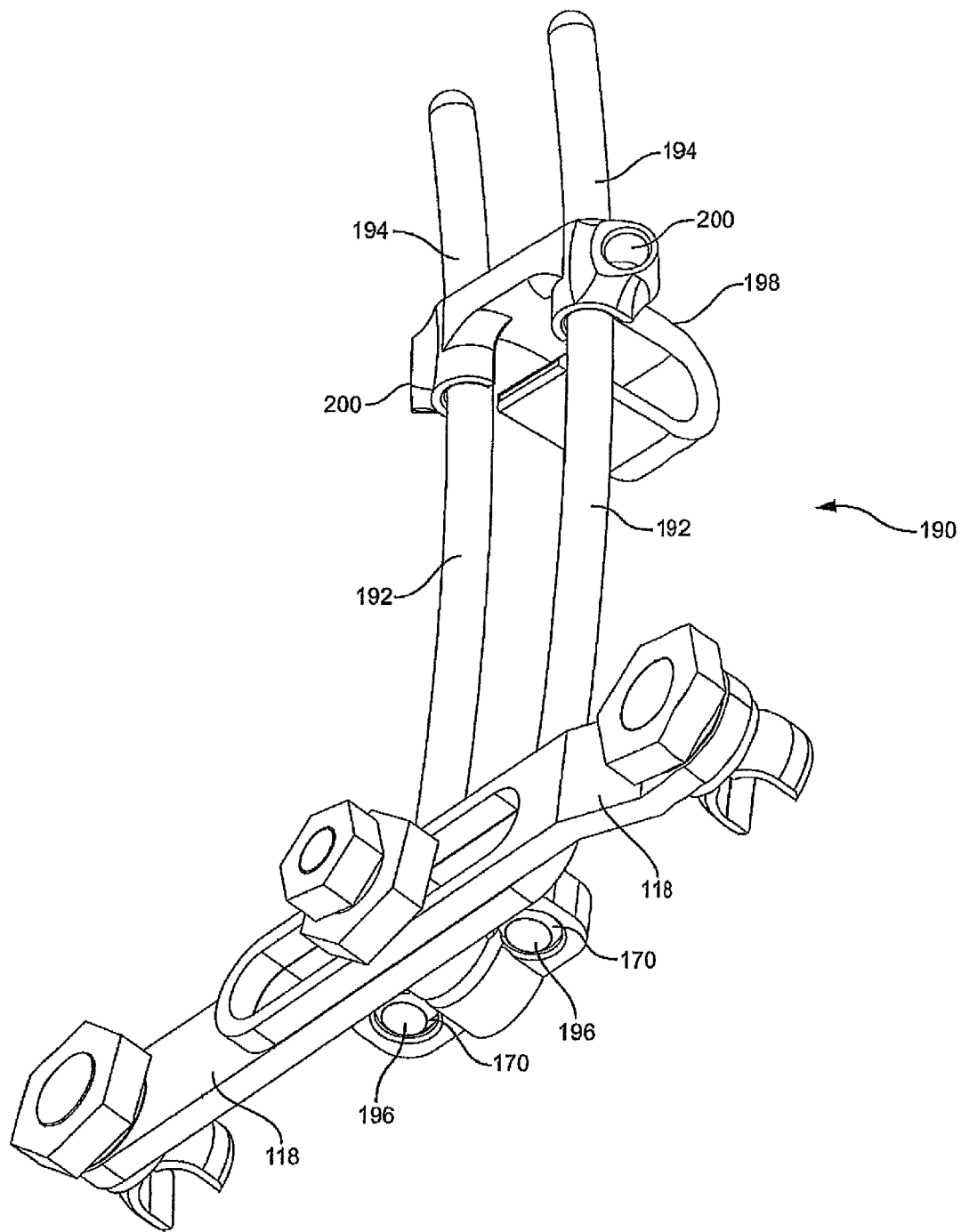
FIG. 18 is a bottom front perspective view of a spinal stabilization system in accordance with an embodiment of the present invention.
Figure 20:
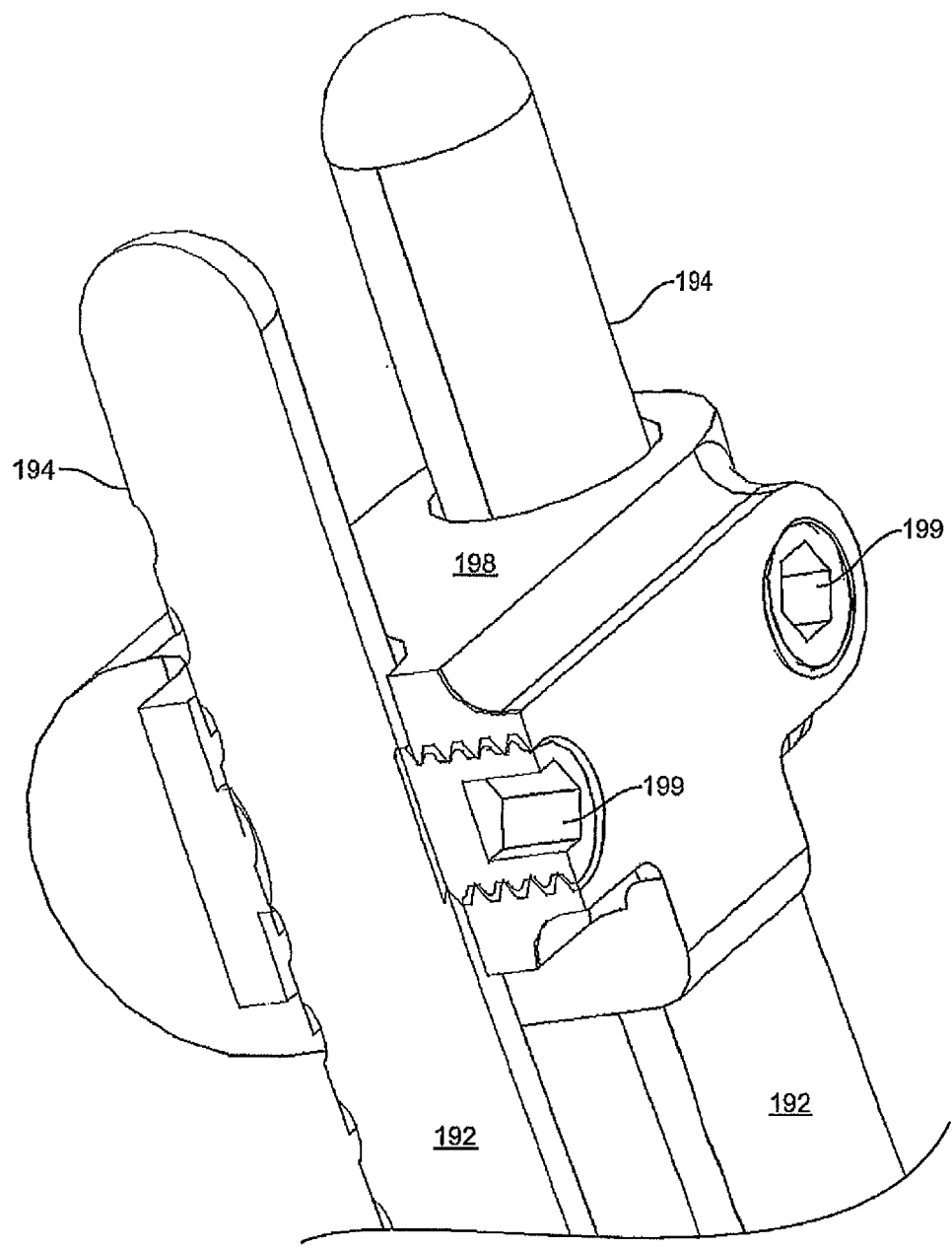
FIG. 20 is a partial sectional side perspective view of portions of the spinal stabilization system shown in FIG. 1.

Referring now to FIGS. 17(A) and (B), an embodiment 150 of a spinal stabilization system of the present invention is illustrated which includes a support structure 152 having an elongate body in the form of a rod or dowel 154 having first and second end portions 156, 158, the first end portion being operatively connected to interlaminar member 102; the second end portion being operatively connected to a pair of elongate cross members 118 adjustably positioned in overlapping juxtaposition with respect to one another and the second end portion 158 of the support structure, as described above with respect to the embodiment of FIGS. 15 and 16. However, in the embodiment of FIG. 17, a securing means 160 is provided in the form of a spherical or tubular collet 162 received over the first end portion 156 and secured thereto by a collar 164 and setscrew 166 or other suitable means of applying a compressive restraining force to the collet 162. The securing means 160 provides both translational and rotational movement of the interlaminar member 102 with respect to the support system 152, thereby permitting very precise alignment of the interlaminar member with a lamina and spinal process.

Figure 24:
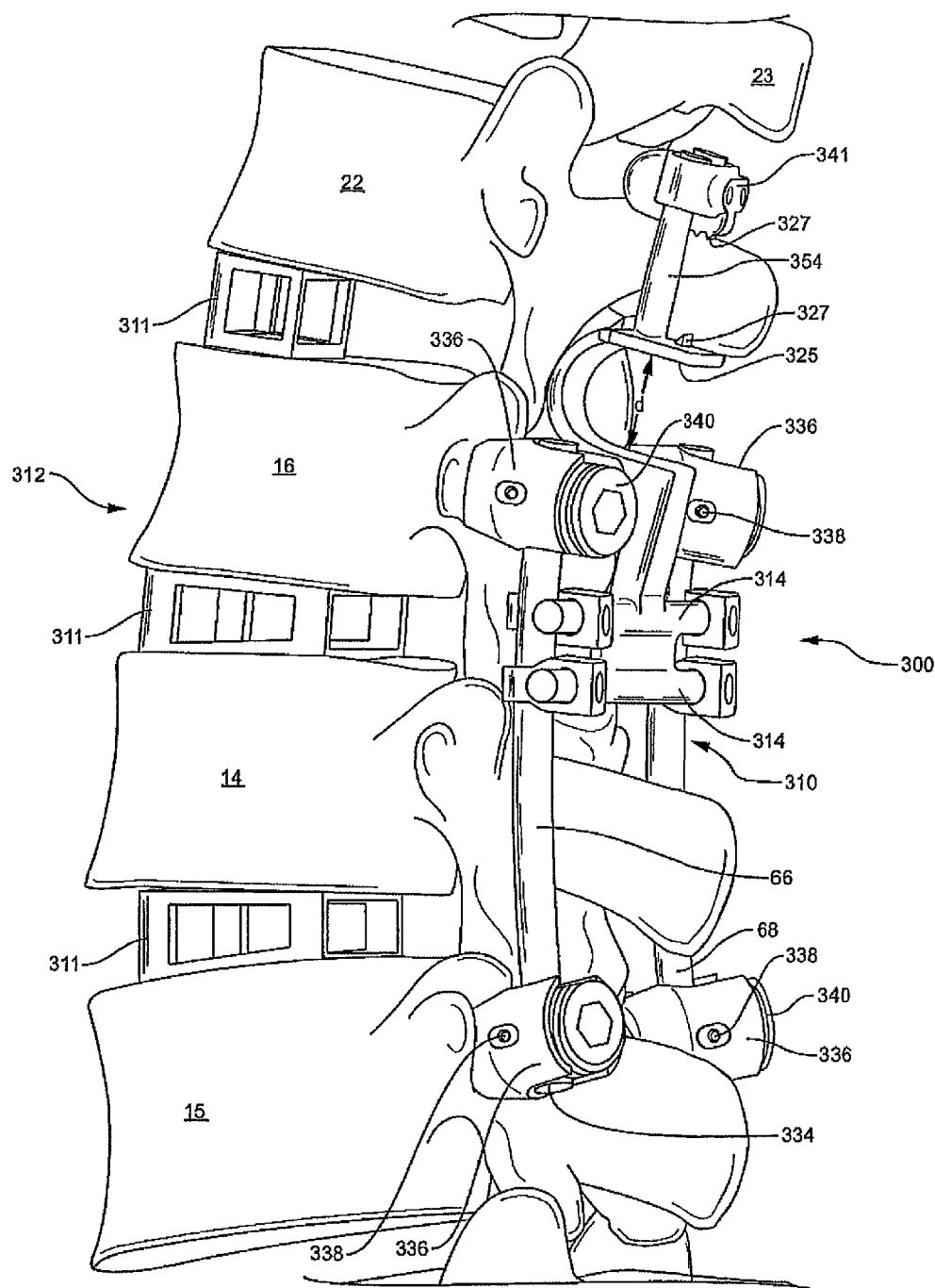
FIG. 24 is a side perspective view of a spinal stabilization system a spinal stabilization system in accordance with an embodiment of the present invention shown affixed to a spinal column.

A second similar securing means 168 having a spherical or tubular collet 170 received over the second end portion 158 of rod 154 and secured thereto by a collar 172 and setscrew or other suitable compressive securing means (not shown) applies a compressive restraining force to the collet 162. In the manner described above with respect to the collet and securing means at the first end 156, the collet 170 provides both translational and rotational movement of the overlapping elongate cross members 118 with respect to the rod 154 and interlaminar member 102, thereby assisting in establishing very precise alignment of the interlaminar member with a lamina and spinal process. In the embodiment shown, collets 170 are mounted on collar 172 of securing means 168. However, for enhanced stability, the collets could also be mounted on transverse cross members, such as members 314 as shown in FIG. 24, instead.

In the embodiment of FIGS. 17(A) and (8), the each of the second end portions 122 of the overlapping elongate cross members 118 includes a connector adapted to receive and adjustably secure a support member of the system, such as a guide rod 66, 68 as illustrated in FIG. 1, as hereinabove described. In the embodiment of FIGS. 17(A) and (8), the connector is shown in the form of a compressible collet 174 extending circumferentially around the guide rod and releasably secured in position by a compression nut 176 or other suitable locking means secured thereto.

Figure 21:
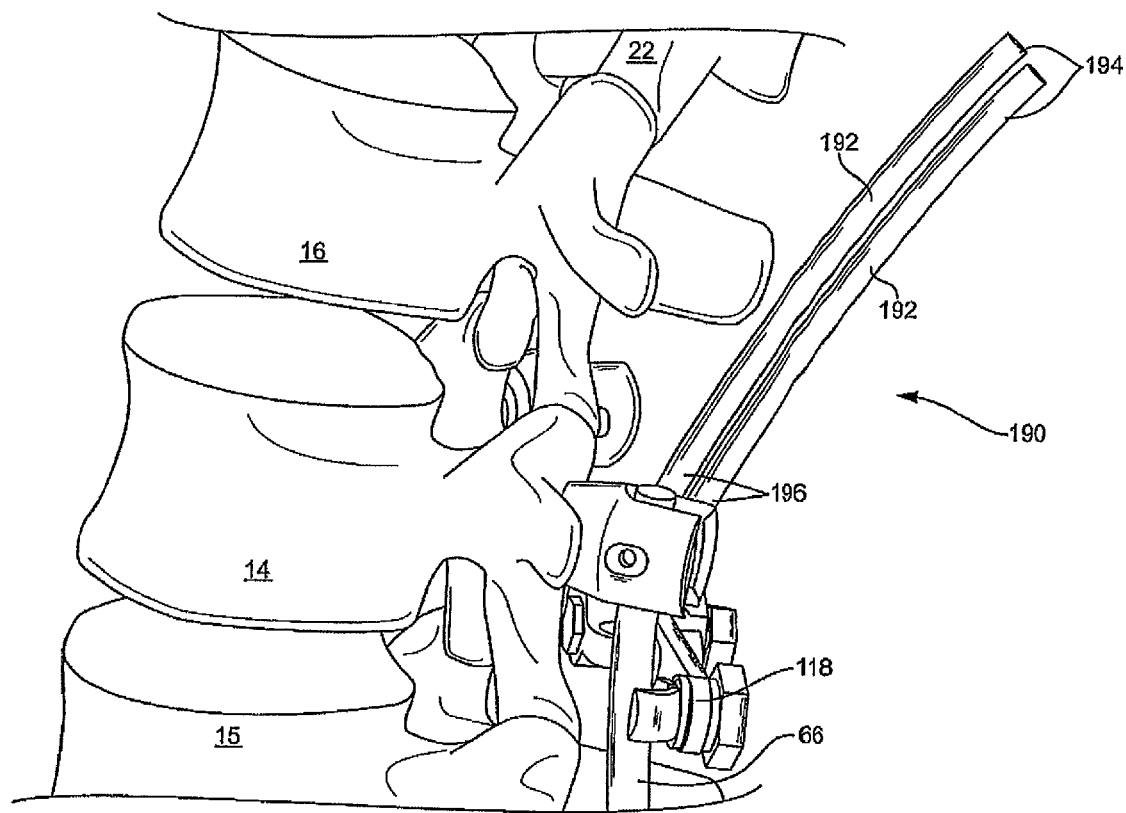
FIG. 21 is a rear perspective view of a spinal stabilization system in accordance with an embodiment of the present invention affixed to a spinal column.
Figure 22:
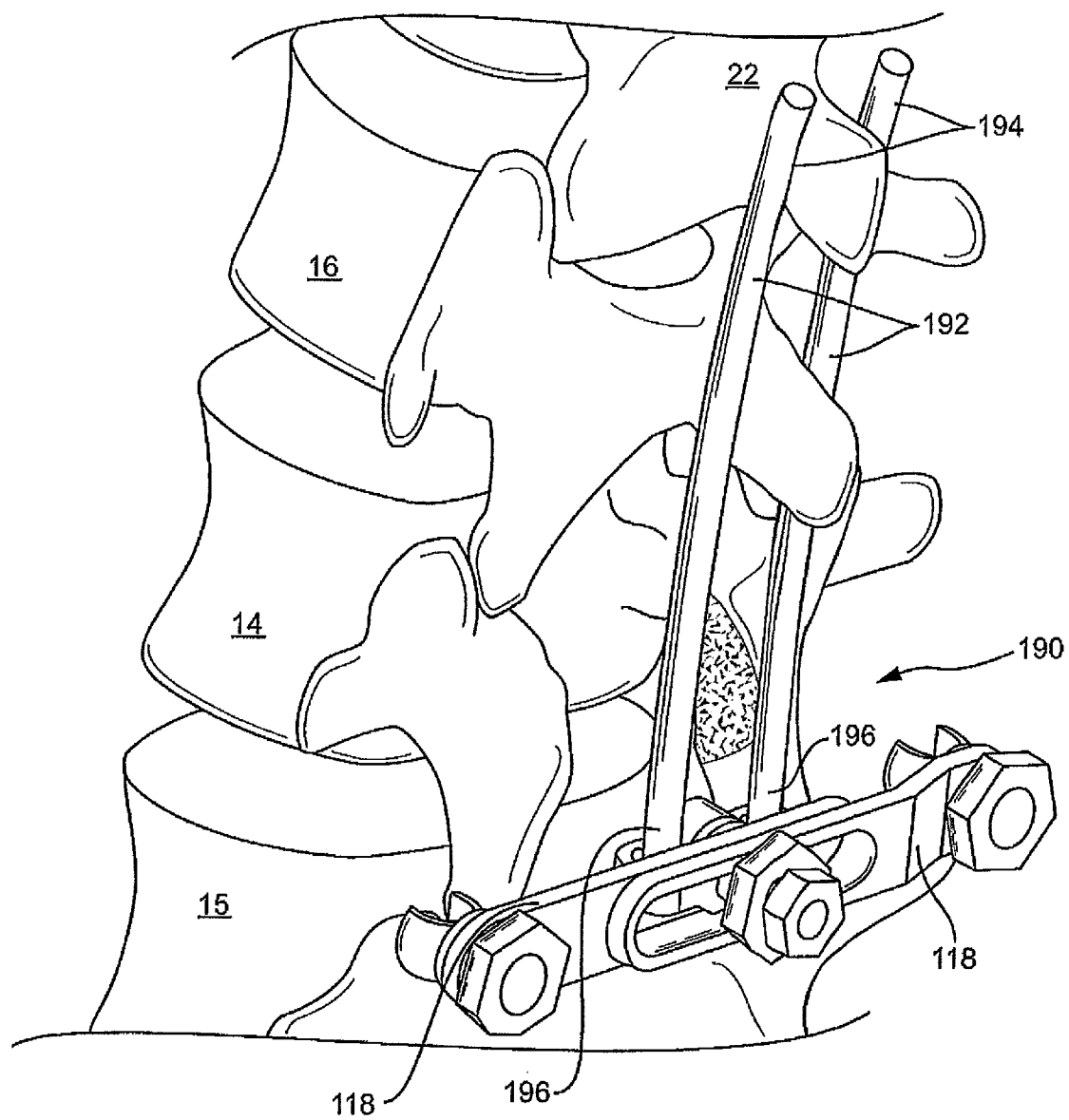
FIG. 22 is a front perspective view of the spinal stabilization system shown in FIG. 21.

In an embodiment 190 of the spinal stabilization system of the present invention as shown in FIGS. 18-23(A) and 23(8), the elongate body of the support structure as described in exemplary form above with respect to the embodiments of FIGS. 1-17 is depicted in the form of at least two elongate body members, by way of example, rods or dowels 192. Each rod includes a first and a second end 194, 196; each first end 194 being structured and arranged to be connected to an interlaminar support member 198 and each second end 196 being operatively connected to a pair of elongate cross members 118 adjustably positioned in overlapping juxtaposition with respect to one another, as described in detail above. The spherical or tubular collets 170 provide a pivotal connection of the rods to the members 118 so that each of the rods may be individually movable in any direction relative to one another and to a patient's vertebrae 14, 15, 16 and 22, as shown in FIGS. 21 and 22.

Alternatively, the rods may be tied together by a transversely extending crosspiece (not shown) so that the rods may be movable relative to the cross members 118, yet not moveable relative to one another, thereby facilitating the positioning and attachment of one or more interlaminar support members 198 thereto by suitable connections such as set screws 199 threadably inserted into apertures 200 formed in the interlaminar support member as shown in FIGS. 18, 19, 20 and 23.

Figure 23A:
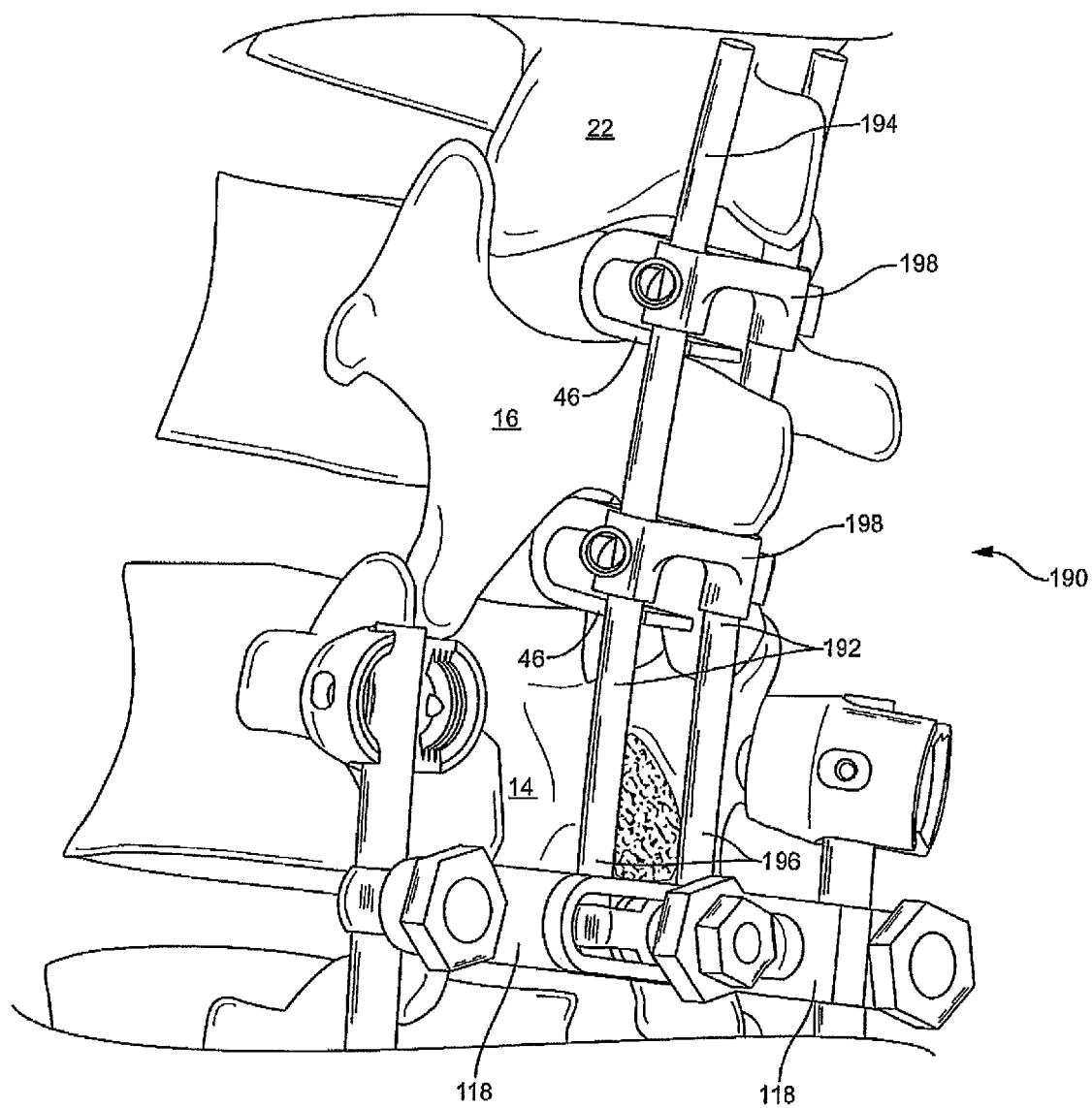
FIG. 23(A) is a front perspective view of the spinal stabilization system shown in FIG. 22 with additional elements shown affixed to a spinal column.
Figure 23B:
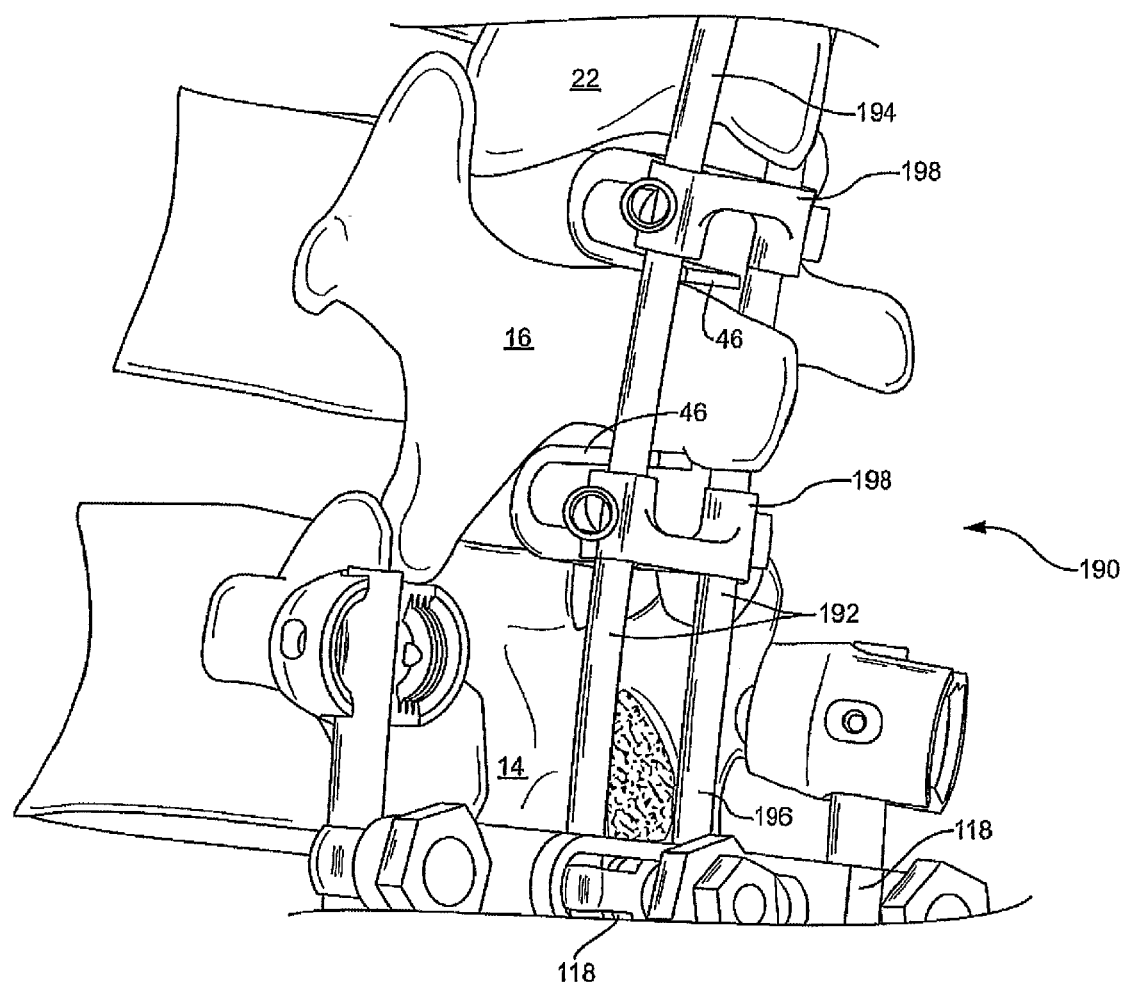
FIG. 23(B) is a front perspective view an alternate embodiment of the spinal stabilization system shown in FIG. 23(A) with additional elements shown affixed to a spinal column.

In the embodiment of FIG. 23(A), the interlaminar support members 198 are shown installed with a leg 46 that is not attached directly to a rod 192 positioned on the side closest to the transverse cross members 118, thereby directing the spring forces from the cross members relatively uniformly into the adjacent vertebrae 22, 16 and 14. However, with reference to the embodiment of FIG. 23(8), by installing the support members such that they face each other, the spring forces are directed into vertebra 16, thereby compressing it in this application.

Referring now to FIGS. 24-27, a spinal stabilization system 300 of the present invention is illustrated according to an embodiment which includes a support structure 310 structured and arranged to secure the system to a patient's spinal process or column 312 to stabilize multiple levels of vertebra 15, 14, 16, and 22, in ascending order. The support structure 310 includes a plurality of transversely extending elongate cross members 314 adjustably positioned one above the other in general alignment with the spinal column 312. In the embodiment shown, by way of example and not of limitation, the cross members are in the form of a pair of transversely extending rods which span the spinal column in with respect to one another. However, it is to be understood that three or more cross members of various shapes and configurations may also be used without departing from the scope of the present invention. In the embodiment of FIG. 24, an intervertebral body fusion device ("IBFD") 311 is shown inserted between each of the adjacent vertebrae 15, 14; 14, 16; and vertebrae 16, 22 to provide additional stability to the spinal column 312.

Figure 25:
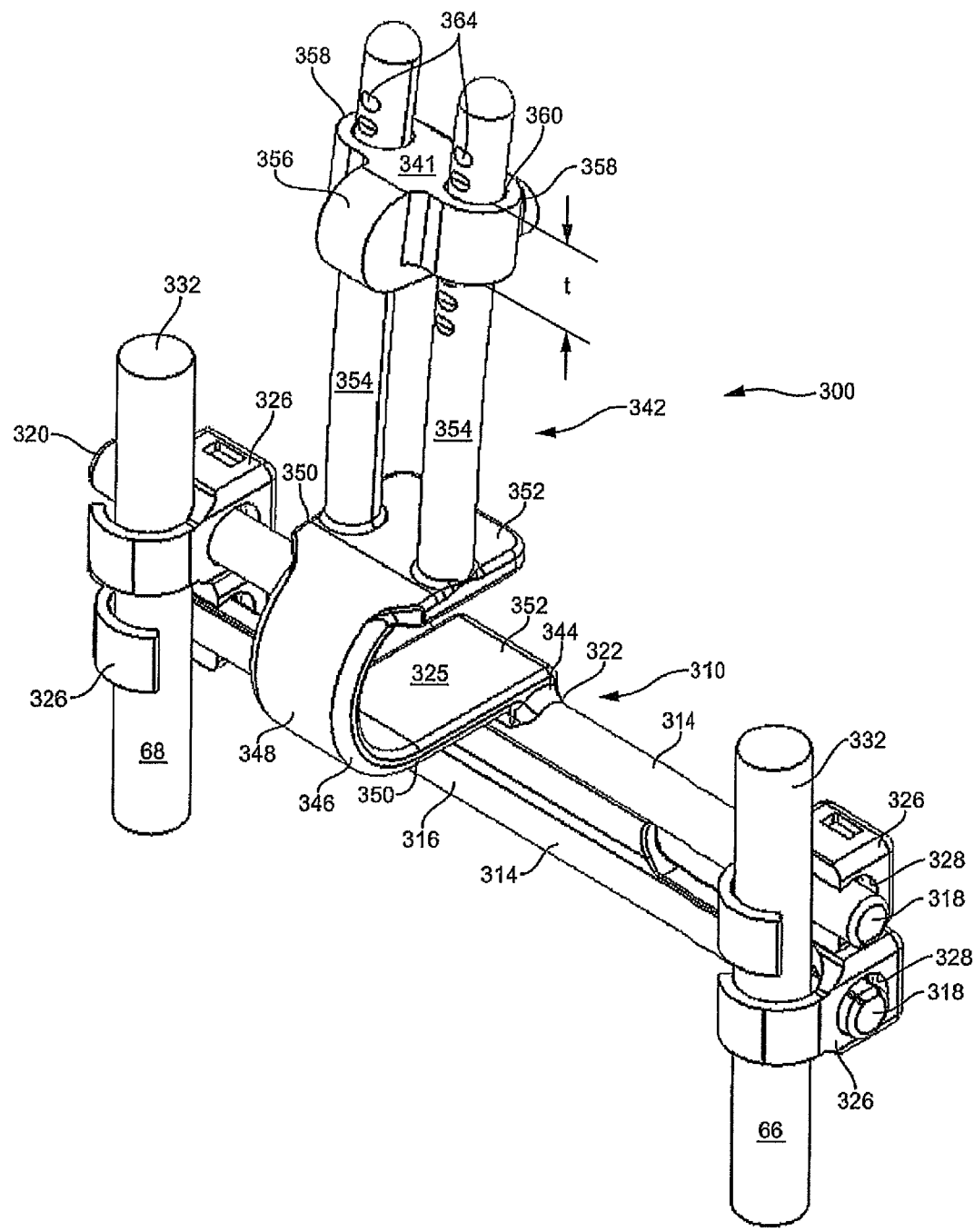
FIG. 25 is a rear side perspective view of a spinal stabilization system in accordance with an embodiment of the present invention.
Figure 26:
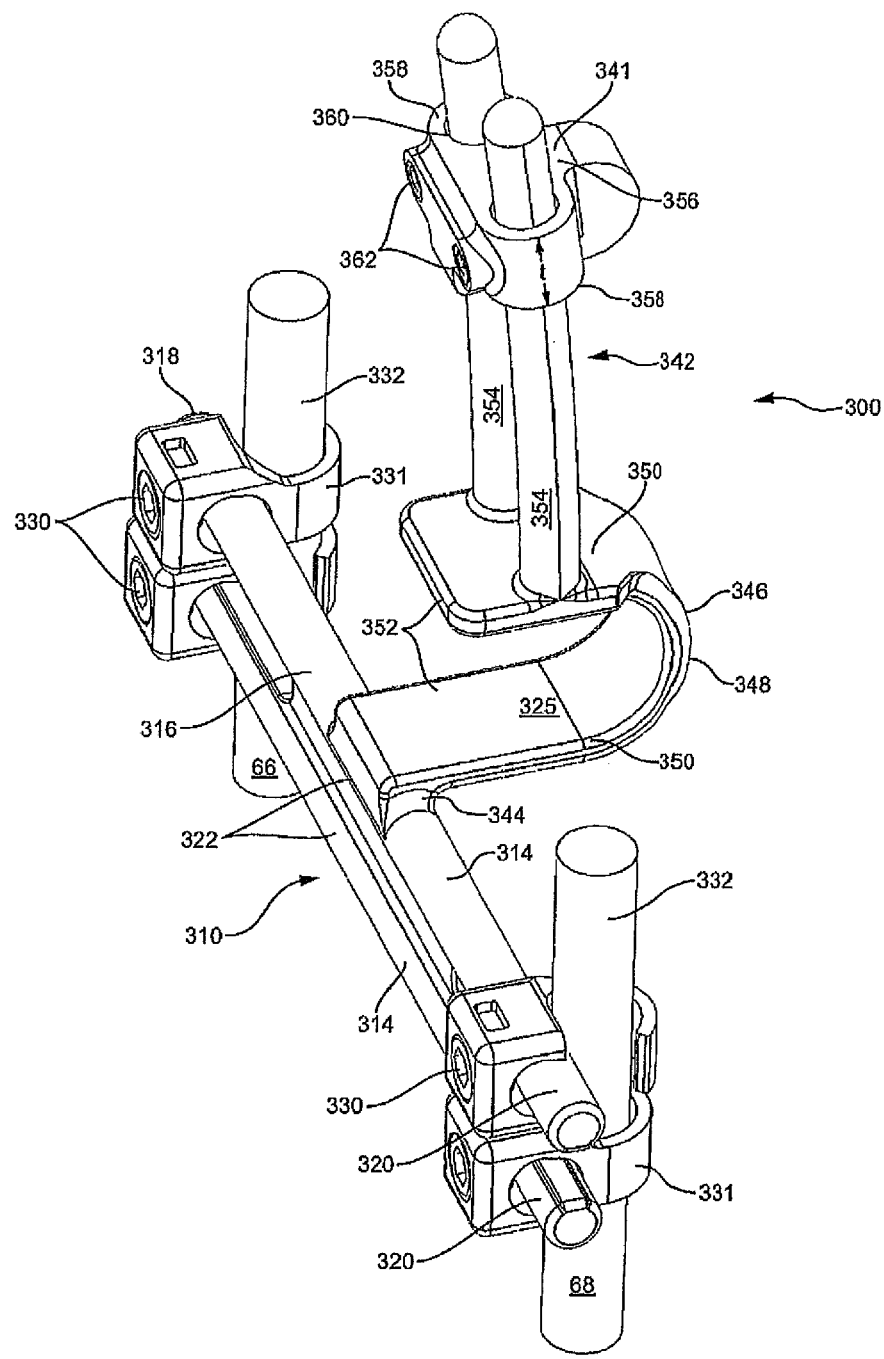
FIG. 26 is a front side perspective view of the spinal stabilization system shown in FIG. 25.

As shown in greater detail in FIGS. 25 and 26, each cross member 314 comprises an elongate body 316 having first and second end portions 318, 320 and a midpoint 322 and is structured and arranged to be operatively connected at approximately the midpoint to a first interlaminar support member 325. Each of the ends 318, 320 of the cross members are adapted to receive a connector or securing device 326 for adjustably securing first and second support members 66 and 68 respectively, as described above with respect to other embodiments of the present invention and in greater detail below.

Figure 27A:
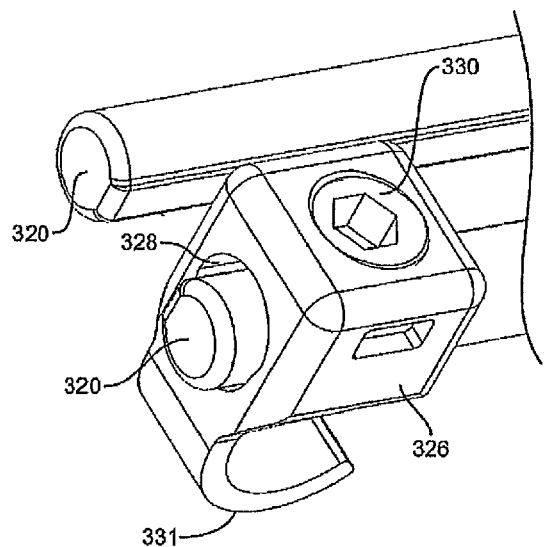
FIG. 27(A) is a side perspective view of portions of the spinal stabilization system shown in FIGS. 25 and 26.
Figure 27B:
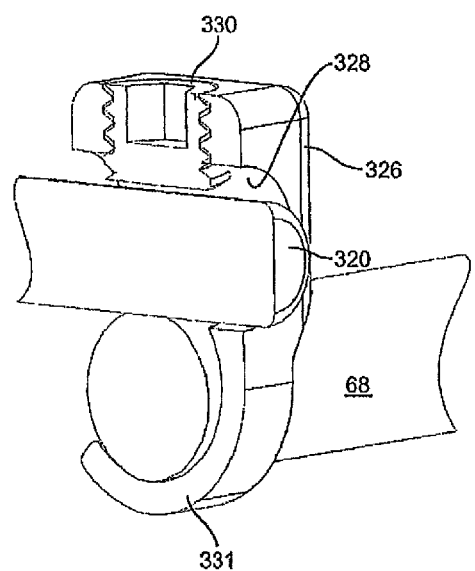
FIG. 27(B) is a left partial sectional side perspective view of portions of the spinal stabilization system shown in FIGS. 25 and 26.
Figure 27C:
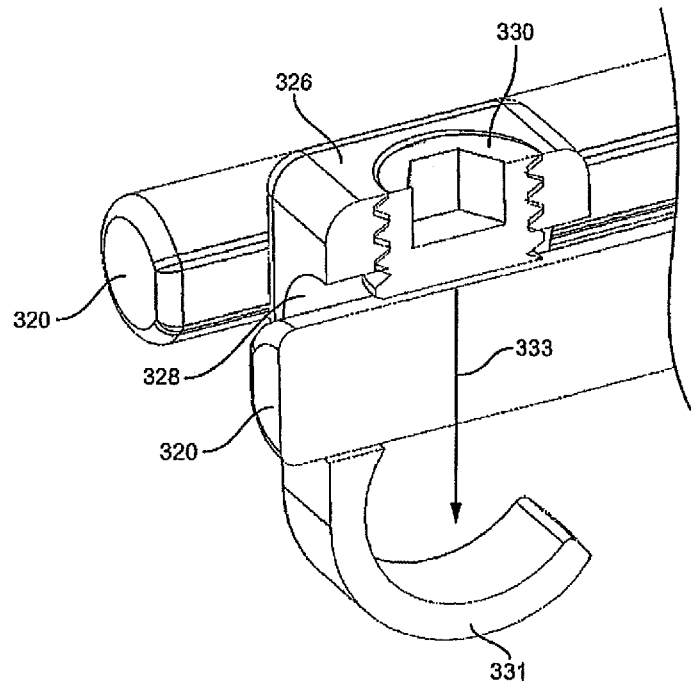
FIG. 27(C) is a right partial sectional side perspective view of portions of the spinal stabilization system shown in FIGS. 25 and 26.
Figure 28:
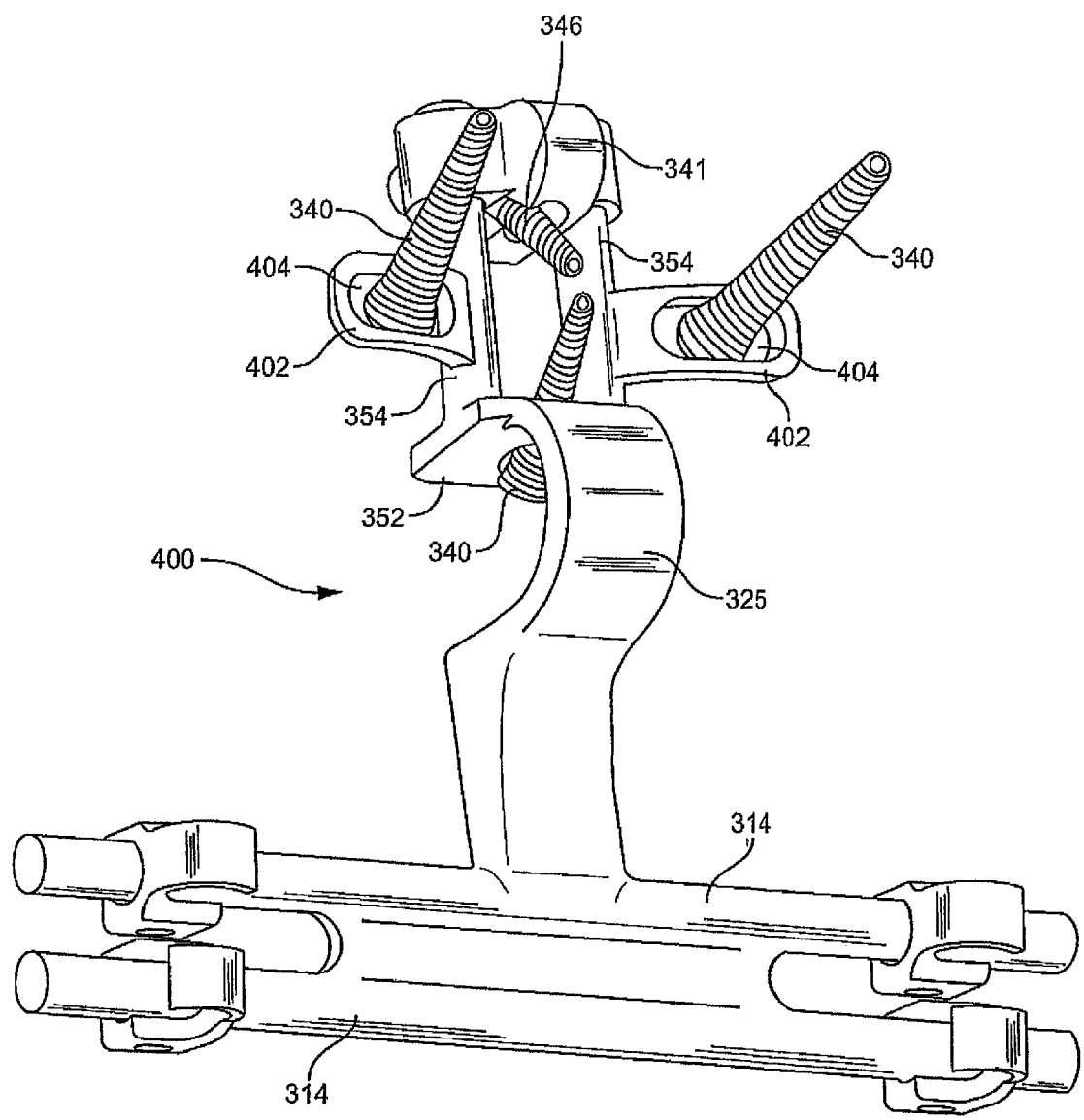
FIG. 28 is a lower side perspective view of a spinal stabilization system in accordance with an embodiment of the present invention.

FIG. 27 illustrates the elements of each connector 326 in greater detail. Each connector has an aperture 328 formed therein respectively for receiving one of the ends 318, 320 of the elongate body portion 316 of cross member 314, each of which may be held in a preselected position by a set screw or other fastening means 330. Each connector further includes a retainer or bracket element 331, which, in the embodiment shown, is in a generally J or hook shaped configuration adapted to conform to the shape of the support members 66, 68; however, other configurations and shapes may also be employed to adapt to the configurations of the support members which may be used. In the embodiment shown, by way of example only and not of limitation, the support members are in the form of guide rods 66, 68, each guide rod having an upper end 332 and a lower end 334. The guide rods 66, 68 may be secured following alignment and adjustment of the system 300 to a patient's anatomy and spinal structure (as shown generally in FIG. 24) by pressure transmitted from a respective set screw 330 via an end of a cross member 320 indicated by arrow 333 in FIG. 27(C).

Each of the upper and lower ends of the support members 66, 68 has a securing device 336 slideably positioned thereon and adapted to be secured thereto by means of set screws 338. By way of example, each of the securing devices 336 is adapted to receive a bone screw 340, each bone screw being structured and arranged to be secured to one of the vertebra of the spinal column 312.

Referring again to FIGS. 25 and 26, the elements of the interlaminar support member 325 and other elements of the support system 300 are disclosed in further detail. Similar in construction to the embodiment of the system of FIG. 1, interlaminar member 325 is adapted to be positioned between adjacent vertebrae in a spinal column. As shown in greater detail in FIG. 24, the interlaminar member 325 is shown positioned between a first vertebra 16 and a second adjacent vertebra 22 in a spinal column 312.

The system further includes a second interlaminar member 341 adapted to be positioned between the second vertebra 22 and a third vertebra 23 in the spinal column 312. Both the first and second interlaminar members are operatively connected to a support structure shown generally at numeral 342. By way of example, in the embodiment shown, the support structure 342 and the first interlaminar member 325 are integrally formed from a single piece of material such as titanium or stainless steel suitable for use as a medical implant device, and the interlaminar structure 325 may be welded at 344 to one of the cross members 314. However, it is to be understood that other means for forming and/or interconnecting the various elements of the system such as hinges, pins, threaded fasteners, casting techniques and the like may also be used without departing from the scope of the invention.

Interlaminar member 325 comprises a U-shaped body 346 defined by an elastic midsection 348, two spaced apart end portions 350, and a pair of juxtaposed legs 352, each leg extending substantially parallel to one another from one of the respective ends in a direction generally outwardly away from the spinal column 312 and spaced apart a preselected distanced (FIG. 24). Distanced is determined by the size of the interlaminar member 325, which is, in turn, is selected based upon the spacing between the vertebrae 16 and 22, respectively. The interlaminar member is intended to fuse the vertebrae. Accordingly, it is sized to be a tight fit, and the elastic properties of the U-shaped body 348 act as a spring or shock absorber in the interface between the two vertebrae. Further, the uppermost one of the legs 352 may be used as a handle to insert and position the system during surgery.

As discussed above with respect to the embodiment of FIG. 1, while the body 346 is described as being U-shaped, it is to be understood that many other shapes and configurations may also be effectively employed without departing from the scope of the present invention. It is also to be noted that both interlaminar members 325 and 341 include pointed ridges or teeth 327 extending outwardly therefrom which are adapted to engage portions of vertebra 22 positioned therebetween to prevent slippage of the stabilization system 300 following installation.

The system 300 further comprises a pair of support members or guide rods 354 secured to the interlaminar support member 325 and extending in a direction upwardly therefrom substantially parallel to one another. The second interlaminar member 341 includes a body portion 356 of a preselected thickness t, which is selected based upon the spacing between vertebrae 22 and 23, and is intended to be smaller in size than the spacing to allow for flexion of the spinal column 312.

The body portion 356 further includes a pair of oppositely positioned ears 358 extending laterally outwardly from the body portion in opposing directions, each of the ears containing an aperture 360 structured and arranged to slideably receive one of the support members or guide rods 354. As will be discussed in greater detail below, the second interlaminar member is movably supported by the upwardly extending support members or guide rods, and the position of the second interlaminar member 341 relative to the first interlaminar member 325 may be adjusted depending upon the dimensions of the specific spinal column on which the system is installed and the range of motion desired. Once the position of the second interlaminar member 341 has been selected, it is locked in place by a pair of set screws or other suitable fastening means 362 extending through each of the ears 358 and adapted to releasably engage the respective guide rod extending therethrough. A plurality of spaced-apart recesses 362 adapted to receive the ends of may be formed in each of the guide rods to assist in positioning interlaminar member 341.

Figure 29:
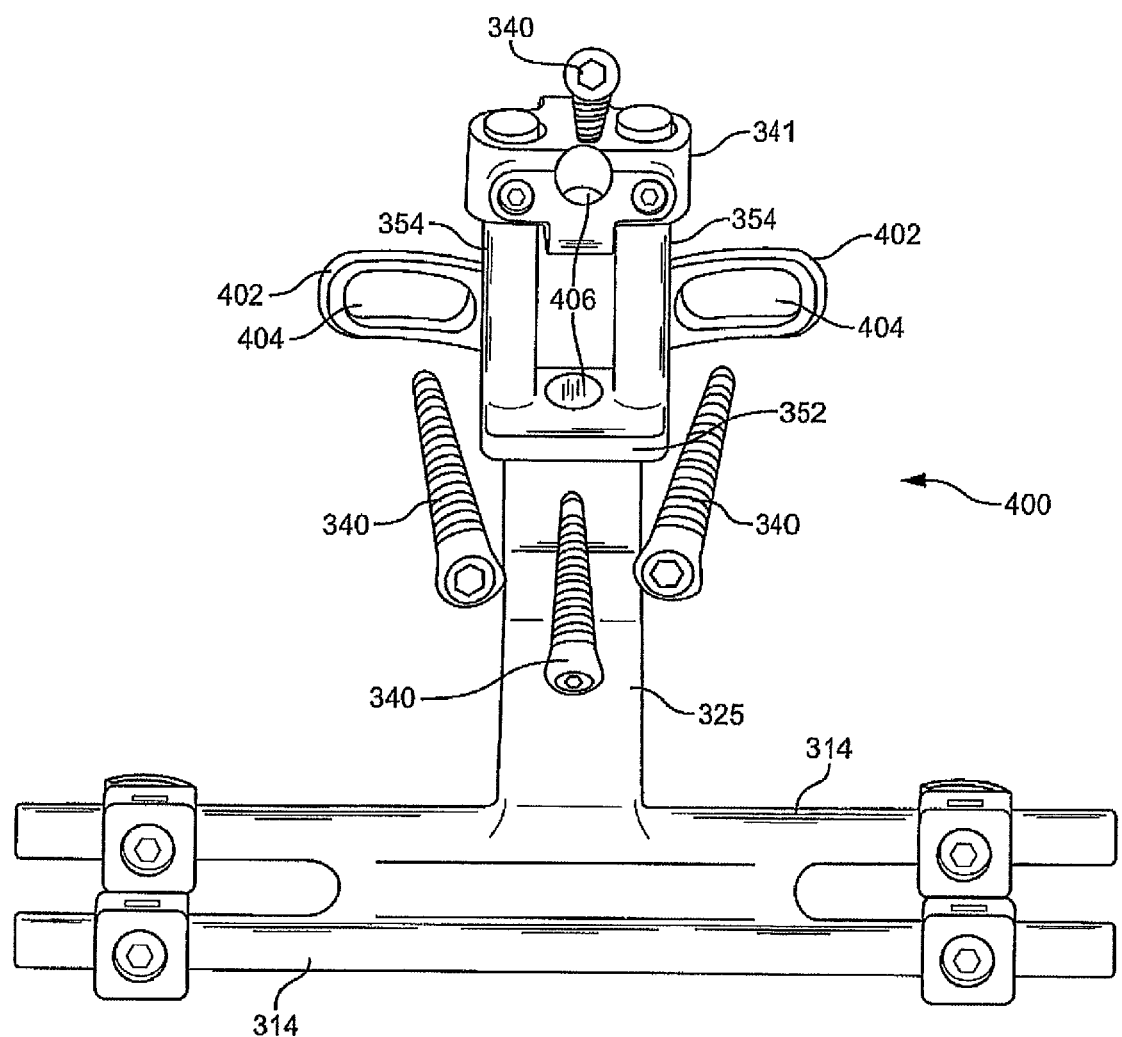
FIG. 29 is a bottom front perspective view of the spinal stabilization system shown in FIG. 28.
Figure 30:
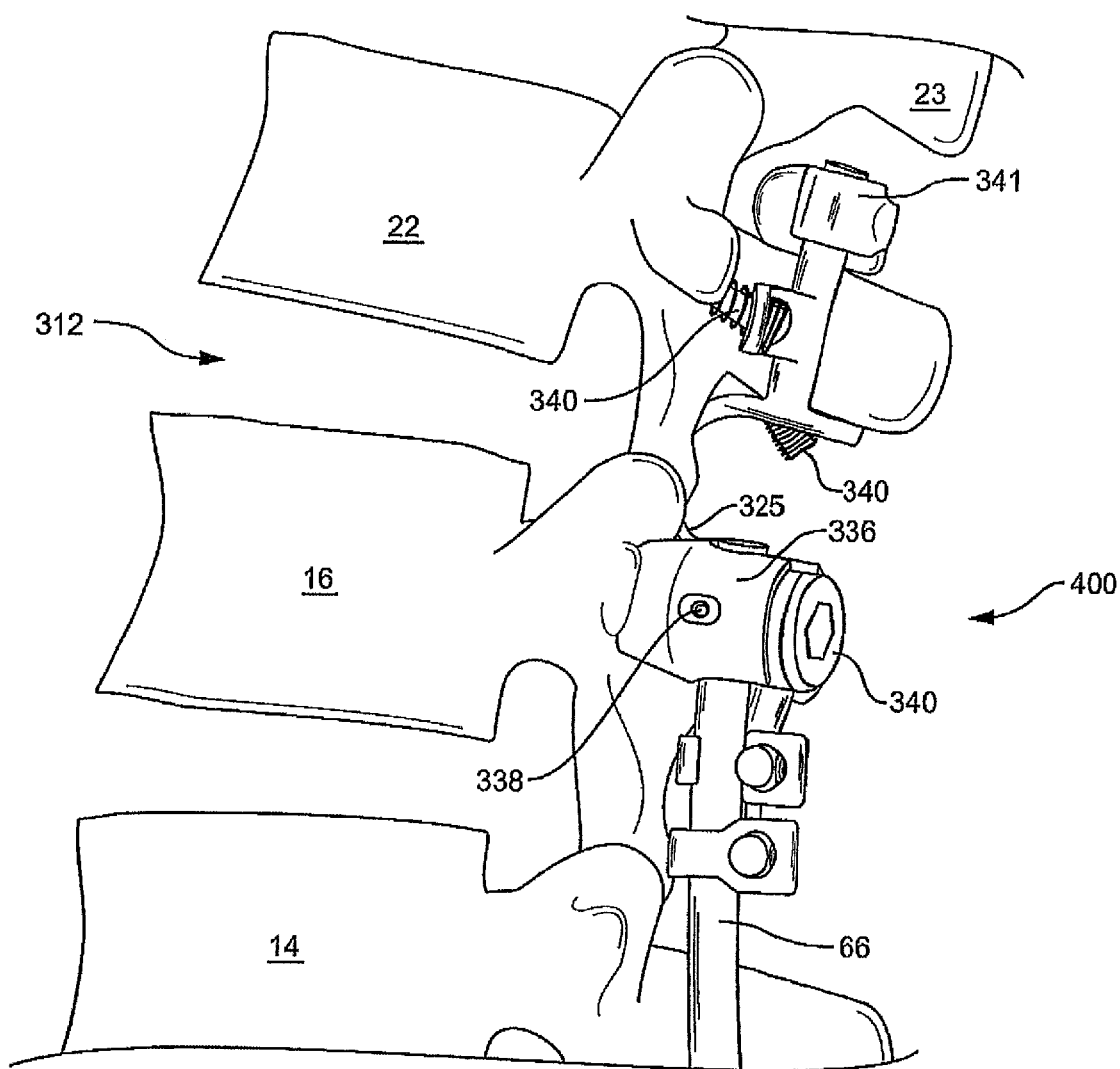
FIG. 30 is a side view of the spinal stabilization system of FIG. 28 shown affixed to a spinal column.
Figure 31:
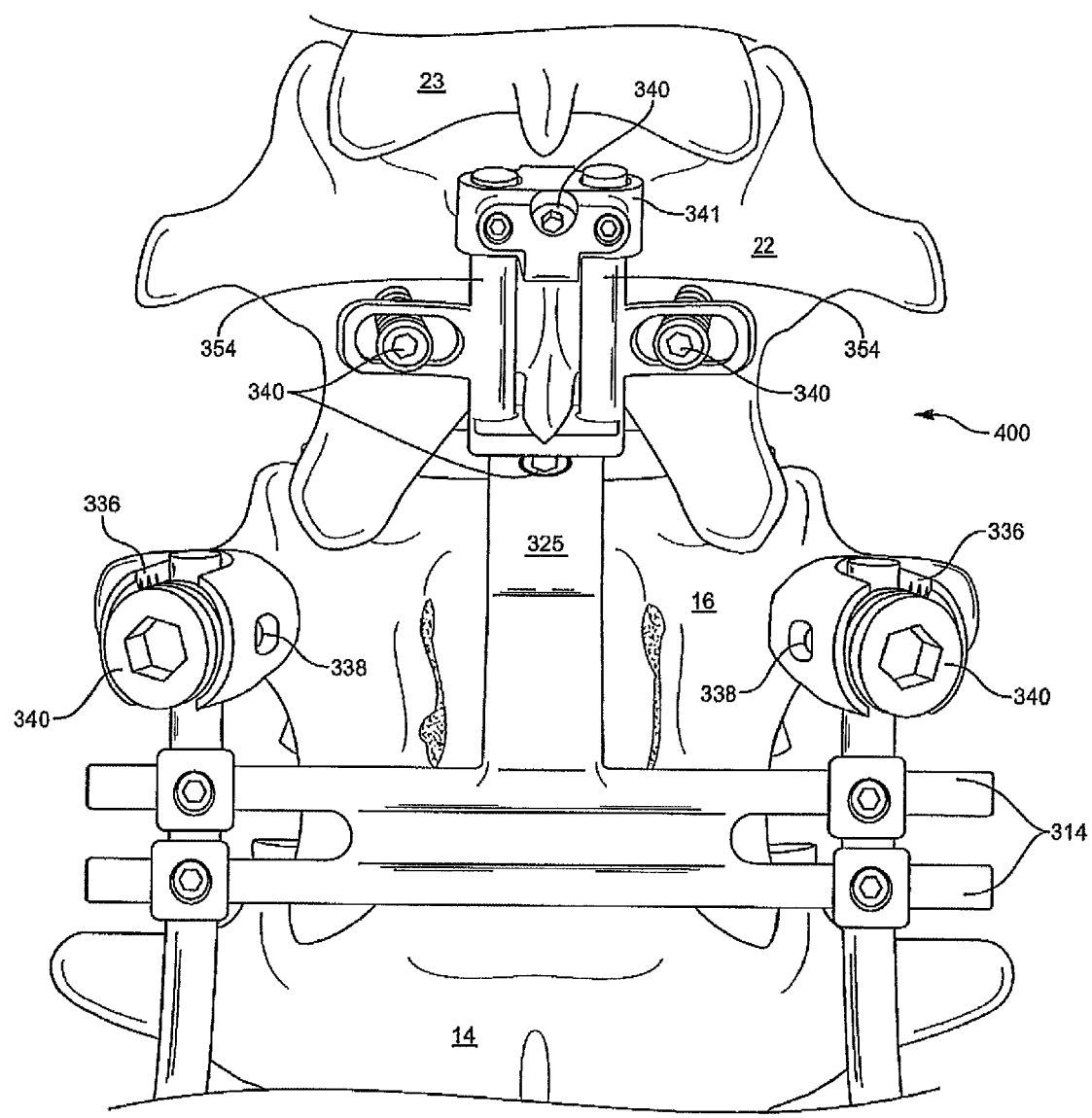
FIG. 31 is a front view of the spinal stabilization system shown in FIG. 30.

Increased stability to a spinal fixation system may be provided by employing additional pedicle screws at selected locations in the system. For example, in accordance with another embodiment of the instant invention, a spinal fixation system 400 with increased stability is depicted in FIGS. 28-31. Of substantially the same configuration as the spinal stabilization 300 of the embodiment shown in FIG. 24, the system 400 includes a pair of oppositely disposed brackets 402 each connected to one of the support members or guide rods 354. Each bracket includes an aperture or slot formed therein, each slot being adapted to receive at least one pedicle screw 340. As best shown in FIG. 29, apertures 406 formed in the uppermost leg 352 of the first interlaminar support member 325 and in the second interlaminar support member 341, respectively are each likewise adapted to receive a pedicle screw 340. The reader will appreciate that the pedicle screws received in each of the apertures 404 are positioned at a divergent angle with respect to one another, and the pedicle screws received in apertures 406 are positioned at a convergent angle with respect to one another, thus providing enhanced stability to the stabilization system 400 by a uniform distribution of the structural loading imposed thereon by the dynamics of the patient's post-operation movements.

Figure 32:
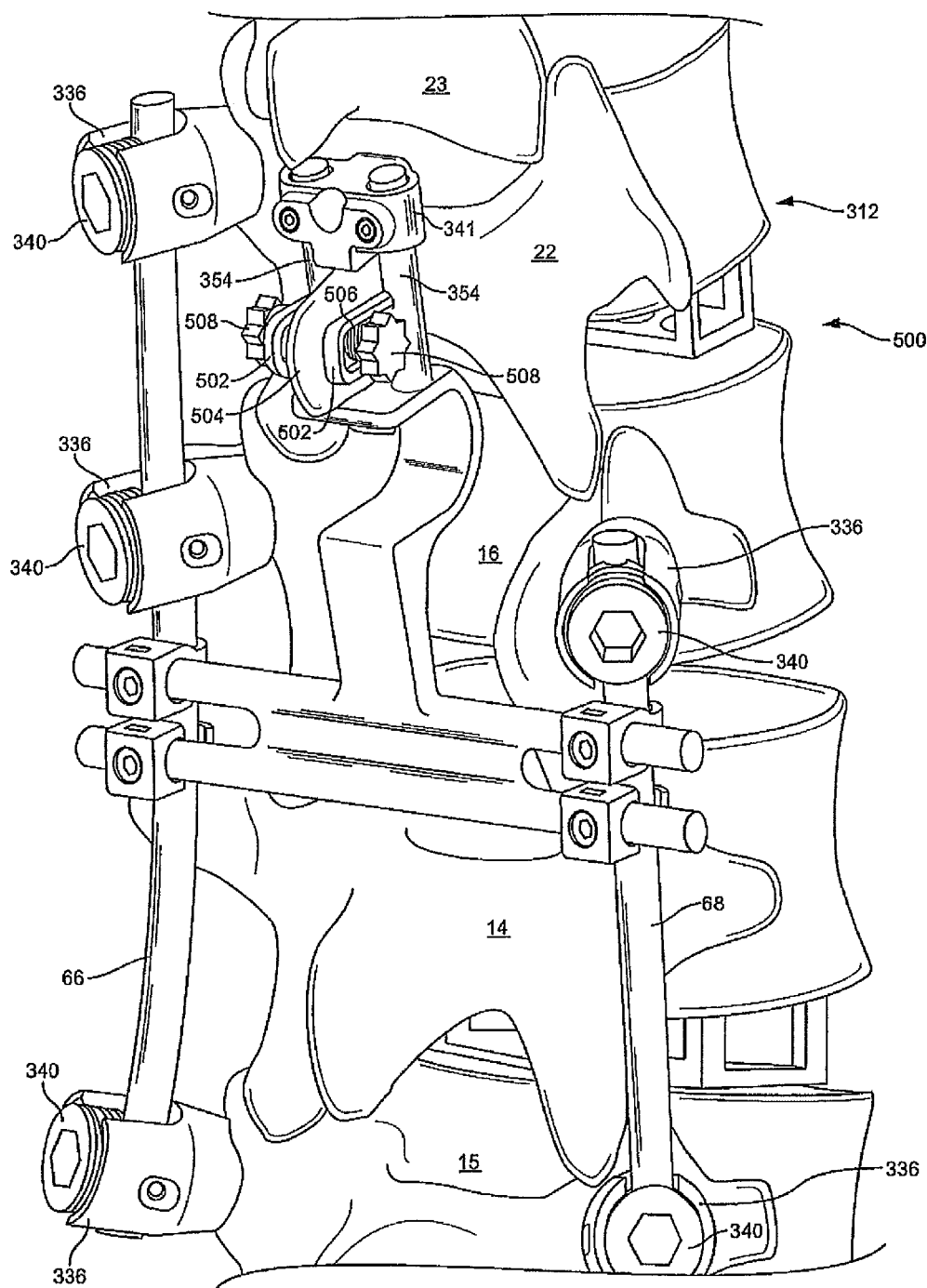
FIG. 32 is a side perspective view of a spinal stabilization a spinal stabilization system in accordance with an embodiment of the present invention shown affixed to a spinal column.
Figure 33:
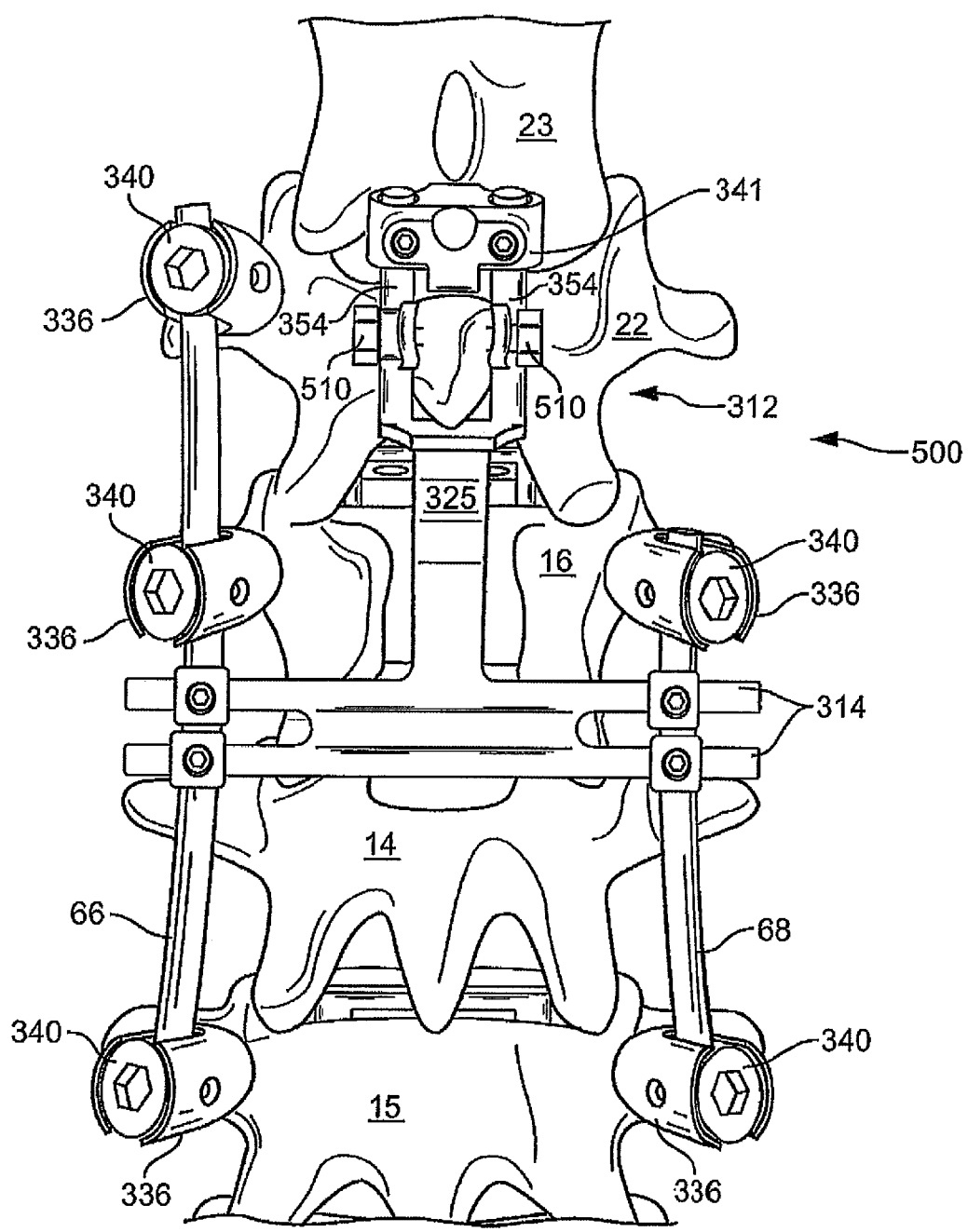
FIG. 33 is a front perspective view of the spinal stabilization system shown in FIG. 32.

FIGS. 32 and 33 illustrate yet another embodiment 500 of a spinal stabilization system of the present invention structured to provide enhanced system and spinal stabilization. In this embodiment, each of the support members or guide rods 354 includes an ear or bracket member 502 operatively connected thereto and extending transversely outwardly therefrom in a direction generally away from the spinal column 312 and parallel and adjacent to an outwardly extending portion 504 of vertebra 22.

Each bracket has an aperture or eyelet 506 formed therein adapted to receive a retention device 508 adapted to releasably engage vertebra portion 504, each of the fasteners being oppositely disposed so as to cooperate with each other in applying a clamping force to the vertebra portion. In the embodiment shown, by way of example and not of limitation, the fasteners are in the form of threaded fasteners or bolts, each having a knurled knob 510 attached thereto to facilitate installation tightening thereof; however, it is to be understood by those skilled in the art that other forms of retaining devices such as pins, clamps and the like may be used without departing from the scope hereof. As described above with respect to an earlier embodiment, each bracket 502 may include an inner surface or face (not visible in the figures) which has sharp protrusions, or teeth Extending outwardly therefrom adapted to engage and even imbed in outwardly, extending portion 504 of vertebra 22 to prevent slippage following installation of the system.

Referring now to FIGS. 34-36, exemplary embodiments of interlaminar support members are illustrated in greater detail. Depending upon the application and the degree of support required to stabilize a particular patient's spinal column, an interlaminar support member may be of a generally rigid construction, a generally flexible construction, or it may contain both generally rigid and generally flexible portions. As will be described below in greater detail, the rigid or flexible portions of a support member are typically compressed by a separate compression tool upon installation against first and second oppositely disposed bone surfaces of adjacent vertebrae, such as vertebrae 14 and 16 shown in FIGS. 6 and 7, and are retained in position by the elements of the support system and locking means such as threaded fasteners, set screws and the like, as described above.

Figure 34A:
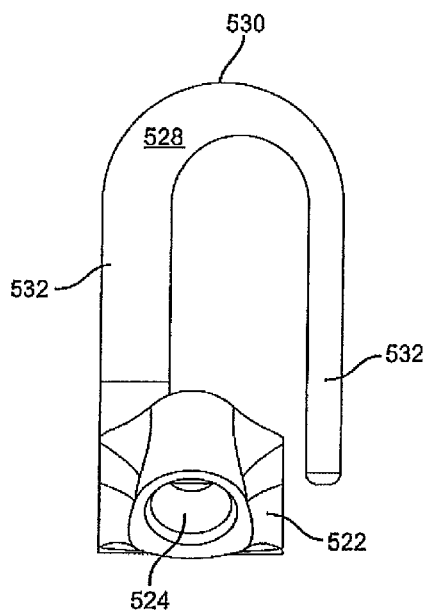
FIG. 34(A) is a side view of an element of a spinal stabilization system in accordance with an embodiment of the present invention.
Figure 34B:
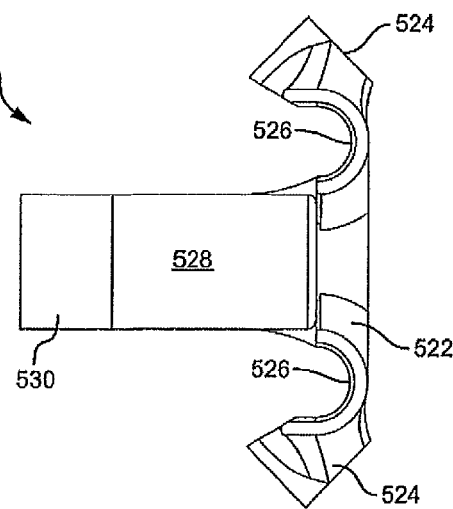
FIG. 34(B) is a top view of an element of the spinal stabilization system shown in FIG. 34(A)
Figure 34C:
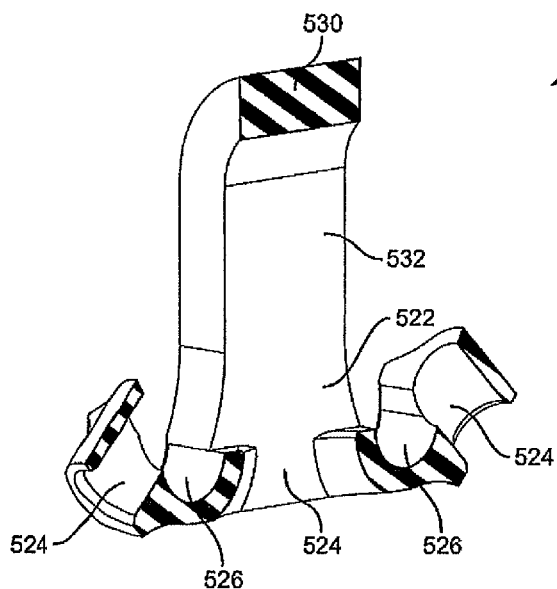
FIG. 34(C) is a right perspective side sectional view of an element of the spinal stabilization system shown in FIGS. 34(A) and 34(B)
Figure 34D:
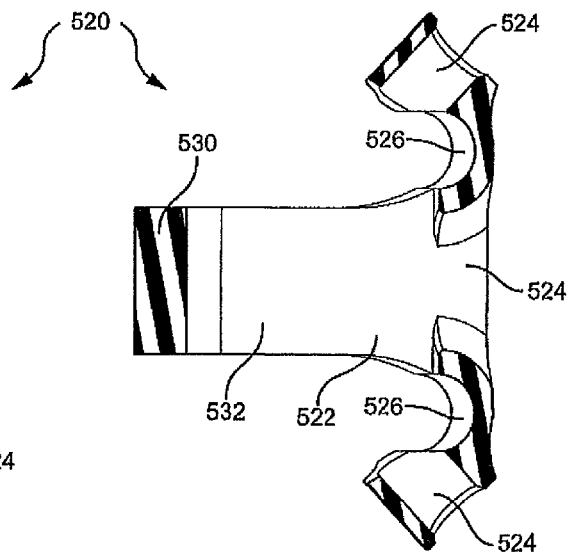
FIG. 34(D) is a top sectional view of an element of the spinal stabilization system shown in FIGS. 34(A), 34(B) and 34(C)

According to an embodiment depicted in FIGS. 34(A)-(C), an interlaminar support member 520 comprises a generally T-shaped body 522 having a plurality of apertures 524 formed therein, each aperture adapted to receive a pedicle screw or other suitable fastener (not shown) for securing the support member to a vertebra, and a plurality of recesses 526, each recess being structured and arranged to adjustably receive a support member (such as guide rod 28 of the embodiment of FIG. 1). Interlaminar support member 520 further includes a U-shaped body 528 defined by an elastic midsection 530 and two spaced apart juxtaposed legs 532, each leg, when in place in a spinal process, extending substantially parallel to one another from the elastomeric midsection in a direction generally outwardly away from the spinal column. The interlaminar support member is intended to fuse the adjacent vertebrae. Accordingly, it is sized to be a tight fit, and the elastic properties of the U-shaped body 528 act as a spring or shock absorber in the interface between the two vertebrae.

Figure 35A:
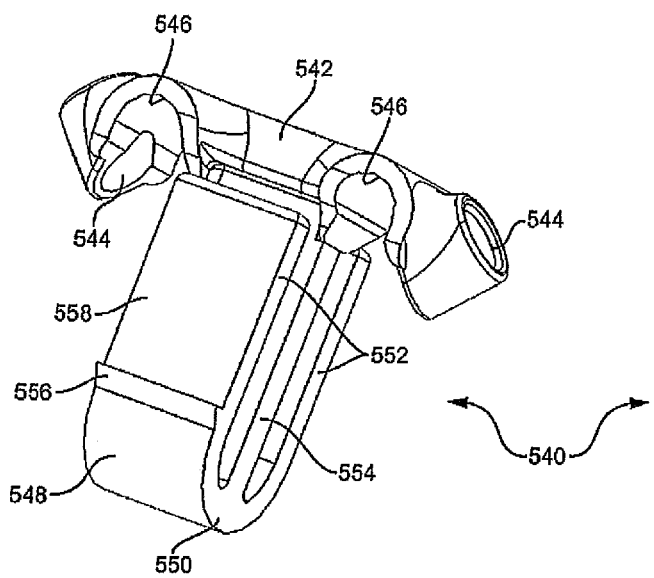
FIG. 35(A) is a top perspective view of an element of a spinal stabilization system in accordance with an embodiment of the present invention.
Figure 35B:
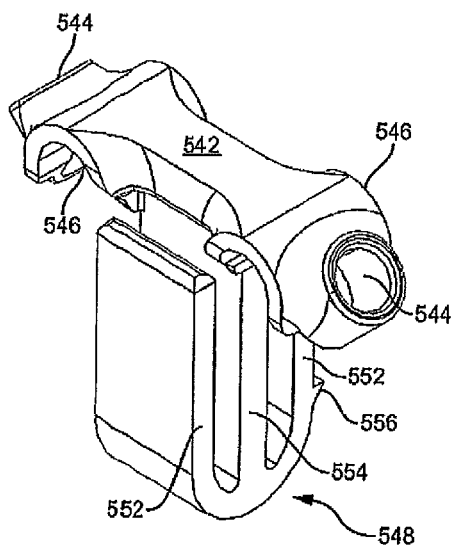
FIG. 35(B) is a bottom perspective view of an element of the spinal stabilization system shown in FIG. 35(A)
Figure 35C:
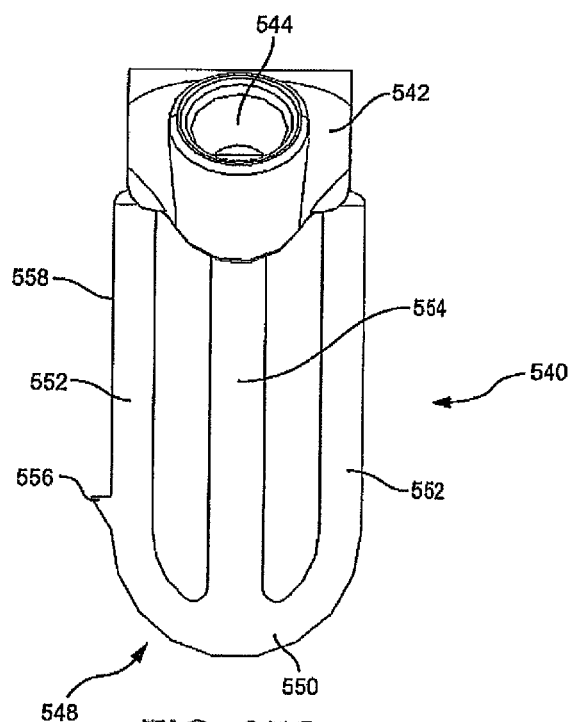
FIG. 35(C) is a side view of an element of the spinal stabilization system shown in FIGS. 35(A) and 35(B)

Referring to FIGS. 35(A)-(C), an interlaminar support member 540 is illustrated which includes a generally T-shaped body 542 having a plurality of apertures 544 formed therein, each aperture adapted to receive a pedicle screw or other suitable fastener (not shown) for securing the support member to a vertebra, and a plurality of recesses 546, again each recess being structured and arranged to adjustably receive a support member (such as guide rod 28 of the embodiment of FIG. 1). The support member 540 further includes a U-shaped body 548 defined by an elastic midsection 550 and two spaced apart juxtaposed legs 552, the U-shaped body being operatively connected to the T-shaped body by a planar arm member or bracket 554 positioned intermediate the legs 552. As described above with respect to the embodiment of FIG. 34, each leg, when in place in a spinal process, extends substantially parallel to one another and to the bracket 554 from the elastomeric midsection 550 in a direction generally outwardly away from the spinal column. At least one of the legs further includes a wedge or V-shaped protrusion 556 extending outwardly therefrom and transversely across an outer surface 558 thereof, the protrusion being structured and arranged to resistively engage one of the oppositely disposed bone surfaces of adjacent vertebrae upon installation of the support system to prevent unintended displacement thereof.

Figure 36A:
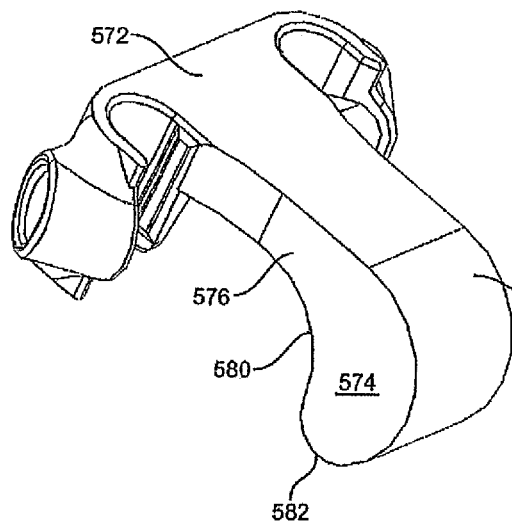
FIG. 36(A) is a top perspective view of an element of a spinal stabilization system in accordance with an embodiment of the present invention.
Figure 36B:
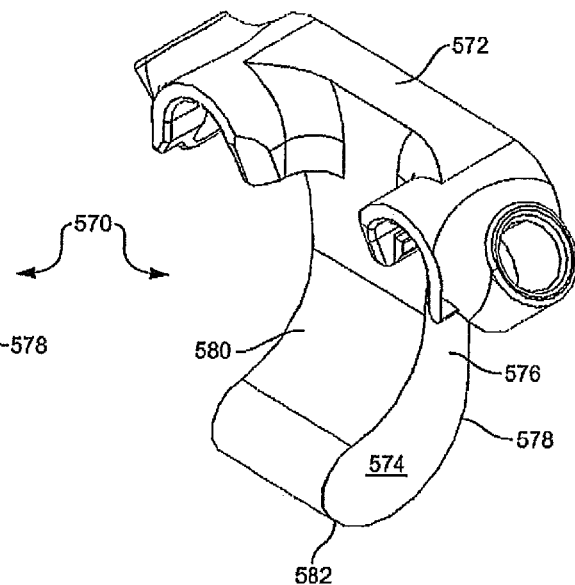
FIG. 36(B) is a bottom perspective view of an element of the spinal stabilization system shown in FIG. 36(A)
Figure 36C:
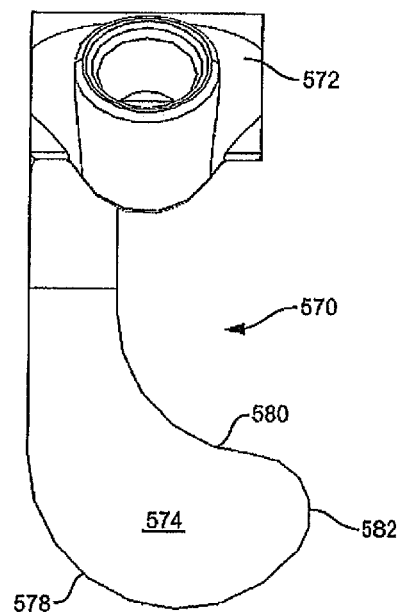
FIG. 36(C) is a side view of an element of the spinal stabilization system shown in FIGS. 36(A) and 36(8); B

In accordance with another embodiment 570 of an interlaminar support member as shown in FIGS. 36(A)-(C), a generally T-shaped body member 572, of similar configuration to the T-shaped body members of the embodiments of FIGS. 34 and 35, includes a generally J-shaped member 574 extending transversely therefrom defined by a pair of oppositely disposed sides 576 and curved upper and lower surfaces 578, 580 which intersect to define a rounded or knob-shaped end portion 582. The support member 570 is installed intermediate a pair of adjacent vertebrae by forcibly inserting the rounded end portion therebetween and then rotating it about the end portion to a desired position, whereupon it is secured in place by pedicle screws and guide rods, as described above.

In other aspects of the instant invention, the elements of the stabilization system may be adapted to be adjusted in response to a patient's anatomical structure. For example, the U-shaped body portion of an interlaminar device as hereinabove described may be configured to include a triangular or wedge-shaped body portion for ease of implantation and fitting in situations where a patient's anatomy may not accommodate a U-shaped configuration. The final implanted profile of an implant device may also be adjusted for purposes of bone-implant conformity, and the material thickness and physical properties of the device may be tailored to provide a specific stiffness, enhanced fatigue resistance and a preselected range of motion in a chosen direction, depending upon the patient's overall condition and flexibility.

In a similar manner, the crosslink members may also be too short or too long for a patient's anatomical structure. Accordingly, the system of the present invention may include crosslink members of varying lengths or having adjustable lengths, thicknesses, diameters or thicknesses and stiffness properties which may be selected by the practitioner depending upon the patient's requirements.

In a similar manner, the vertical section of the interlaminar device which extends intermediate the shaped body portion which is positioned intermediate adjacent vertebrae and at least one crosslink member may be provided in varying fixed lengths or in an adjustable configuration, by way of example, in the form of a pair of overlapping elongate members which may be adjusted to a desired length during the implantation process and then fixed by suitable fastening systems such as screws, cooperating nuts and bolts, and the like. Moreover, to achieve proper placement of the system, the angulation between the crosslink member and the vertical section of the system is adjustable to accommodate the spinal curvature of the patient's spine. This feature may be provided by incorporating a wedge, an angulated L-shape, an S-shape or some other geometric shape into a lower vertical connection portion of the interlaminar device. It may also be achieved by modifying the lengths, thicknesses, spacing, surface texture and angular relationships between the legs of the interlaminar device to ensure ease of insertion and correct orientation with respect to the vertebrae, thus providing proper conformation with the interlaminar space and uniform support following installation.

Robust fixation of the system, in particular the connections between the crosslink member(s), the pedicle screws and the hook devices interconnecting them is achieved via judicious selection of size, strength or stiffness so that all of the interconnected components interact as a system to provide stability against axial, sagittal and coronal torsions. A unique feature of the foregoing is the overall adaptability of the system to the requirements of the patient's anatomical structure and the issues being addressed. Once the sizes, configurations and physical properties of the system components have been determined, the system may be installed on the patient's spine and fine-tuned to provide the requisite stiffness, support and range of motion.

In particular aspects, the different elements of the system may be configured with tool engagement features in order to permit a surgeon to grasp the implant with a tool assembly or insertion tool to ease implantation of the various components. For example, the insertion tool may be configured as a pair of pliers or hemostats. As another example, a threaded portion of a tool assembly may reversibly secure to a complementary threaded portion of the implant in order to ease implantation.

Accordingly, a tool assembly may be comprised of a cannulated shaft with a retainer shaft housed substantially within, the retainer shaft further configured with a threaded portion at its proximal end which may extend out of a proximal end of the retainer shaft and a handle located and attached to a proximal end of the retainer shaft. The proximal end of the retainer shaft may have a feature that permits rotation of the retainer shaft via another tool, such as the mechanical arrangement that exists between a wrench and nut, in order to secure the tool assembly to the implant. After implantation of the implant the tool assembly may be decoupled and removed.

Figure 37C:
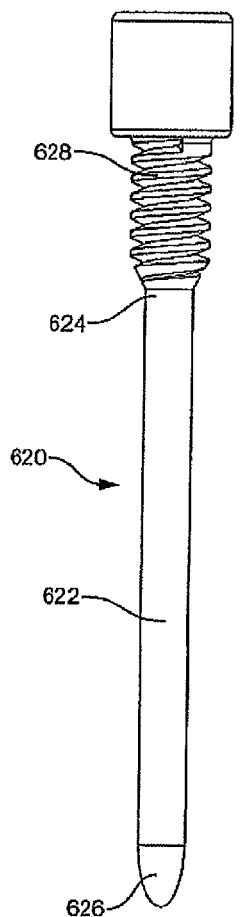
FIG. 37(C) is a side view of another insertion tool for installing a portion of a spinal stabilization system in accordance with an embodiment.
Figure 37B:
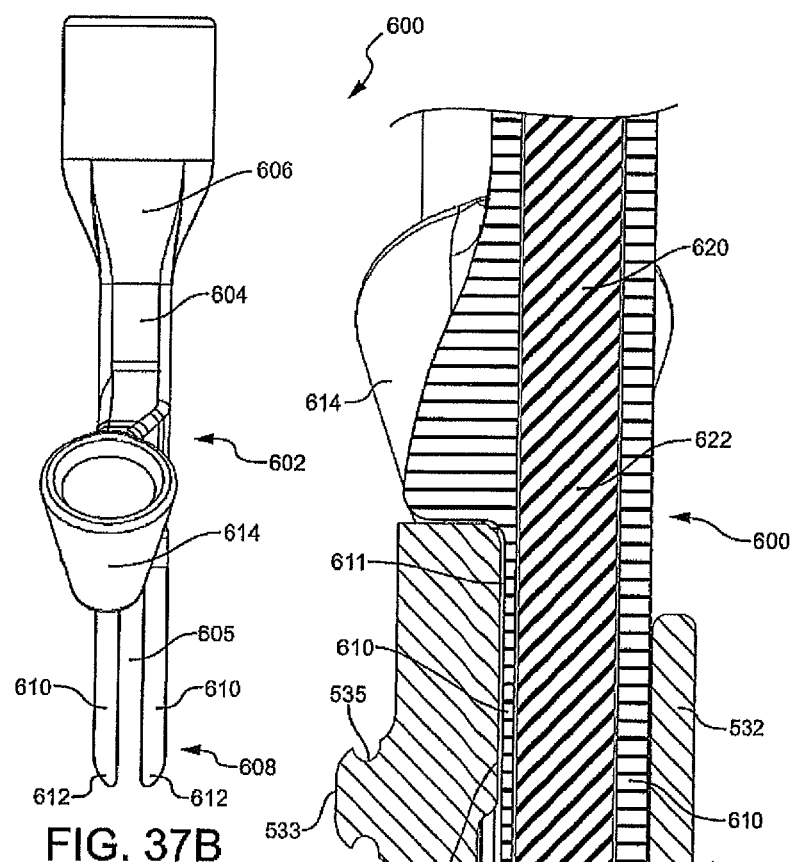
FIG. 37(B) is a side view of an element of an insertion tool for installing a portion of a spinal stabilization in accordance with an embodiment.
Figure 37D:
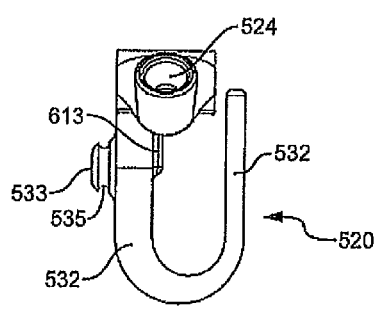
FIG. 37(D) is a side sectional view of the element of a spinal stabilization system and the insertion tools therefor shown in FIGS. 37(A), 37(B) and 37(C), respectively.
Figure 37A:
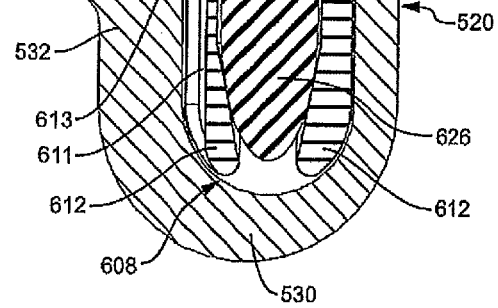
FIG. 37(A) is a side view of an element of a spinal stabilization system insertion tool in accordance with an embodiment of the present invention.
Figure 38:
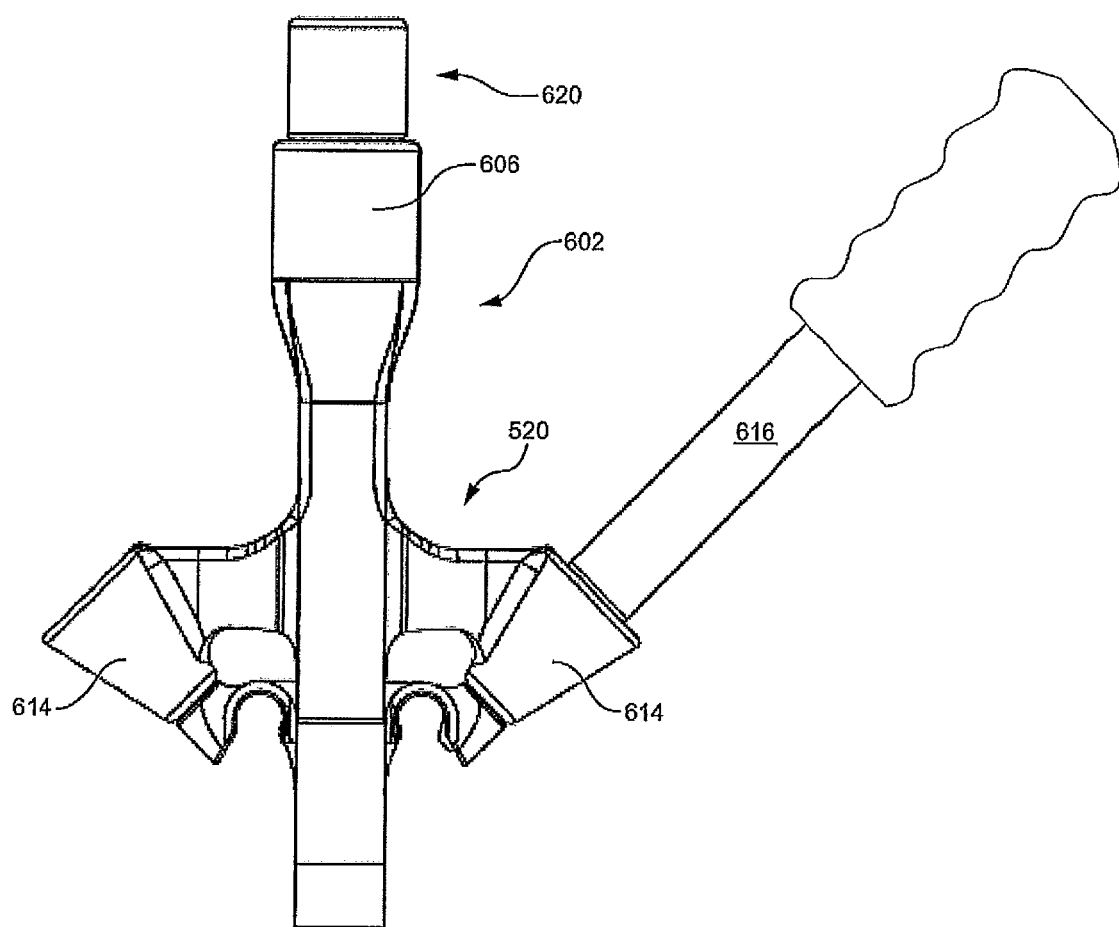
FIG. 38 is a top view of the insertion tool of FIG. 37(A)-(D) shown in operative engagement with an element of a spinal stabilization system in accordance with an embodiment of the present invention.
Figure 39:
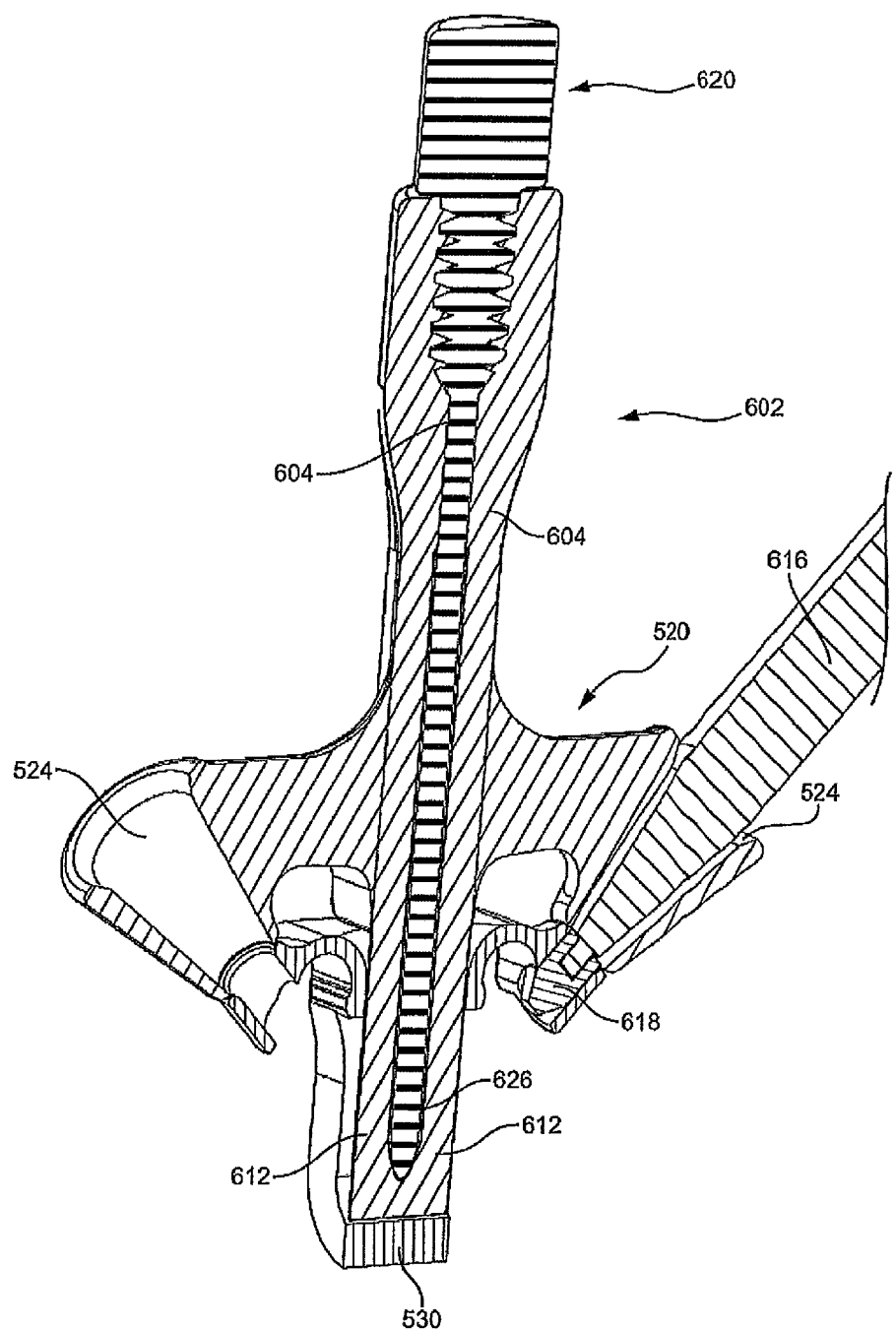
FIG. 39 is a sectional perspective view of the insertion tool shown in FIG. 38.

Referring now to FIGS. 37-39, a spinal stabilization system insertion tool apparatus, for ease of reference also referred to herein as a seating tool, adapted to install an interlaminar support member 520 (FIG. 34) is shown generally at 600.

Apparatus 600 comprises a first tool 602 including a cylindrical body portion or cannulated shaft 604 having an internal aperture 605 extending substantially longitudinally the length thereof. The body portion further includes proximal and distal ends 606, 608, the distal end comprising a pair of spaced apart longitudinally extending segments 610 each terminating in a rounded or tapered end portion 612 structured and arranged to be releasably inserted into the support member 520, as shown in FIG. 37(0). One of the segments 610 includes and alignment member 611 extending the length thereof, the alignment member being structured and arranged to cooperate with a guide member 613 formed in the interlaminar support member 520 to align insertion tool apparatus 600 properly therein for precise insertion of the interlaminar member into a spinal column. Interlaminar support member 520 also includes a second alignment feature which is illustrated in the form of a knob or extension 533 having a channel or recess 535 extending circumferentially thereabout, the knob and channel being adapted to receive portions of an installation apparatus, which will be discussed in greater detail below.

As shown in greater detail in FIGS. 37(8), 38 and 39, tool 602 includes at least one alignment guide 614 secured thereto and structured and arranged to be in operative alignment with an aperture 524. The alignment guide is adapted to receive a fastener installation tool 616 for installing a set screw or other fastening means 618 into the aperture 524 of the support member.

Referring again to FIG. 37, and specifically to FIG. 37(C), a second seating tool 620 according on embodiment is shown which includes a body portion 622 having a proximal end 624 and a distal end 626, the distal end being tapered for ease of insertion into the internal aperture 605 of first tool 602. The proximal end of the second tool includes a threaded portion 628 adapted to be threadably received by corresponding mating internal threads inside the proximal end 606 of the first tool 602 so that upon insertion of the body portion 622 of the second tool into the internal aperture 605 and in response to rotation thereof via a handle 630 secured to the proximal end of the second tool, the tapered end 626 engages each of the end portions 612 forcing them into locking engagement with the interlaminar support member 520 as shown in the side sectional view of FIG. 37(0). The support member may then be delivered to and inserted into the implantation site in a spinal column, and the set screws 618 may be inserted in alignment guides 614 and apertures 524 and tightened by tool 616. After the insertion and securing operations are completed, the second tool may be removed from the first tool by backing out the threaded portion, thereby releasing the grip of the ends 612 on the support member and permitting removal of the insertion tool apparatus from the support member.

Figure 40:
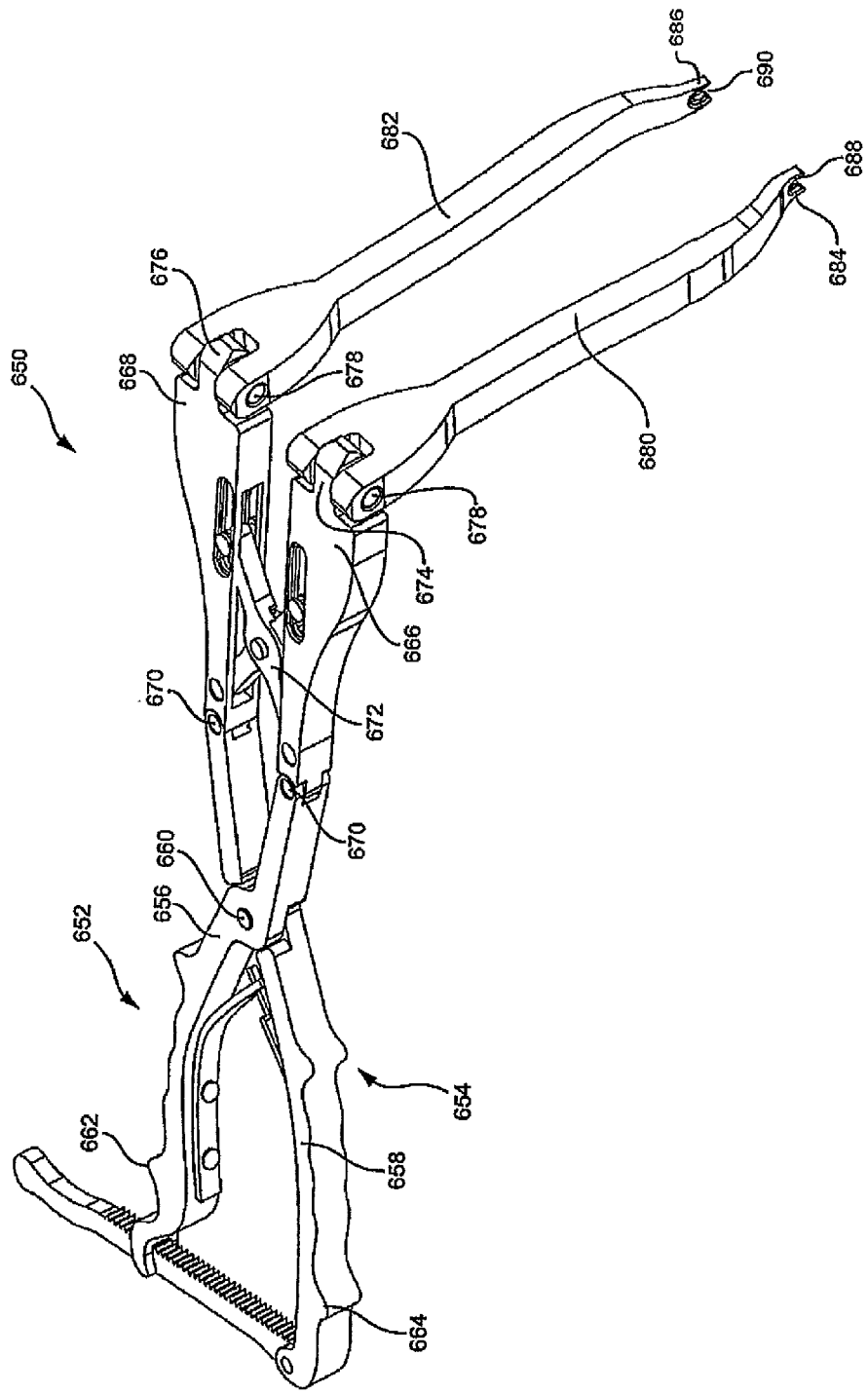
FIG. 40 is a top perspective view of a spinal stabilization system insertion tool in accordance with an embodiment of the present invention.
Figure 41A:
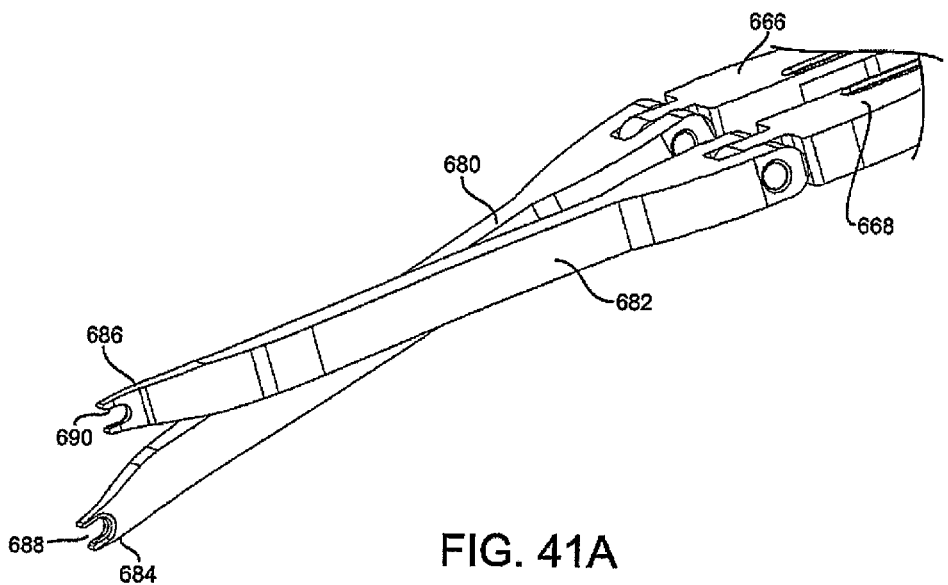
FIG. 41(A) is a perspective view of portions of the insertion tool shown in FIG. 40.
Figure 41B:
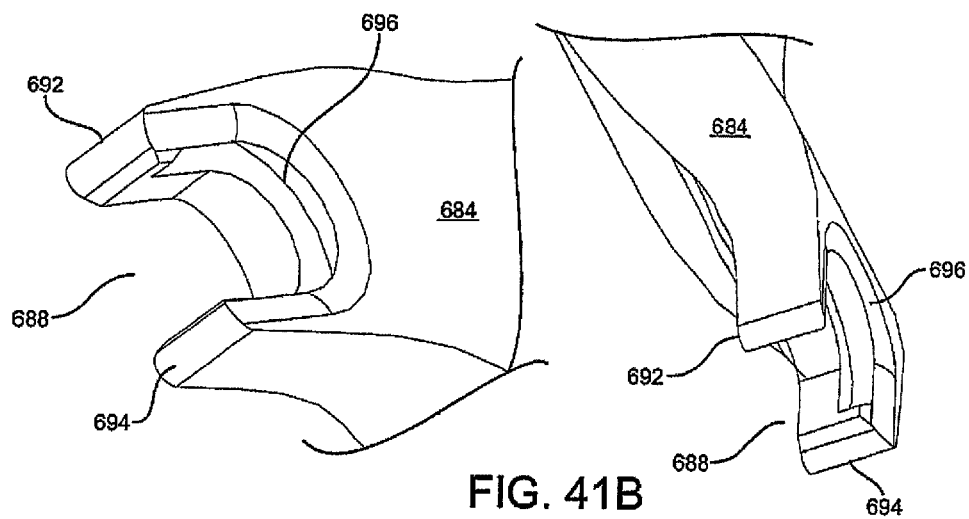
FIG. 41(B) is an enlarged perspective view of portions of the insertion tool shown in FIGS. 40 and 41(A)

Referring to FIGS. 40, 41(A) and 41(B), a third plier-like tool for inserting a spinal stabilization system configured in accordance with the structure of the system 10 shown in the embodiment of FIG. 1 is illustrated at 650. In the configuration shown, the tool is designed to deliver parallel compressive forces to displace on member of the system a distance closer relative to another component. Alternatively, the tool may be configured to deliver distractive forces to system components whereby one component of the system is displaced a distance further relative to another component.

Tool 650 includes first and second arms 652, 654, each arm having a body portion 656, 658 pivotally interconnected at a midpoint 660 thereof, a first end portion or handle 662, 664 and a second end portion 666, 668, each second end portion being pivotally pinned to a respective body portion by a pin 670. The second end portions 666, 668 are structurally supported and cross linked to one another by a linkage mechanism, and each further includes an ear or bracket member 674, 676 extending longitudinally outwardly therefrom, each ear being adapted to receive a pin 678 for rotatably mounting an arm 680, 682 thereto respectively. Each arm includes a distal forked end portion 684, 686 having an aperture or recess 688, 690 formed therein, each recess being structured and arranged to releasably engage a portion of the spinal stabilization system 10 for installation thereof on a patient's spinal column.

Referring to FIGS. 41(A) and 41(B), one forked end portion, end 684, is shown enlarged so that the features thereof may be understood in greater detail. Each end includes a pair of finger-like members 692, 694 extending outwardly therefrom and general parallel to one another to form the aperture 688. The end portion further includes a recess 696 which extends circumferentially around the aperture and is adapted to receive a retainer, by way of example and not of limitation, a snap ring or other retaining device as is known in the art, to secure the end 684 to a portion of a spinal stabilization system for purposes of installation. By way of further example, aperture 688 and fingers 692, 694 are adapted to fit over knob 533 and recess 535 on interlaminar support member 520 shown in FIG. 37 (A) and to cooperate therewith to achieve precise positioning and insertion of member 520 into a spinal column.

FIGS. 42(A) and (B) illustrate the elements of a fourth tool or rod reducer 700 structured to be used in conjunction with the third tool 650 and to cooperate therewith in the procedure of installing a spinal stabilization system 10. Similar in construction to the first tool 602, the fourth tool includes a cylindrical body portion or cannulated shaft 702 having an internal aperture 704 extending substantially longitudinally the length thereof. The body portion further includes proximal and distal ends 706, 708, the distal end comprising a pair of spaced apart longitudinally extending arms 710 each terminating in a curved or hooked member 712 structured and arranged to releasably engage a portion of the support system 10.

FIGS. 42(A)-(B) illustrate a moveable rod member 720 which cooperates with cannulated shaft 702 to form the rod reducer 700. The rod member includes a body portion 722 having a proximal end 724 and a distal end 726, the distal end being rounded or tapered for ease of insertion into the internal aperture 704 of shaft 702. The proximal end of the rod member includes a threaded portion 728 adapted to be threadably received by corresponding mating internal threads 730 inside the proximal end 724 of the cylindrical body portion 702 so that upon insertion of the body portion 722 of the rod member into the internal aperture 704 and in response to rotation thereof via a handle 732 secured to the proximal end of the rod member, the tapered end 726 cooperates with hooked members 712 to engage and align an element of the spinal stabilization system for installation on a spinal column, as will now be set forth with greater specificity.

Referring to FIGS. 43-46, a method of installing a spinal stabilization system 10 using the installation apparatus and tools hereinabove described and the operating interrelationship and cooperation of the tools during the installation will now be described. As a general background introduction, after the vertebrae in the portion of a spinal column have been identified and exposed by a surgeon, an implant trial is used to determine an appropriate fit of an implant. Implant trials of increasingly larger size may be delivered into the implantation region until an implant trial is chosen that appropriately fits the various surfaces of the implant trial against the bony surfaces of the lamina and spinous process. The implant trial may be forcibly delivered into the implantation region by using a hammer or mallet to strike an impact plate (not shown) at a proximal end of the tool. Numerous trials and templates corresponding to various configurations and dimensions of the components of the implant systems may be used during the course of the procedure in order for a surgeon to select the appropriately dimensioned and configured implant system best suited to a particular patient.

Prior to surgical site or bone preparation, trial insertion, or implant placement, a surgeon or other medical person may select a suitable procedure to fixation or stabilize a portion of the spinal column. The procedure may include fusing the intervertebral joints with or without delivering an implant in the joint space, e.g., an intervertebral body fusion device ("IBFD"). The procedure may alternatively or additionally include placing pedicle screws or hooks in operable relation with spinal rods thereby forming a construct to which embodiments of the present disclosure may be operably coupled. If the surgeon selects a procedure involving delivery of an implant as disclosed herein up to and in engagement with a portion of the spinal column, the surgeon may select an implant configuration for delivery into the posterior aspect of a vertebral column of the patient including attachment to both a spinal lamina and a pedicle screw and spinal rod construct based on preoperative or intraoperative data. The data may be the result of post-processing of raw or other imaging data (e.g., CT or MRI DICOM files). The post-processing may include the use of a software program (e.g., 3DSL1CER available from http://www.slicer.org) that may be used for medical image processing and visualization of image data. Other data may include the patient's weight, activity level, and general health.

The preoperative or intraoperative data may assist in the planning and selecting of desirable procedure trajectories (e.g., starting and stopping points on patient's soft tissue and near or within bone tissue), implant component types and dimensions (e.g., lengths, heights, widths, diameters, thread pitches, and angles relative to other components), delivery tool configurations and dimensions, and bone preparation tool types, dimensions, and configurations. A particular system for preparing and stabilizing the portion of the vertebral column may be selected, for example, for a hypermobile segment, which may include one or more implant components or the entirety of the system that is resistant to the expected forces present at that particular patient's spinal segment. The determination of fixation or stabilization sufficiency may be calculated based on the patient's data and also on the performance results of various bench and/or finite element analysis ("FEA")—tested implant assembly configurations. For example, a calculated implant and/or screw trajectory may be considered and determined from certain patient imaging and post-processing data with an overlaid implant assembly. Further, the implant assembly may be selected to include a first and a second interlaminar component dimensioned and configured to extend as far anteriorly toward the spinal canal as possible in order to center the interlaminar components as close to the center of the spinal column's axial compressive loading and in order to increase total implant surface to bone surface contact area to better distribute the loading of the spine over a lower percentage of the total joint surface. This load distribution reduces the possibility of spinous process fractures and other complications.

Specific measurements and characteristics of the patient's anatomy may influence the selection of a particular system or its components. For example, the patient's bone density may be measured at numerous locations in proximity to and surrounding the elements of the implant assembly. Lower bone density (e.g., osteopenia, osteoporosis) corresponding to a T-score lower than −1, unstable spondylolistheses, or hypermobility may require the use of an implant assembly with a greater rigidity or more points of fixation to the bone and or spinal rods. Additionally, the relative angles between the implant surfaces and screw or screws, and also the relative angles between multiple screws (e.g., parallel, divergent, convergent) may be preselected based on the patient's anatomy.

A comparison of the preoperative or intraoperative data (e.g., lamina and/or spinous process surface area, spinal segment mobility, loading, bone density, desirable anatomic pathways) and the selected implant assembly and bone preparation tools may be conducted to ensure or validate compatibility before the manufacture ships the implant system and/or before the surgeon employs the system in a surgical procedure. After validation of the implant assembly and preparation tools, the selected assemblies may be shipped to the surgeon and the surgeon may proceed with the surgical fusion procedure utilizing the selected assemblies.

In particular embodiments, pre-operative imaging may be used to manufacture custom implants to better match an individual patient's anatomy or to correct a structural misalignment of the spinal column. The various surfaces or faces of the implant may be selected to match the contour of the bone surface to which the implant surface will contact. For example, the surface or faces of the interlaminar components which contact the lamina and spinous process may be configured to be generally planar or even concave to match the contour of a bony surface including wrapping a portion of the surface around a greater portion of the lamina or spinous process. In one aspect, the faces or surfaces of the implant may be generally a surface negative of the surfaces to which said surfaces are desired to contact.

Figure 43:
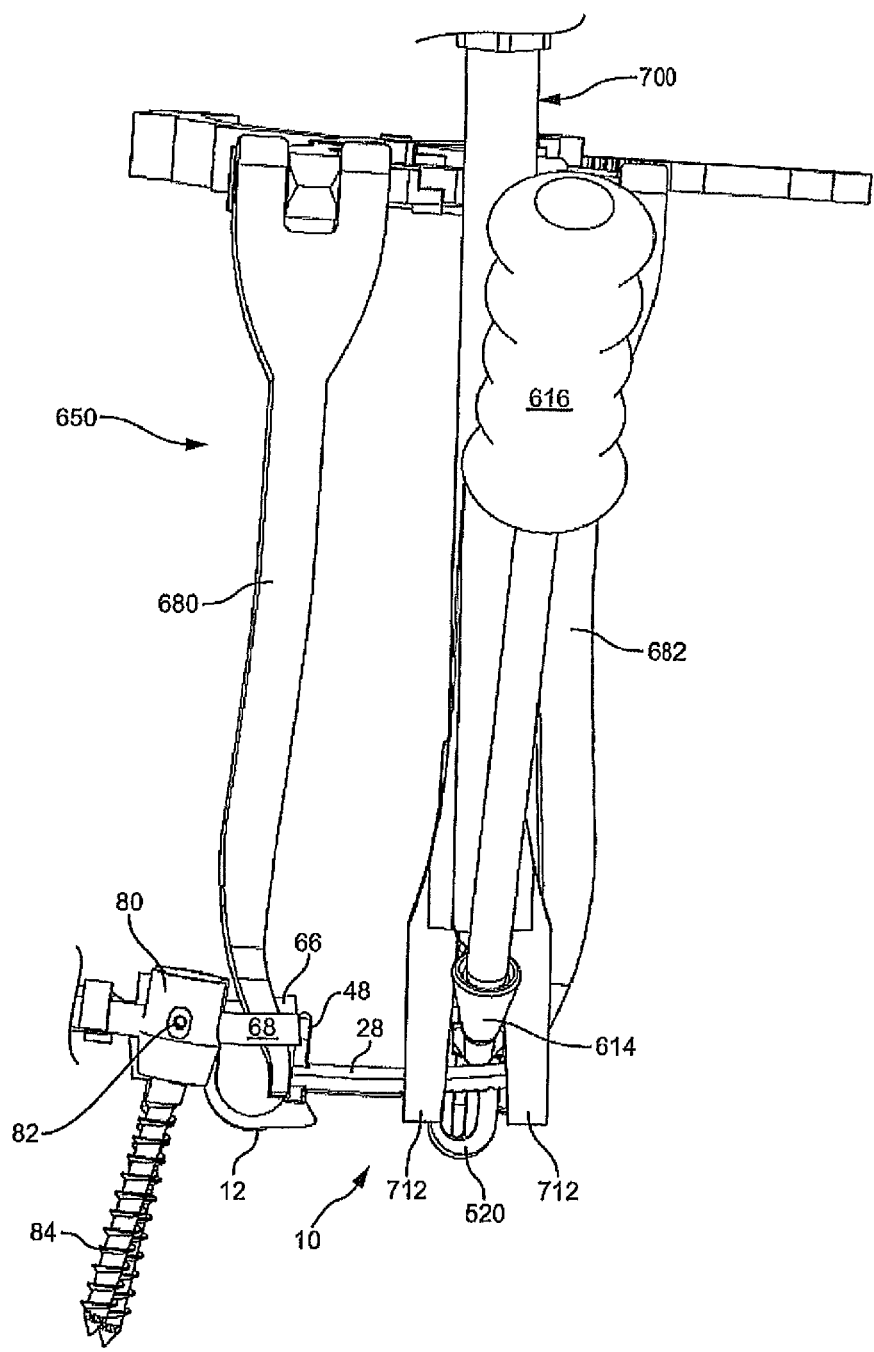
FIG. 43 is a side view of the insertion tools of FIGS. 37-42 shown in operative engagement with a spinal stabilization system in accordance with an embodiment of the present invention.

Referring now to FIG. 43, typically, a surgeon will employ a depth measuring device or a depth gauge (not shown), as is known in the art, to determine the depth from the guide rods 28 to the patient's spinal column so that the size of the interlaminar support member for the intended implant location may be determined accurately. A spinal stabilization system 10 is positioned at the desired location along the column at the insertion point. The spinal stabilization system 10 includes a first interlaminar member 12 adapted to be positioned between adjacent first and second vertebrae in a spinal column (FIG. 6) and a second interlaminar member 520 adapted to be positioned between the second vertebra and a third vertebra therein. Both the first and second interlaminar members are operatively interconnected with one another via support members or guide rods 28.

A first step entails the installation of pedicle screws 84 and securing devices 80 attached to each at the proper locations in a spinal column. Guide rods 66, 68 may then be inserted into a respective securing device 80 and secured thereto by set screws 82. At this point, any lamina and/or spinal process may be removed as necessary to decompress the vertebrae and measurements may be taken as described above. A transverse member (58 in FIG. 1) may then be attached to the spinal or guide rods 66, 68, and a first interlaminar support member 12 may be placed at the desired location along the spinal column. The set screws 82 securing the guide rods 66, 68 are tightened, and lateral images and depth gauges are employed to measure the distances required for precise insertion of the interlaminar member. Similar measurements are made for the second interlaminar member 520 and it is positioned over the spinal column at the intended insertion point.

Figure 44:
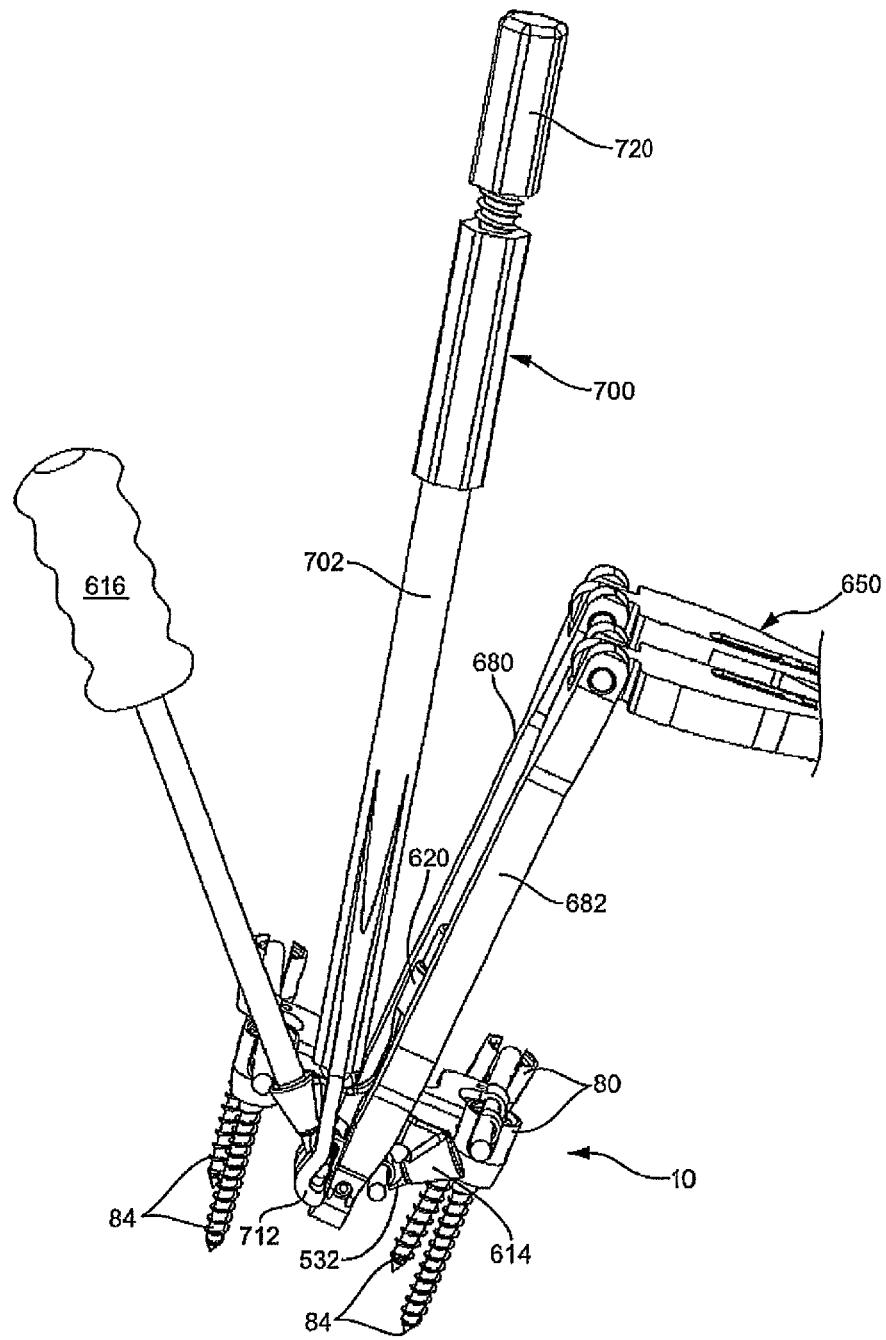
FIG. 44 is a side perspective view of the insertion tools shown in FIG. 43.
Figure 45:
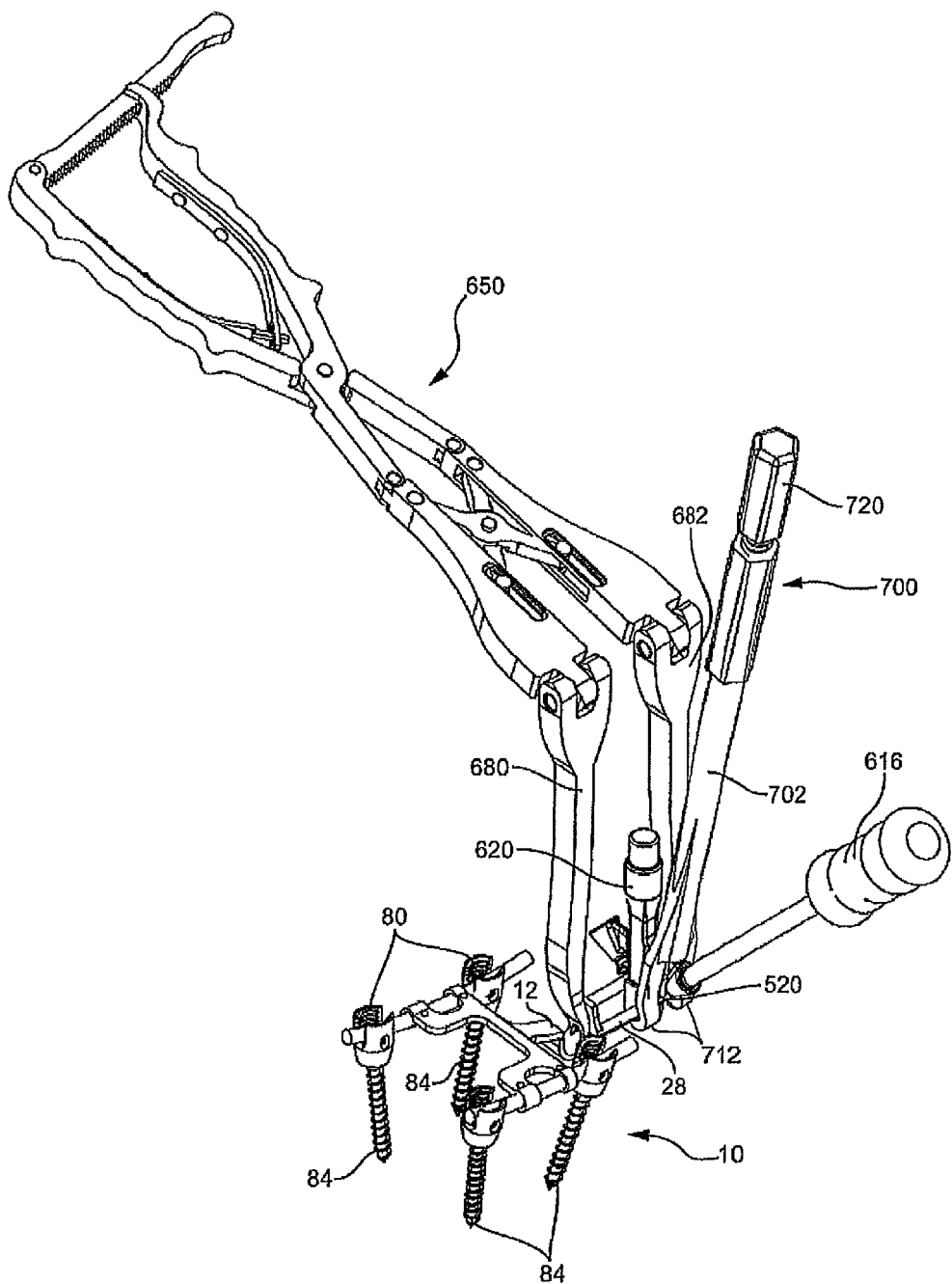
FIG. 45 is a top perspective view of the insertion tools shown in FIGS. 43 and 44.

Referring now to FIGS. 44 and 45, rod reducer tool 700 is attached to one of the guide rods 28 with arms 710 positioned on either side of the interlaminar member 520 thereby straddling it and each hooked member 712 operatively connected to the guide rod. By rotating handle 720, tool 700 aligns guide rod, interlaminar member 520, set screw alignment guide 614 and the patient's spinal column properly for precise insertion of the member therein and installation and tightening of a set screw or other suitable fastening means by tool 616, as will be described below.

At this time, compression/insertion tool 650 is attached to the stabilization system 10 with one forked end 684 in operative engagement with leg member 48 of interlaminar member 12, and the other forked end in operative engagement with knob 533 and recess 535 on interlaminar member 520, whereby upon activation of the repressor 650, either compressive or distractive forces are applied to each of the interlaminar members 12 and 520 to position them along rods 28 at a preferred spacing as determined by the measurements taken earlier.

Figure 46:
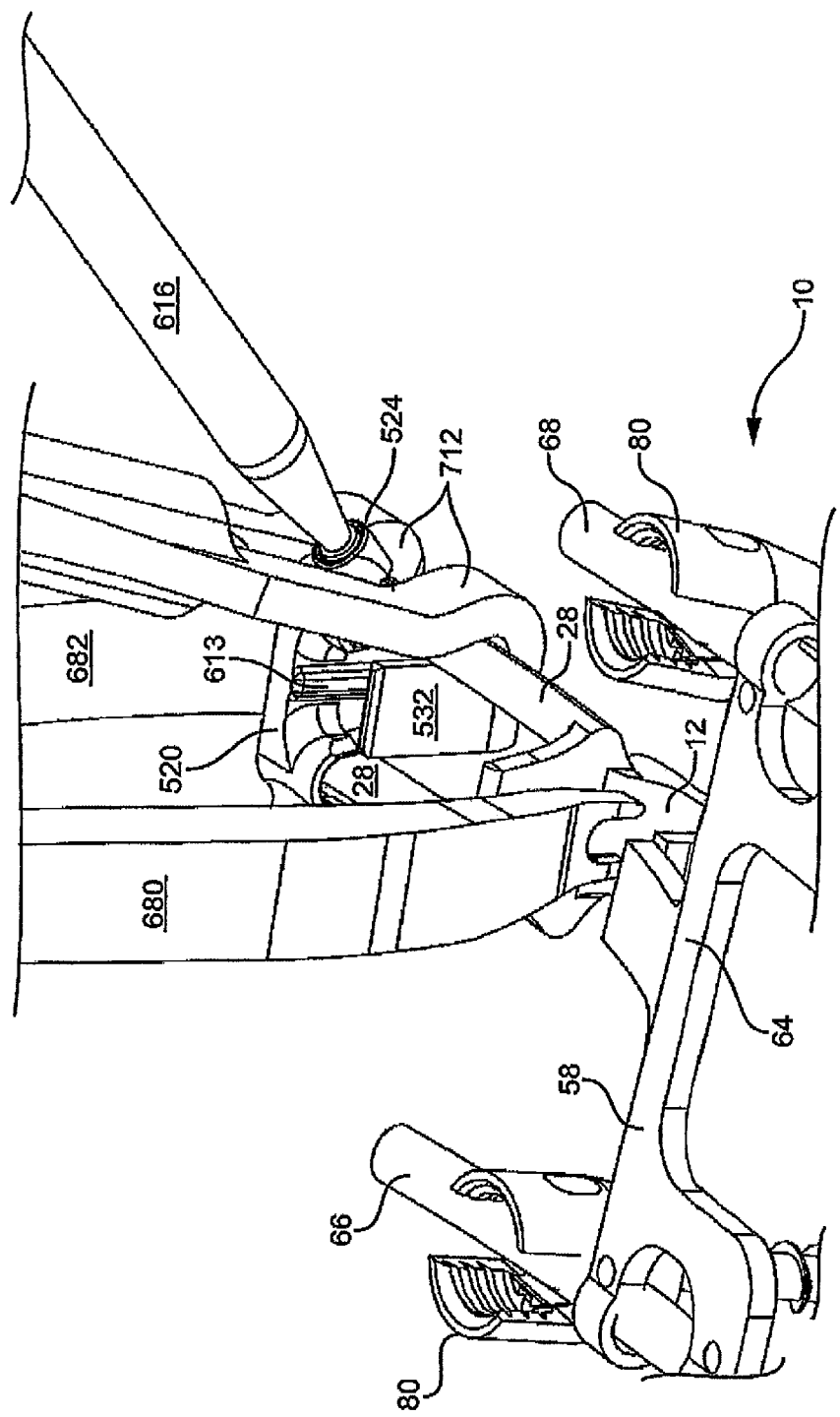
FIG. 46 is an enlarged perspective view of portions of the tools of FIG. 45.

The seating tool 620 is now positioned over alignment guide 613 in support member 520, as best viewed in FIG. 46, and secured thereto by expanding members 612 into operative engagement with the interlaminar support member. The support member may then be delivered to and inserted into the implantation site in a spinal column, and the set screws 618 may be inserted in alignment guides 614 and apertures 524 and tightened by tool 616. After the insertion and securing operations are completed, the various tools may be removed from the support member and other elements of the spinal stabilization system and the incisions may be sutured to begin the patient's healing and recovery process.

Figure 47:
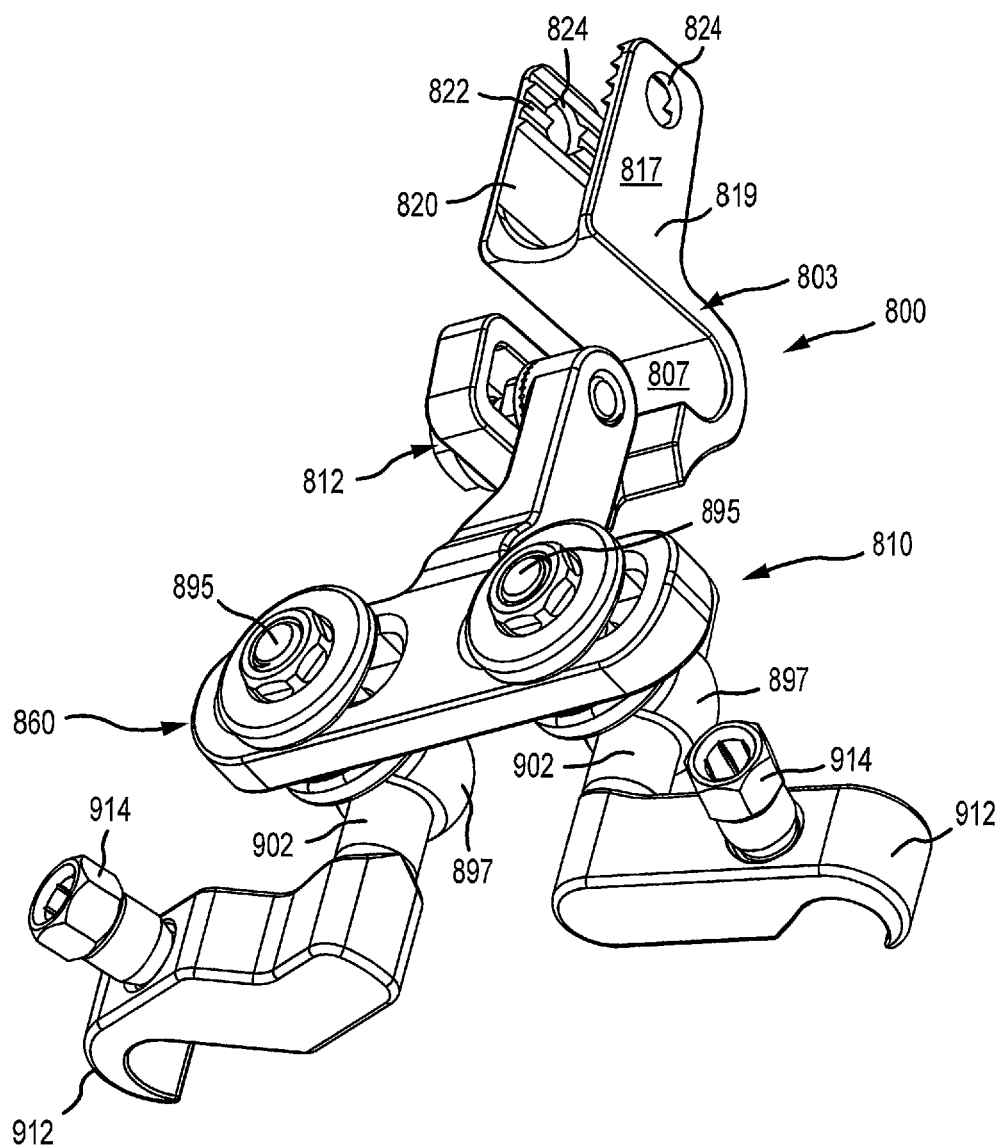
FIG. 47 is a bottom perspective view of a spinal stabilization system in accordance with an embodiment of the present invention.
Figure 48:
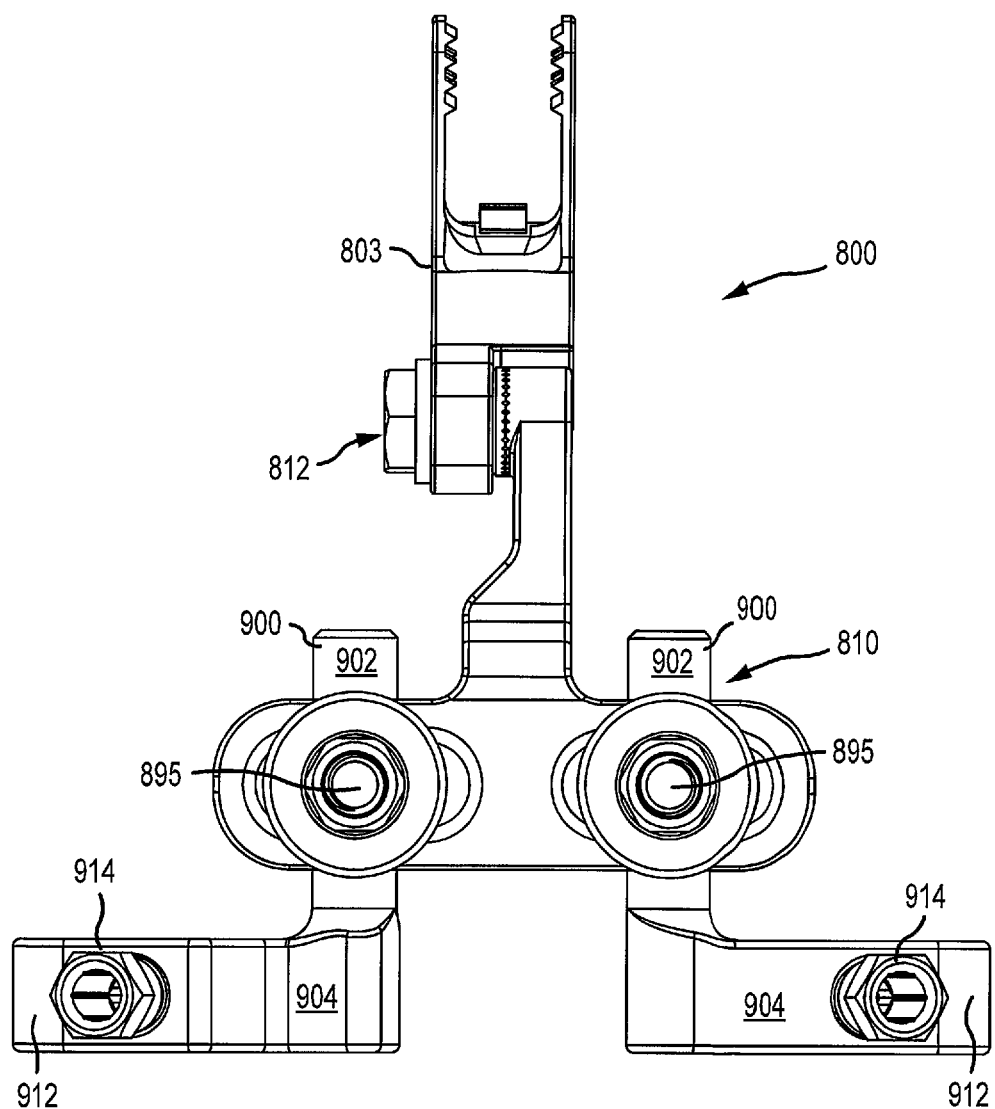
FIG. 48 is a front plan view of the spinal stabilization system of FIG. 47.
Figure 49:
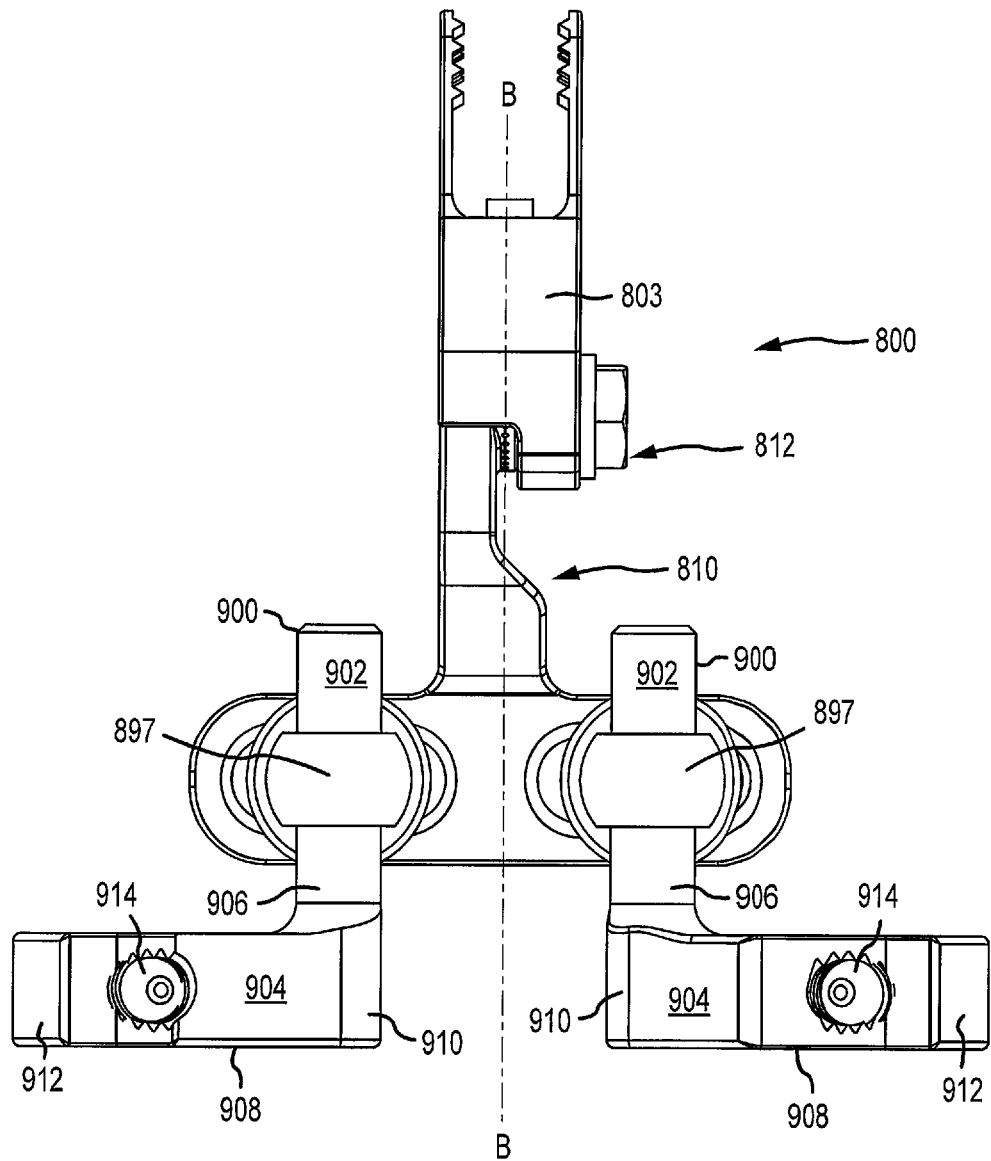
FIG. 49 is a rear plan view of the spinal stabilization system of FIGS. 47 and 48.

Referring now to FIG. 47-49, an adjustable spinal stabilization system according to another embodiment of the present invention is shown generally at 800. The system includes an interlaminar member 803 adapted to be positioned between adjacent vertebra in a spinal column. As shown in greater detail in FIGS. 54-56, the interlaminar member is shown positioned between a first vertebra 12 and a second adjacent vertebra 16 in a spinal column 18.

Figure 53:
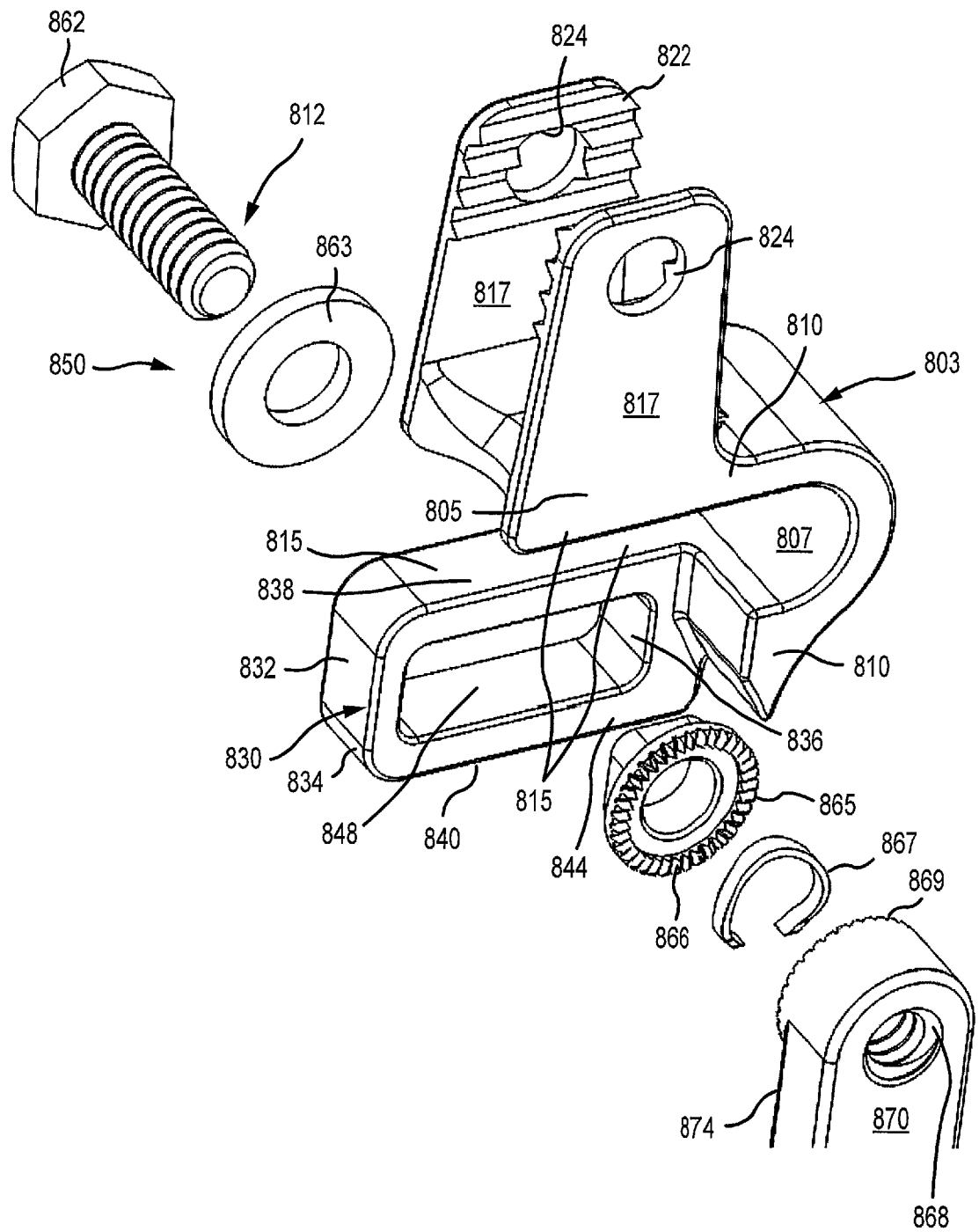
FIG. 53 is an exploded top perspective view of the portion of the spinal stabilization system of FIGS. 50-52.
Figure 54:
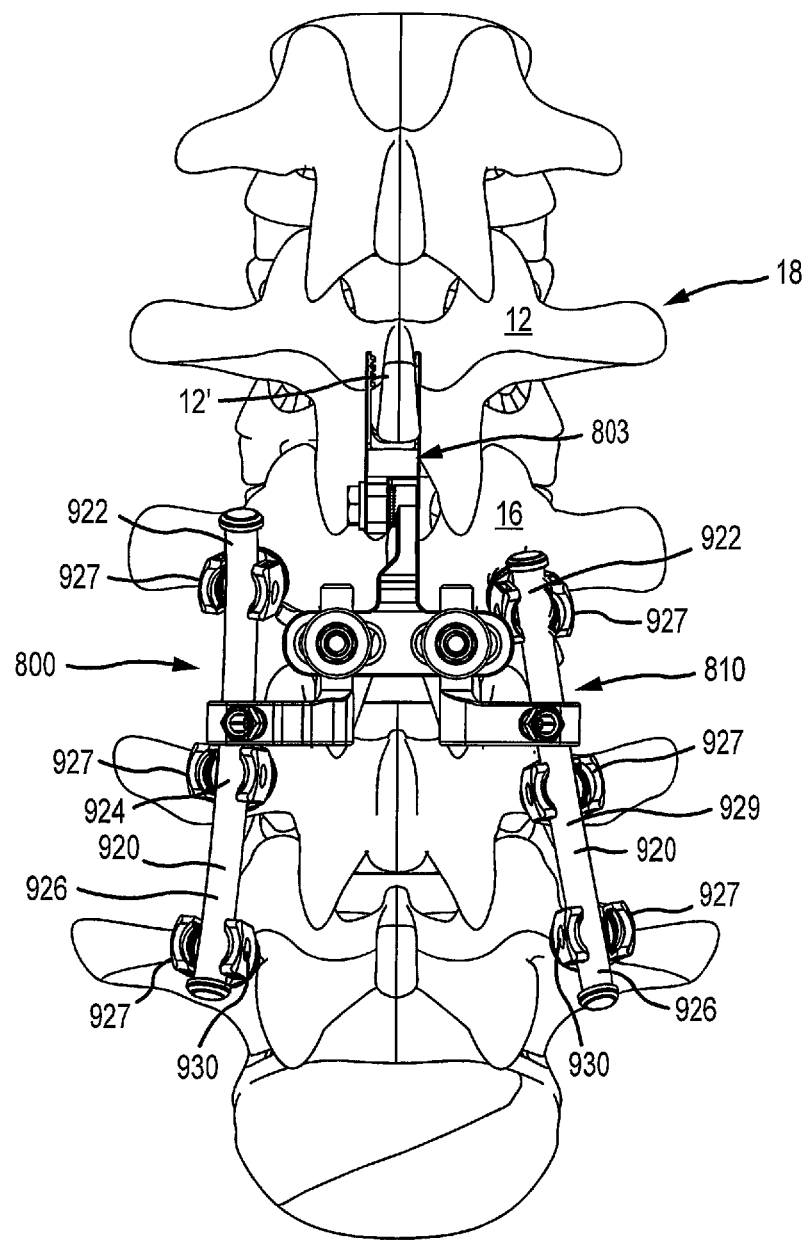
FIG. 54 is a front plan view of the spinal stabilization system of FIGS. 47-49 shown affixed to a spinal column.
Figure 55:
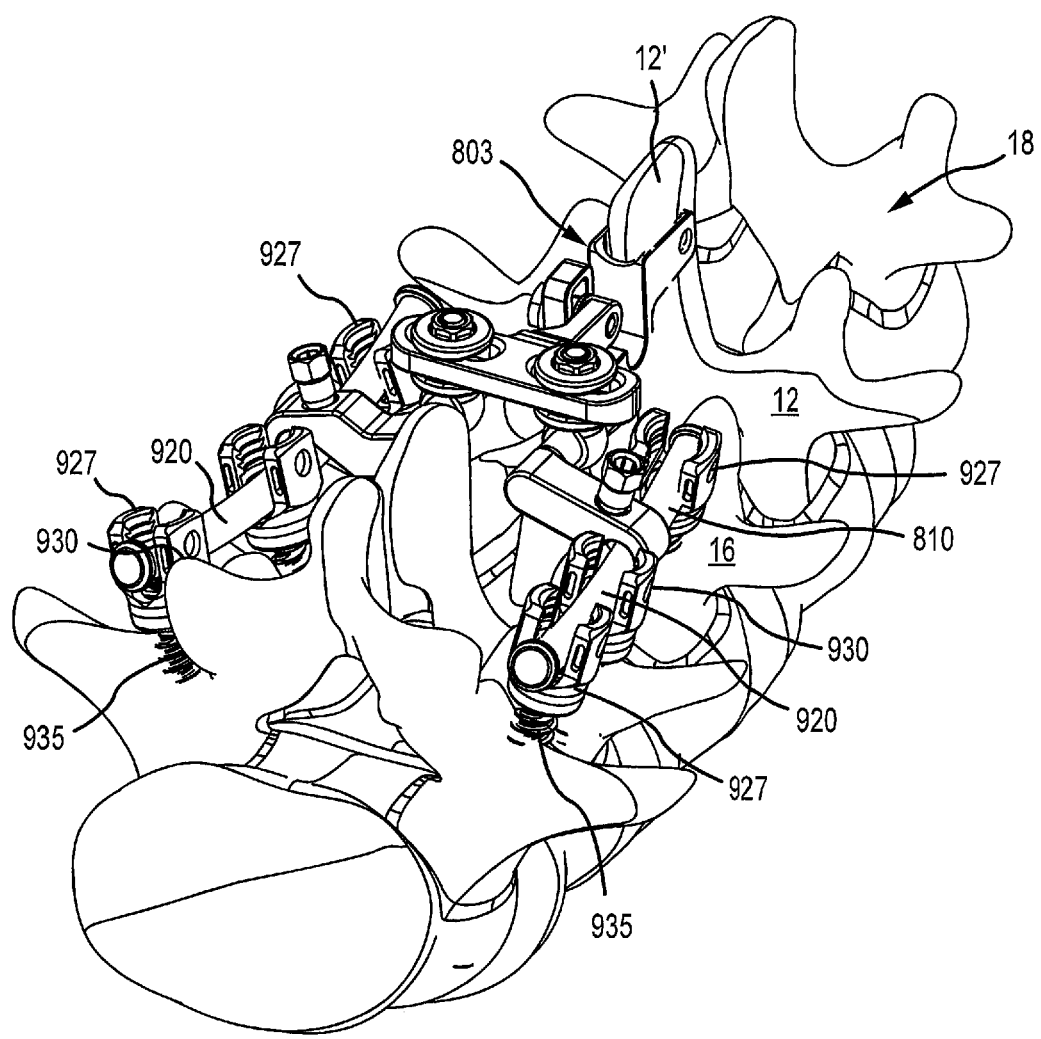
FIG. 55 is a bottom perspective view of the spinal stabilization system of FIG. 54.
Figure 56:
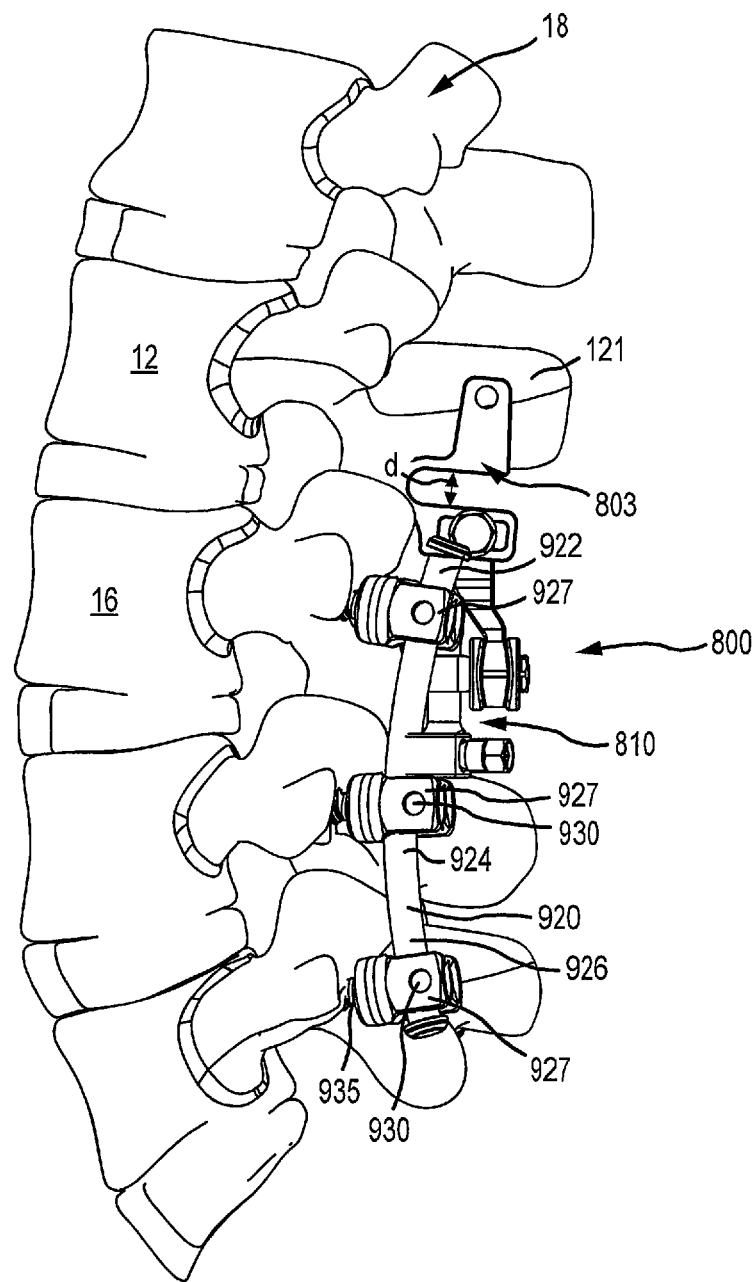
FIG. 56 is a side plan view of the spinal column of FIGS. 54 and 55.

The interlaminar member is operatively connected to a support structure 810, portions of which are shown generally at numeral 810 in FIG. 47, the entire support structure being illustrated in FIGS. 54-56. By way of example, in the embodiment shown, the support structure and the interlaminar member may formed from material such as titanium or stainless steel suitable for use as a medical implant device and are operatively adjustable interconnected by a threaded fastener assembly 812, the specific elements of which are illustrated in greater detail in FIG. 53 and will be described in greater detail below. However, it is to be understood that other means for connecting the interlaminar device to the support structure such as hinges, pins, and the like may also be used without departing from the scope of the invention.

Referring now to FIGS. 50-53, the interlaminar member 803 is shown in greater detail. The interlaminar member comprises a body 805 defined by an elastic midsection 807, the elasticity of which may be adjusted by material property selection and/or size, two spaced apart end portions 810, and a pair of juxtaposed legs 815, each leg extending substantially parallel to one another from one of the respective ends in a direction generally outwardly away from the spinal column 18 (FIG. 56) and spaced apart a preselected distance d. Distance d is determined by the size of the interlaminar member 803, which is, in turn, may be selected based upon the spacing between the first and second vertebrae 14 and 16, respectively. Depending upon the situation, the interlaminar member may be intended to fuse the first and second vertebrae, or it may be intended to permit limited motion therebetween while at the same time maintaining the stability of vertebra 16 relative to vertebra 14. Accordingly, it may be sized to be a tight fit, and the elastic properties of the body 805 act as a spring or shock absorber in the interface between the two vertebrae. In the embodiment shown in the above-referenced figures, the elastic midsection 807 of the body 805 is U-shaped. However, as noted above with respect to other embodiments, other shapes or configurations, by way of example, a V-shape, a W-shape, a S-shape or other function configurations may also be used effectively.

The interlaminar member 803 further includes a pair of spaced-apart support members or plates 817 secured to an upper one of the pair of juxtaposed legs 815 of the interlaminar support member 805 and extending in a direction upwardly therefrom substantially parallel to one another. Each of the plates includes an outer surface 819 and an inner surface 820, each inner surface having a plurality of teeth 822 formed therein and extending substantially parallel to one another in a direction generally cranially along the spinal column 18 (as shown in FIGS. 54-56) or alternatively if the assembly is flipped to support a vertebra below the spinal construct, caudally along the spinal column (not shown). Each support member or plate 817 further includes an aperture 824 formed therein and coaxially aligned along axis A-A, the apertures and the plates cooperating with one another to be positioned adjacent opposite sides the spinous process 12' of vertebra 12 and to be secured thereto by a suitable fastener, such as, by way of example, a bolt, a screw or the like. According to other aspects, the intralaminar member may be fixed or otherwise attached to the spinous process or lamina by having a configuration as shown and described throughout the present disclosure, as shown in any of the referenced provisional applications, or any other means or mechanism know in the art, e.g., a pair of brackets flared out laterally dimensioned to receive laminar screws, tethers, clamps, wires, latches, etc.

As best shown in FIG. 53, the interlaminar member further includes an attachment member 830 operatively connected to a lower of the two spaced apart end portions 810 and the legs 815 of the body 805. In the embodiment shown, the attachment member includes a generally rectangular body 832 extending in a downward or caudal direction therefrom. The body includes first and second end portions 834, 836; top and bottom body portions 838, 840 and generally parallel, oppositely disposed first and second side portions 842, 844 extending intermediate the first and second end and side portions respectively. The body includes an aperture 848 formed therein adapted to receive a fastening apparatus 850 for securing the interlaminar member to a support structure 860, which will be described in greater detail below. As shown, the attachment member 830 is connected to the lower of the two spaced apart end portions offset from the center; however, in other aspects it may be connected centrally and the leg 882 may in an aspect be configured as a clevis and may be located on both sides of the attachment member 830 or vis versa where the attachment member 830 comprises a pair of attachment members spaced apart from one another to receive the leg 882 therebetween. In the embodiment shown, the fastening apparatus includes a bolt 862, a washer 863, a lock nut 865 having serrated teeth 866 formed thereon and a squared portion opposite the face having the serrated teeth and a spacer spring 867. The bolt is structured and arranged to be inserted through the washer and then through the aperture 848 in the body of the attachment member and then through the lock nut and spacer spring whereupon it is threadably inserted into a mating female threaded aperture 868 formed in an end 870 of a portion or member 872 of the support structure 860. The end has serrated teeth 869 formed on an inner surface 872 thereof, the teeth being adapted to engage the teeth 866 of the lock nut 865 whereby the proper orientation of the interlaminar member relative to a patient's upper spinous process may be attained and locked in place. The spacer spring 867 is configured to maintain a separation between the serrated teeth 869 and 866 in order to permit movement between the components until the components are locked thereby compressing the spacer spring which permits the serrated teeth pair to engage another to prevent movement. The squared portion of the lock nut 865 is configured to travel along a length of the aperture 848 and when the components are locked help prevent undesirable movement between the aperture and fastening apparatus 850.

Figure 50:
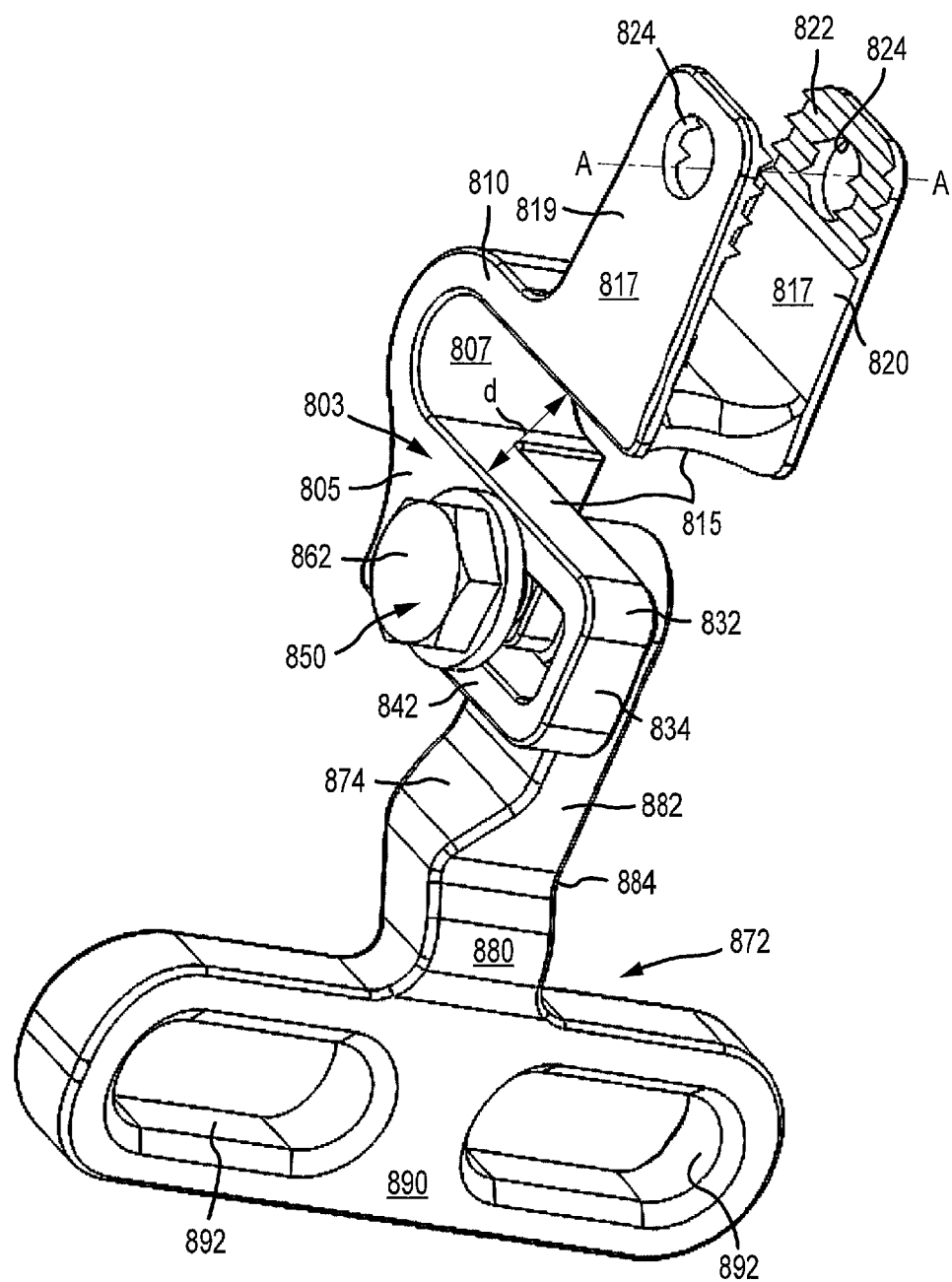
FIG. 50 is a top perspective view of a portion of the spinal stabilization system of FIGS. 47-49.
Figure 51:
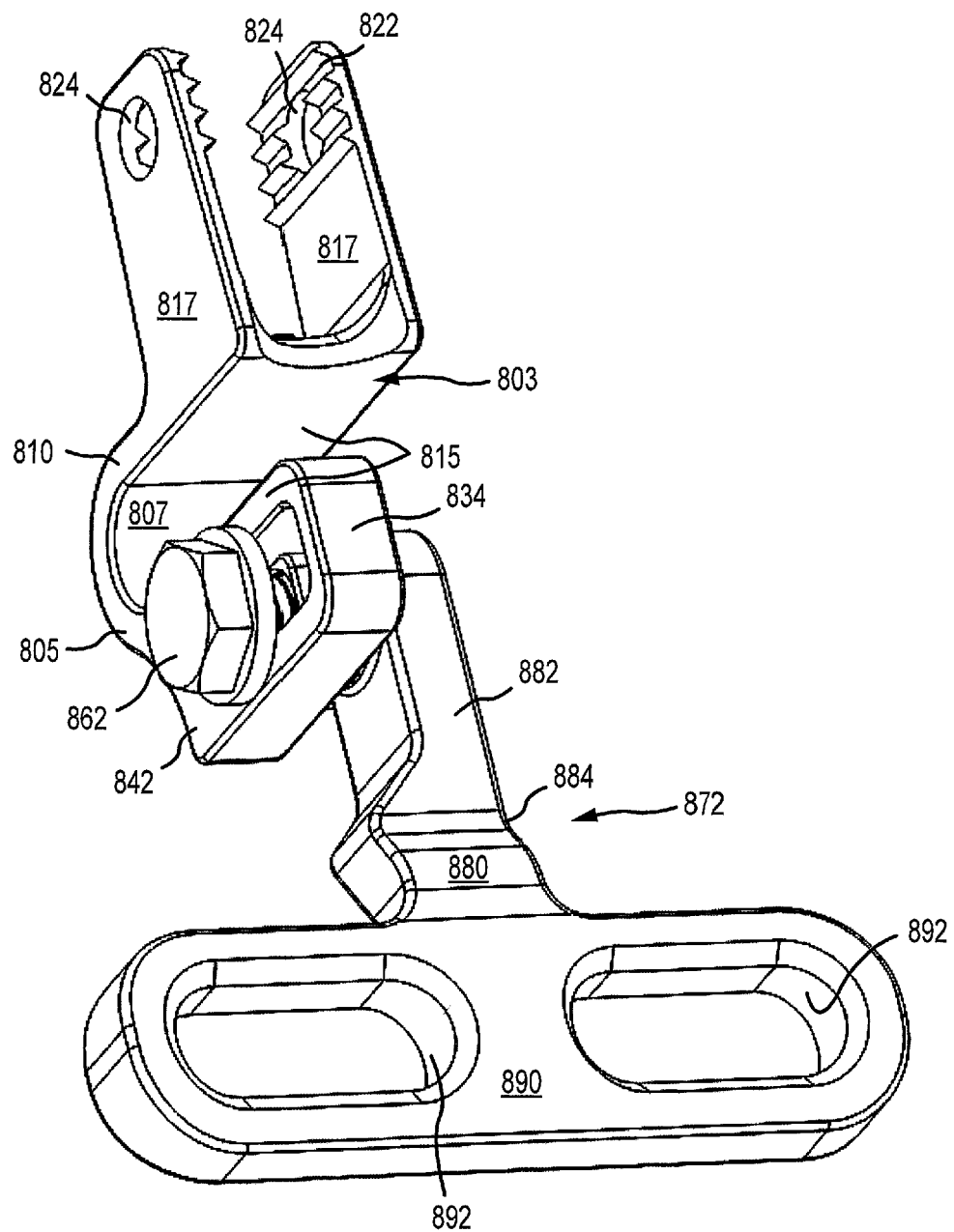
FIG. 51 is a bottom perspective view of the portion of the spinal stabilization system of FIG. 50.
Figure 52:
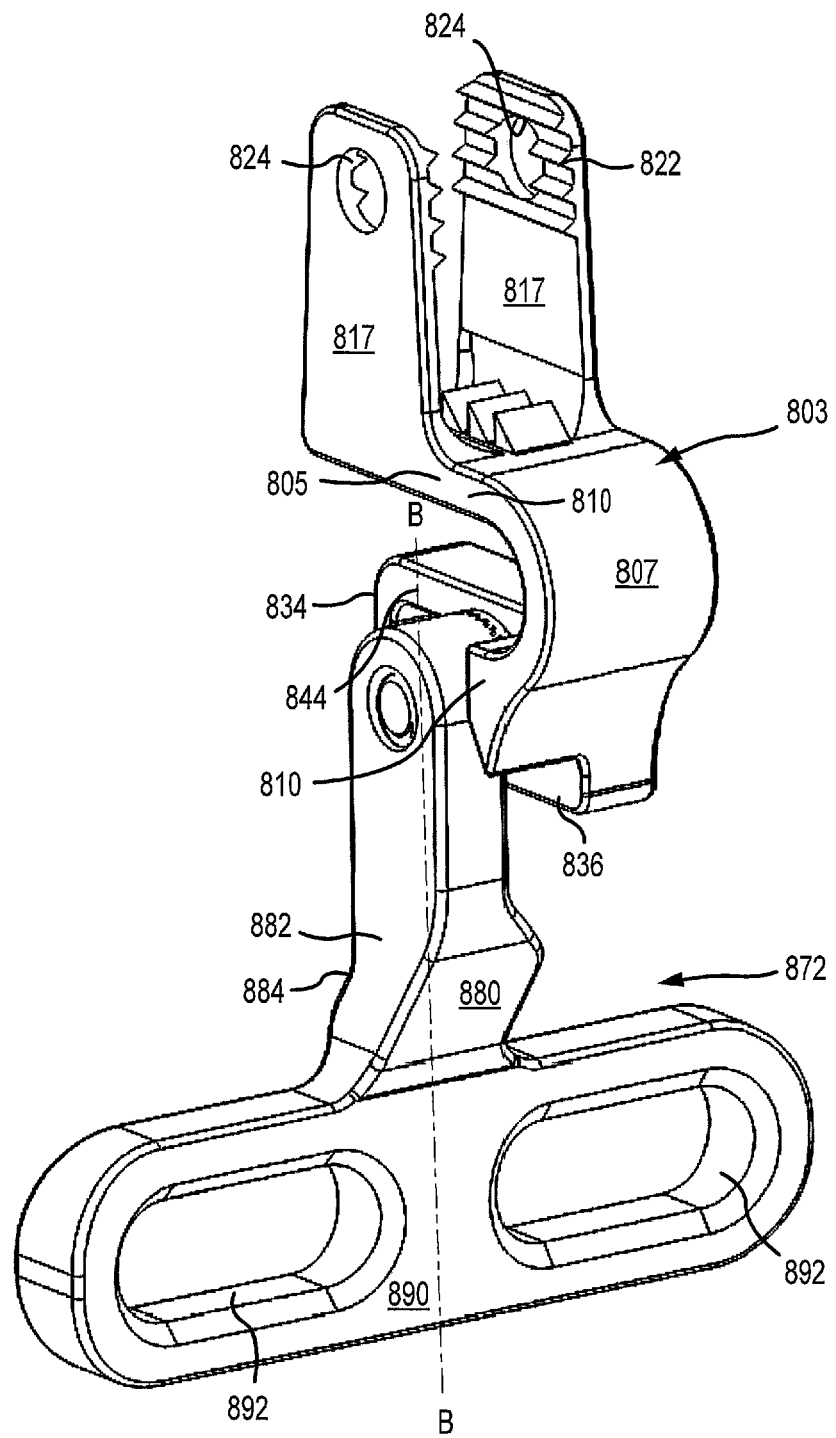
FIG. 52 is a rear perspective view of the portion of the spinal stabilization system of FIGS. 50 and 51.

Referring to FIGS. 50-52, member 872 of the support structure is shown in greater detail. It includes a generally T-shaped body portion 880 including an upwardly extending member or leg 882 which is formed to contain an angle 884 extending anteriorly toward the spinal column 18 to facilitate installation and adjustment of the stabilization system to accommodate a patient's skeletal structure. A crosslink member 890 is operatively connected to the leg 882, and, by way of example, may be formed integrally therewith. The crosslink member has a at least one elongate aperture 892 formed therein structured and arranged to receive at least one suitable fastener for securing the member 872 to other elements of the support structure 860, whereby the mediolateral positioning of the interlaminar member may be varied in response to the dimensions of a patient's skeletal structure. In the embodiment shown, the crosslink member includes two elongate apertures 892 symmetrically spaced apart relative to a longitudinal axis B-B of the member 872 of the support structure. In other aspects, one elongate aperture may extend substantially the entire length occupied by the two apertures shown in the Figures.

Referring back to FIGS. 47-49, and with further reference to the incorporated provisionals which better show the individual components, the support structure includes a pair of threaded eye bolts 895, each positioned in one of the apertures 892, each eyebolt having an eye portion or aperture 897 formed in a proximal end thereof, each adapted to receive and releasably secure a first or upper end 900 of a guide rod 902 therein and to adjustably position each on a patient's spinal column in response to the patient's skeletal structure and dimensions. Each guide rod 900 includes a cross member 904 operatively connected to a second or lower end 906 thereof, each cross member having a transversely extending body 908 including a first end 910 operatively connected to a respective lower end 906 of one of the guide rods 900 and a second end 912 adapted to releasably secure a second support member 920 thereto, as shown in FIGS. 54-56. In the embodiment shown, each of the ends 912 is in the form of hook-shaped member adapted to receive and retain a support member 920 with a set screw or retention fastener 914 threadably positioned therein; however, it is to be understood that other end configurations and guide rod retentions devices may also be used without departing from the scope of the present invention.

Referring now to FIGS. 54-56, each of the second support members is in the form of spinal or guide rod 920, each guide rod having an upper end 922, a mid-portion 924 and a lower end 926. Each of the upper and lower ends and the mid-portion of the support members has a securing device 927 slideably positioned thereon and adapted to be secured thereto by means of set screws 930. By way of example, each of the securing devices 927 is adapted to receive a pedicle screw 935, each pedicle screw being structured and arranged to be secured to one of the vertebra of the spinal column 18, thus facilitating the installation, adjustment and operation of the spinal stabilization in the manner as hereinabove described with respect to other embodiments of the present invention.

Figure 57A:
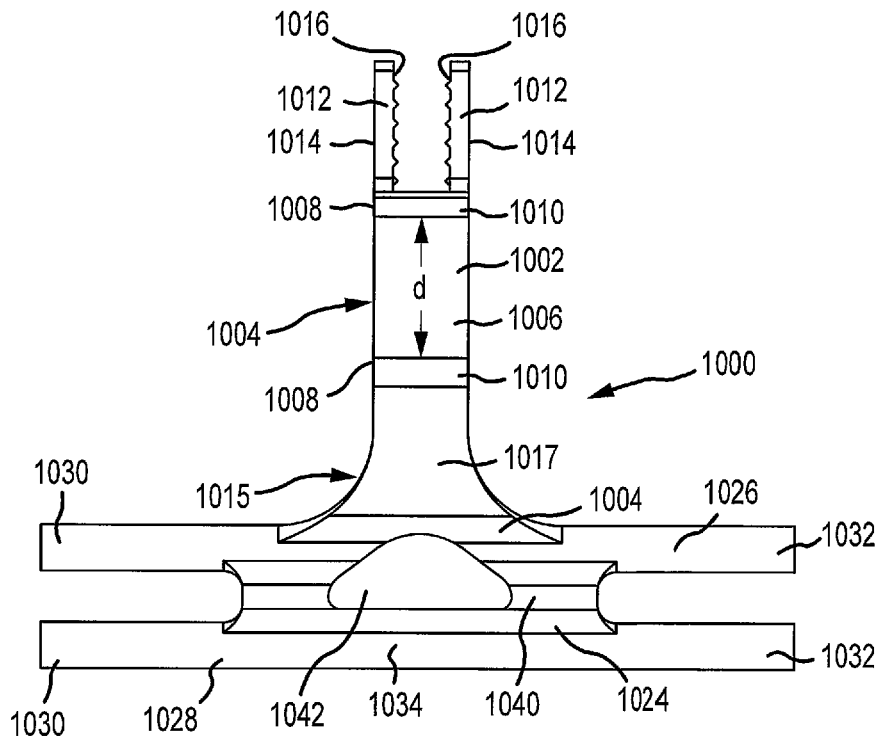
FIG. 57(A) is a front plan vie of a portion of a spinal stabilization system in accordance with an embodiment.
Figure 57B:
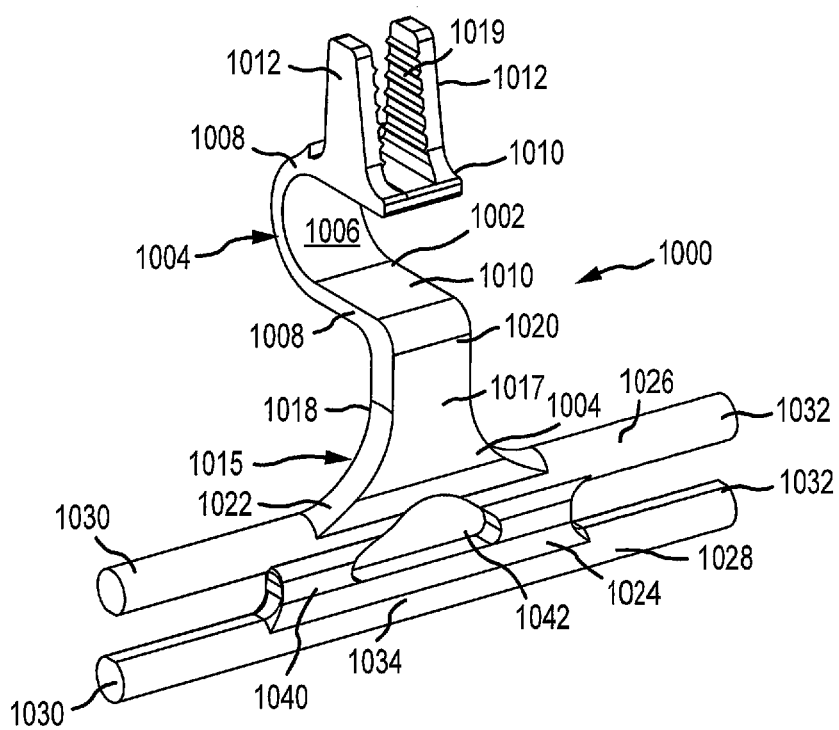
FIG. 57(B) is a top perspective view of the portion of a spinal stabilization system of FIG. 57(A)

Referring now to FIGS. 57A and 57B, a portion of an adjustable spinal stabilization system according to yet another embodiment of the present invention is shown generally at 1000. The system includes an interlaminar member 1002 adapted to be positioned between adjacent vertebra in a spinal column as hereinabove described with respect to other embodiments hereof and is operatively connected to a support structure 1004. In the embodiment shown, the support structure and the first interlaminar member are integrally formed from a single piece of material such as titanium or stainless steel suitable for use as a medical implant device. However, it is to be understood that other means for connecting the interlaminar device to the support structure such as hinges, pins, threaded fasteners and the like may also be used without departing from the scope of the invention.

The interlaminar member comprises a body 1004 defined by an elastic midsection 1006, two spaced apart end portions 1008, and a pair of juxtaposed legs 1010, each leg extending substantially parallel to one another from one of the respective ends in a direction generally outwardly away from a patient's spinal column 18 (FIG. 56) and spaced apart a preselected distance d. Distance d is determined by the size of the interlaminar member, which, in turn, may be selected based upon the spacing between a patient's vertebrae. Depending upon the situation, the interlaminar member may be intended to fuse adjacent vertebrae, or it may be intended to permit limited motion therebetween while at the same time maintaining the stability of vertebra with respect to one another. Accordingly, it may be sized to be a tight fit, and the elastic properties of the body's midsection 1006 act as a spring or shock absorber in the interface between the two vertebrae. In the embodiment shown in the above-referenced figures, the elastic midsection 1006 of the body is U-shaped. However, other shapes or configurations, by way of example, a V-shape, a W-shape or other function configurations may also be used effectively.

The interlaminar member 1002 further includes a pair of spaced-apart support members or plates 1012 secured to an upper one of the pair of juxtaposed legs 1010 of the interlaminar support member and extending in a direction upwardly therefrom substantially parallel to one another. Each of the plates includes an outer surface 1014 and an inner surface 1016, each inner surface having a plurality of teeth 1019 formed therein and extending substantially parallel to one another in a direction generally outwardly away from the spinal column 18, the plates cooperating with one another to be positioned adjacent opposite sides a spinous process of a patient's vertebra.

The spinal stabilization system 1000 further includes a T-shaped frame or support member 1015 operatively connected to the interlaminar member 1002 and which extends generally downwardly therefrom in a direction substantially parallel to the spinal column 18. The T-shaped frame member comprises an elongate body 1017 having first and second end portions 1020, 1022, the first end portion being operatively connected to the interlaminar member 1002, and the second end portion to an elongate cross member 1024. The elongate body 1017 is formed to contain an angle 1018 extending laterally outwardly away from a patient's spinal column to facilitate installation and adjustment of the stabilization system to accommodate a patient's skeletal structure.

The cross member includes first and second generally transversely and parallel extending cross members 1026 and 1028, each having end portions 1030, 1032 and a midpoint 1034 and is structured and arranged to be connected to the second end portion 1022 of the body 1017 at approximately the midpoint of member 1026. Each of the ends of the cross members are adapted to receive and adjustably secure first and second support members in the form of spinal or guide rods 920 respectively, as shown in FIGS. 54-56. The cross members are connected by a spacer member 1040 which has an aperture 1042 formed therein to reduce the weight of the system and to provide additional access to a patient's spinal processes during installation.

Figure 58A:
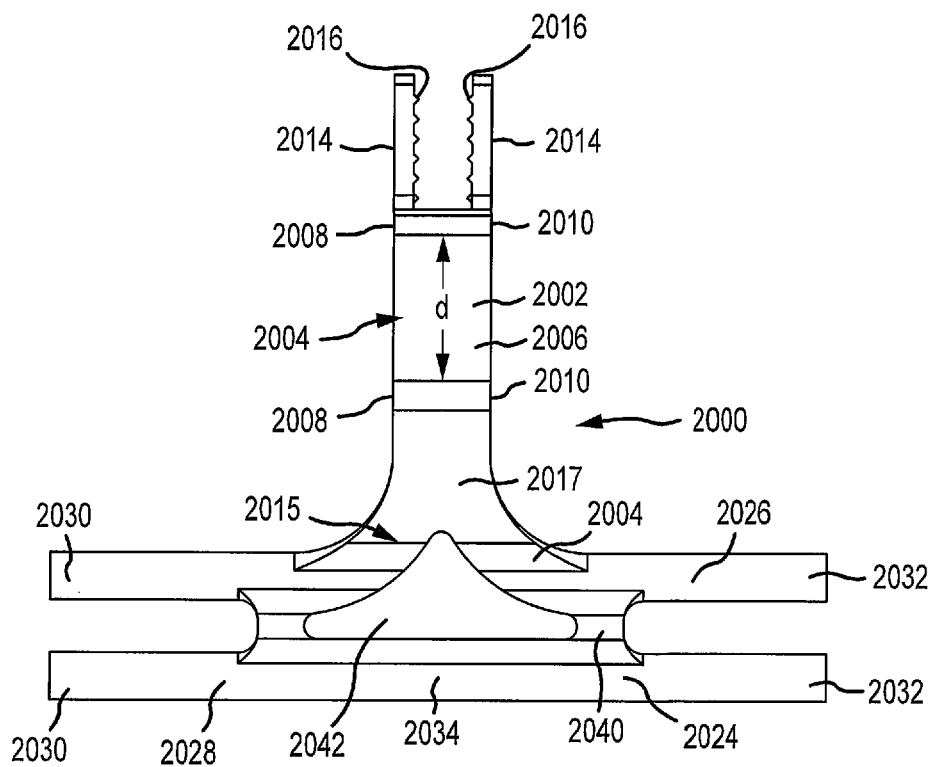
FIG. 58(A) is a front plan view of a portion of a spinal stabilization system in accordance with another embodiment.
Figure 58B:
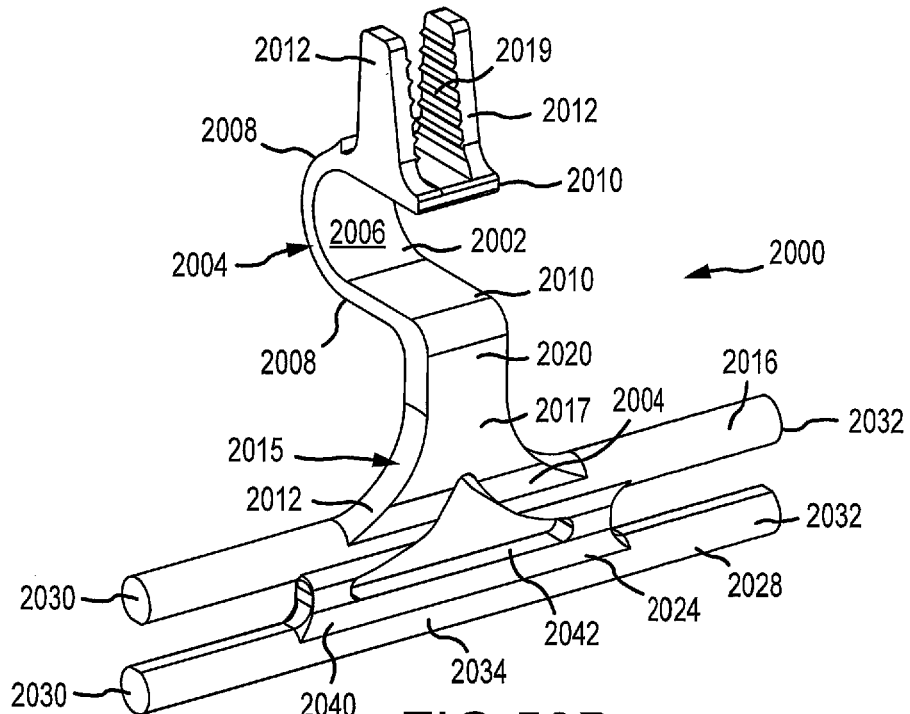
FIG. 58(B) is a top perspective view of the portion of a spinal stabilization system of FIG. 58 (A).

Referring to FIGS. 58A and 58B, a portion of an adjustable spinal stabilization system according to still another embodiment of the present invention is shown generally at 2000. The system is similar in configuration to the system of FIGS. 57A and 57B, but has an aperture 2042 which is slightly larger and of a different configuration than aperture 1042 of the previous embodiment. System 2000 includes an interlaminar member 2002 adapted to be positioned between adjacent vertebra in a spinal column as hereinabove described with respect to other embodiments hereof and is operatively connected to a support structure 2004. In the embodiment shown, the support structure and the first interlaminar member are integrally formed from a single piece of material such as titanium or stainless steel suitable for use as a medical implant device. However, it is to be understood that other means for connecting the interlaminar device to the support structure such as hinges, pins, threaded fasteners and the like may also be used without departing from the scope of the invention.

The interlaminar member comprises a body 2004 defined by an elastic midsection 2006, two spaced apart end portions 2008, and a pair of juxtaposed legs 2010, each leg extending substantially parallel to one another from one of the respective ends in a direction generally outwardly away from a patient's spinal column, again as shown as element 18 in FIG. 56, and spaced apart a preselected distance d. Distance d is determined by the size of the interlaminar member, which, in turn, may be selected based upon the spacing between a patient's vertebrae. Depending upon the situation, the interlaminar member may be intended to fuse adjacent vertebrae, or it may be intended to permit limited motion therebetween while at the same time maintaining the stability of vertebra with respect to one another. Accordingly, it may be sized to be a tight fit, and the elastic properties of the body's midsection 2006 act as a spring or shock absorber in the interface between the two vertebrae. In the embodiment shown in the above-referenced figures, the elastic midsection 2006 of the body is U-shaped. However, other shapes or configurations, by way of example, a V-shape, a W-shape or other function configurations may also be used effectively.

The interlaminar member 2002 further includes a pair of spaced-apart support members or plates 2012 secured to an upper one of the pair of juxtaposed legs 2010 of the interlaminar support member and extending in a direction upwardly therefrom substantially parallel to one another. Each of the plates includes an outer surface 2014 and an inner surface 2016, each inner surface having a plurality of teeth 2019 formed therein and extending substantially parallel to one another in a direction generally outwardly away from the spinal column 18, the plates cooperating with one another to be positioned adjacent opposite sides a spinous process of a patient's vertebra.

The spinal stabilization system 2000 further includes a T-shaped frame or support member 2015 operatively connected to the interlaminar member 2002 and which extends generally downwardly therefrom in a direction substantially parallel to the spinal column 18. The T-shaped frame member comprises an elongate body 2017 having first and second end portions 2020, 2022, the first end portion being operatively connected to the interlaminar member 2002, and the second end portion to an elongate cross member 2024. The elongate body 2017 is formed to contain an angle 2018 extending laterally outwardly away from a patient's spinal column to facilitate installation and adjustment of the stabilization system to accommodate a patient's skeletal structure.

The cross member includes first and second generally transversely and parallel extending cross members 1026 and 1028, each having end portions 2030, 2032 and a midpoint 2034 and is structured and arranged to be connected to the second end portion 2022 of the body 2017 at approximately the midpoint of member 2026. Each of the ends of the cross members are adapted to receive and adjustably secure first and second support members in the form of spinal or guide rods 920 respectively, as shown in FIGS. 54-56. The cross members are connected by a spacer member 2040 which has an aperture 2042 formed therein to reduce the weight of the system and to provide additional access to a patient's spinal processes during installation.

Changes may be made in the above methods and systems without departing from the scope hereof. It should thus be noted that the matter contained in the above description and/or shown in the accompanying figures should be interpreted as illustrative and not in a limiting sense. The following claims are intended to cover all generic and specific features described herein, as well as all statements of the scope of the present systems and methods, which, as a matter of language, might be said to fall there between.

What is claimed is:

1. An adjustable stabilization system for stabilizing multiple levels of a patient's spine, the patient having a head, a pelvis, and a spinal column operatively connected at a caudal end thereof to the patient's pelvis and operatively connected at a cephalad end thereof to the patient's head, the spinal column including a plurality of operatively interconnected vertebrae positioned at multiple levels intermediate the caudal and cephalad ends thereof, each of the plurality of vertebrae being separated from an adjacent vertebra by an intervertebral space formed between the adjacent vertebrae, the system comprising:

an interlaminar member adapted to be positioned in an intervertebral space intermediate a first one of the plurality of operatively interconnected vertebrae and a second adjacent one of the plurality of operatively interconnected vertebrae, the interlaminar member including a U-shaped body having a midsection, and two spaced apart end portions, and a pair of juxtaposed legs extending parallel to one another from one of the respective ends in a direction outwardly away from the spinal column when the interlaminar member is implanted;

a pair of spaced-apart support members or plates secured to an upper one of the pair of juxtaposed legs of the interlaminar member and extending in a direction upwardly therefrom parallel to one another;

a support structure structured and arranged to secure the adjustable stabilization system to the patient's spinal column whereby multiple levels of the plurality of operatively interconnected vertebrae are stabilized, the support structure including a T-shaped body portion having an upwardly extending member having a top portion opposite a bottom portion and including an angle extending laterally outwardly away from the patient's spinal skeletal structure, the top portion operably coupled with a bottom one of the pair of juxtaposed legs of the interlaminar member, a crosslink member operatively connected to the bottom portion of the upwardly extending member, the crosslink member having at least one elongate aperture formed therein structured and arranged to receive at least one fastener for securing the interlaminar member to the support structure whereby the mediolateral positioning of the interlaminar member may be varied in response to dimensions of a patient's skeletal structure;

a fastener positioned in the at least one elongate aperture and adapted to receive and releasably secure a first end of a guide rod therein; the fastener compromising an eye bolt having an eye portion formed in a proximal end thereof, the eye portion being adapted to receive and releasably secure the first end of the guide rod.

2. The stabilization system of claim 1, wherein the guide rod includes a cross member operatively connected to a second or lower end thereof, the cross member having a transversely extending body including a first end operatively connected to the second or lower end of the guide rod and a second end adapted to releasably secure a second support member thereto.

3. The stabilization system of claim 2, wherein the second end is in the form of hook-shaped member adapted to receive and retain the second support member.

4. The stabilization system of claim 3, wherein the second end further includes a retention fastener threadably positioned therein.

5. The stabilization system of claim 4, wherein the second support member is a spinal guide rod.

* * * * *